(12) United States Patent
Michalakis et al.

(10) Patent No.: US 12,043,848 B2
(45) Date of Patent: Jul. 23, 2024

(54) AAV VECTORS

(71) Applicant: VIGENERON GMBH, Starnberg (DE)

(72) Inventors: Stylianos Michalakis, Munich (DE); Martin Biel, Starnberg (DE); Christian Schön, Mietingen (DE); Hildegard Büning, Hannover (DE)

(73) Assignee: Vigeneron GmbH, Starnberg (DE)

( * ) Notice: Subject to any disclaimer, the term of this patent is extended or adjusted under 35 U.S.C. 154(b) by 856 days.

(21) Appl. No.: 16/756,054

(22) PCT Filed: Oct. 16, 2018

(86) PCT No.: PCT/EP2018/078175
§ 371 (c)(1),
(2) Date: Apr. 14, 2020

(87) PCT Pub. No.: WO2019/076856
PCT Pub. Date: Apr. 25, 2019

(65) Prior Publication Data
US 2020/0308553 A1 Oct. 1, 2020

(30) Foreign Application Priority Data

Oct. 16, 2017 (EP) .................................. 17196567

(51) Int. Cl.
| | | |
|---|---|---|
| *C12N 7/00* | (2006.01) | |
| *A61K 48/00* | (2006.01) | |
| *A61K 49/00* | (2006.01) | |
| *C07K 14/005* | (2006.01) | |
| *C12N 15/10* | (2006.01) | |
| *C12N 15/86* | (2006.01) | |

(52) U.S. Cl.
CPC .............. *C12N 7/00* (2013.01); *A61K 48/005* (2013.01); *A61K 48/0075* (2013.01); *A61K 49/00* (2013.01); *C07K 14/005* (2013.01); *C12N 15/1082* (2013.01); *C12N 15/86* (2013.01); *C12N 2750/14122* (2013.01); *C12N 2750/14143* (2013.01); *C12N 2750/14145* (2013.01); *C12N 2750/14171* (2013.01)

(58) Field of Classification Search
None
See application file for complete search history.

(56) References Cited

U.S. PATENT DOCUMENTS

| | | | |
|---|---|---|---|
| 5,478,745 A | 12/1995 | Samulski et al. | |
| 9,610,354 B2 | 4/2017 | Okada et al. | |
| 10,519,198 B2 * | 12/2019 | Deverman | A61K 39/3955 |

FOREIGN PATENT DOCUMENTS

| | | |
|---|---|---|
| WO | 1996000587 A1 | 1/1996 |
| WO | 2000028004 A1 | 5/2000 |
| WO | 2008145401 A2 | 12/2008 |
| WO | 2010093784 A2 | 8/2010 |
| WO | 2012145601 A2 | 10/2012 |
| WO | 2016134375 A1 | 8/2016 |
| WO | 2016141078 A1 | 9/2016 |
| WO | 2017218842 A1 | 12/2017 |

OTHER PUBLICATIONS

Wu et al., Mutational Analysis of the Adeno-Associated Virus Type 2 (AAV2) Capsid Gene and Construction of AAV2 Vectors with Altered Tropism, 2000, Journal of Virology, vol. 74, No. 18, pp. 8635-8647.*
Altschul et al., "Basic Local Alignment Search Tool", J. Mol. Biol., 215, pp. 403-410 (1990).
Altschul et al., "Gapped BLAST and PSI-BLAST: a new generation of protein database search programs", Nucl. Acids Res. 25(17), pp. 3389-3402 (1997).
Altschul, Stephen F., "A Protein Alignment Scoring System Sensitive at All Evolutionary Distances", J. Mol. Evol. 36, pp. 290-300 (1993).
Auricchio et al. "Exchange of surface proteins impacts on viral vector cellular specificity and transduction characteristics: the retina as a model", Hum Mol Genet, 10(26), pp. 3075-3081 (2001).
Becirovic et al., "In Vivo Analysis of Disease-Associated Point Mutations Unveils Profound Differences in mRNA Splicing of Peripherin-2 in Rod and Cone Photoreceptors", PLOS Genetics, 12(1):e1005811 (Jan. 21, 2016) (22 pages).
Becirovic et al., "AAV Vectors for FRET-Based Analysis of Protein-Protein Interactions in Photoreceptor Outer Segments", Front Neurosci 10:356 (Jul. 2016) (13 pages).
Boye et al., "A comprehensive review of retinal gene therapy", Molecular Therapy, 21(3), pp. 509-519 (Mar. 2013).
Brutlag et al., "Improved sensitivity of biological sequence database searches", Comp. App. Biosci. 6(3), pp. 237-245 (1990).
Cai et al., "A 350 bp region of the proximal promoter of Rds drives cell-type specific gene expression", Exp Eye Res., 91(2), pp. 186-194 (2010).
Chao et al., "Several Log Increase in Therapeutic Transgene Delivery by Distinct Adeno-Associated Viral Serotype Vectors", Molecular Therapy 2(6), pp. 619-623 (Dec. 2000).
D'Costa et al., "Practical utilization of recombinant AAV vector reference standards: focus on vector genomes titration by free ITR qPCR", Mol Ther Methods Clin Dev. 5:16019 (2016) (9 pages).

(Continued)

*Primary Examiner* — Benjamin P Blumel
(74) *Attorney, Agent, or Firm* — McNeill Baur PLLC

(57) ABSTRACT

The present invention relates to an adeno-associated virus (AAV), comprising an insertion of at least 6-8 amino acids between the positions corresponding to position 587 and 588 of SEQ ID NO: 1. Also envisioned are AAVs of the present invention for use as a medicament and pharmaceutical compositions comprising the AAV of the present invention. Further, the present invention relates to an in vitro use of AAV of the present invention for transduction of the nucleus of retinal cells. Also concerned is a method for screening an insertion sequence as well as a peptide obtainable by the method for screening. Also contemplated are kits comprising the AAV of the present invention.

17 Claims, 21 Drawing Sheets

Figure 6:
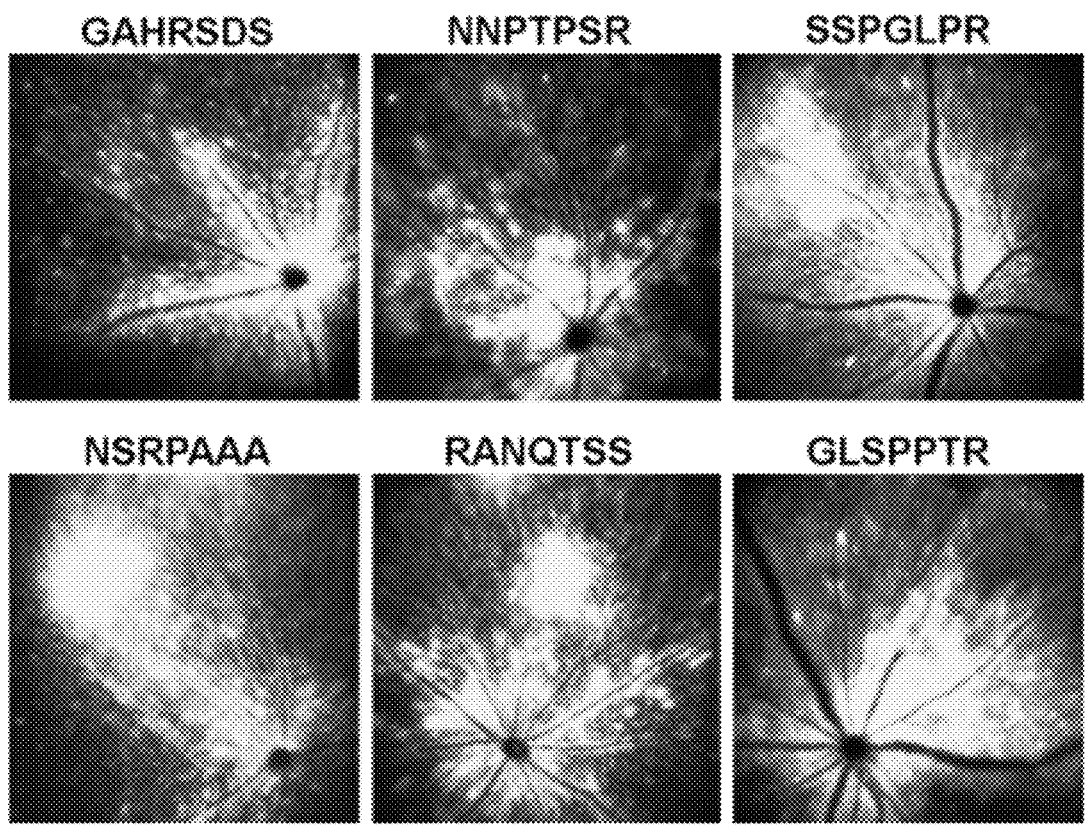

Specification includes a Sequence Listing.

(56) References Cited

OTHER PUBLICATIONS

Eberle et al., "Increased integration of transplanted CD73-positive photoreceptor precursors into adult mouse retina" Investigative Ophthalmology & Visual Science, 52(9), pp. 6462-6471 (2011).
Eberle et al., "Subretinal transplantation of MACS purified photoreceptor precursor cells into the adult mouse retina", J. Vis. Exp. 84:e50932 (2014) (9 pages).
Ellis et al., "Zinc-finger nuclease-mediated gene correction using single AAV vector transduction and enhancement by Food and Drug Administration-approved drugs," Gene. Ther. 20(1), pp. 35-42 (Jan. 2013).
Fei et al., "Transgenic expression of the jellyfish green fluorescent protein in the cone photoreceptors of the mouse," Visual Neuroscience, 18, pp. 615-623 (2001).
Fei Yijian, "Development of the cone photoreceptor mosaic in the mouse retina revealed by fluorescent cones in transgenic mice", Mol Vision, 9, pp. 31-42 (2003).
Feodorova et al., "Quick and reliable method for retina dissociation and separation of rod photoreceptor perikarya from adult mice", MethodsX 2, pp. 39-46 (2015).
Fisher et al., "Transduction with Recombinant Adeno-Associated Virus for Gene Therapy is Limited by Leading-Strand Synthesis", J. Virol, 70(1), pp. 520-532 (1996).
Fradot et al., "Gene therapy in ophthalmology: validation on cultured retinal cells and explants from postmortem human eyes", Human Gene Therapy, 22, pp. 587-593 (May 2011).
Girod et al., "Genetic capsid modifications allow efficient re-targeting of adeno-associated virus type 2", Nat. Med. 5, pp. 1052-1056 (1999).
Hacker et al., "Adeno-associated virus serotypes 1 to 5 mediated tumor cell directed gene transfer and improvement of transduction efficiency", J Gene Med, 7, pp. 1429-1438 (2005).
Hellstrom et al., "Cellular tropism and transduction properties of seven adeno-associated viral vector serotypes in adult retina after intravitreal injection", Gene Therapy, 16, pp. 521-532 (2009).
Henikoff et al., "Amino acid substitution matrices from protein blocks", Proc. Natl. Acad. Sci., USA, 89, pp. 10915-10919 (Nov. 1992).
Kahle et al., "Development of Methodology and Study Protocol: Safety and Efficacy of a Single Subretinal Injection of rAAV. hCNGA3 in Patients with CNGA3-Linked Achromatopsia Investigated in an Exploratory Dose-Escalation Trial", Human Gene Therapy Clinical Development, 29(3), pp. 1-12 (2018).
Kern et al., "Identification of a heparin-binding motif on adeno-associated virus type 2 capsids", Journal of Virology, 77(20), pp. 11072-11081 (Oct. 2003).
Koch et al., "Gene therapy restores vision and delays degeneration in the CNGB1-/- mouse model of retinitis pigmentosa", Hum Mol Genetics, 21(20), pp. 4486-4496 (2012).
Kotterman et al., "Engineering adeno-associated viruses for clinical gene therapy", Nat Rev Genet, 15(7), pp. 445-451 (Jul. 2014).
Lambard et al., "Expression of Rod-Derived Cone Viability Factor: Dual Role of CRX in Regulating Promoter Activity and Cell-Type Specificity", PLoS One, 5(10):e13025 (Oct. 2010) (16 pages).
Le Guiner et al., "Biodistribution and shedding of AAV vectors", Methods in Molecular Biology, 807, pp. 339-359 (2011).
Lebherz et al., "Novel AAV serotypes for improved ocular gene transfer", J Gene Med., 10(4), pp. 375-382 (Apr. 2008).
MacLaren et al., "Retinal gene therapy in patients with choroideremia: initial findings from a phase 1/2 clinical trial," Lancet, 383, pp. 1129-1137 (2014).
Maguire et al., "Safety and efficacy of gene transfer for Leber's congenital amaurosis", N Engl J Med, 358(21), pp. 2240-2248 (2008).
Mekada et al., "Genetic differences among C57BL/6 Substrains", Exp. Anim., 58(2), pp. 141-149 (2009).
Michalakis et al., "Restoration of Cone Vision in the CNGA3-/- Mouse Model of Congenital Complete Lack of Cone Photoreceptor Function", Mol Ther., 18(12), pp. 2057-2063 (Dec. 2010).

Michelfelder et al., "Peptide ligands incorporated into the threefold spike capsid domain to re-direct gene transduction of AAV8 and AAV9 in vivo", PloS One, 6(8): e23101 (Aug. 2011) (11 pages).
Millington-Ward et al., "Suppression and Replacement Gene Therapy for Autosomal Dominant Disease in a Murine Model of Dominant Retinitis Pigmentosa," Molecular Therapy, 19(4), pp. 642-649 (Apr. 2011).
Morrissey et al., "PRE-1, a cis element sufficient to enhance cone- and rod- specific expression in differentiating zebrafish photoreceptors", BMC Dev, Biol, 11:3 (Jul. 2011) (12 pages).
Muhlfriedel et al., "Optimized technique for subretinal injections in mice", Methods in Molecular Biology, 935, pp. 343-349 (2013).
Mussolino et al., "AAV-mediated photoreceptor transduction of the pig cone-enriched retina", Gene Ther, 18(7), pp. 637-645 (2011).
Muzyczka, "Use of Adeno-Associated Virus as a General Transduction Vector for Mammalian Cells", Curr Topics Microbiol. 158 Immunol., Viral Expression Vectors, pp. 97-129 (1992).
Nathwani et al., "Long-term safety and efficacy of factor IX gene therapy in hemophilia B", N Engl J Med, 371(21), pp. 1994-2004 (Nov. 20, 2014).
Nicklin et al., "Efficient and selective AAV2-mediated gene transfer directed to human vascular endothelial cells," Molecular Therapy, 4(2), pp. 174-181 (Aug. 2001).
Nicord et al., "Development of photoreceptor-specific promoters and their utility to investigate EIAV lentiviral vector mediated gene transfer to photoreceptors", J. Gene Med, 9(12), pp. 1015-1023 (2007).
Ochakovski et al., "Retinal Gene Therapy: Surgical Vector Delivery in the Translation to Clinical Trials", Front Neuroscience, 11(174) (Apr. 2017) (7 pages).
Opie et al., "Identification of amino acid residues in the capsid proteins of adeno-associated virus type 2 that contribute to heparin sulfate proteoglycan binding", Journal of Virology, 77(12), pp. 6995-700 (Jun. 2003).
O'Reilly et al., "RNA Interference—Mediated Suppression and Replacement of Human Rhodopsin In Vivo", Am J Hum Genet., 81, pp. 127-135 (Jul. 2007).
Perabo et al., "In vitro selection of viral vectors with modified tropism: the adeno-associated virus display", Molecular Therapy 8(1), pp. 151-157 (Jul. 2003).
Perabo et al., "Heparan sulfate proteoglycan binding properties of adeno-associated virus retargeting mutants and consequences for their in vivo tropism", Journal of Virology, 80(14), pp. 7265-7269 (Jul. 2006).
Petrs-Silva et al., "High-efficiency transduction of the mouse retina by tyrosine-mutant AAV serotype vectors", Molecular Therapy, 17(3), pp. 463-471 (Mar. 2009).
Sallach et al., "Tropism-modified AAV vectors overcome barriers to successful cutaneous therapy", Molecular Therapy, 22(5), pp. 929-939 (May 2014).
Zolotukhin et al., "Recombinant adeno-associated virus purification using novel methods improves infectious titer and yield", Gene Ther., 6, pp. 973-985 (1999).
Schon et al., "Retinal gene delivery by adeno-associated virus (AAV) vectors: Strategies and applications", European Journal of Pharmaceutics and Biopharmaceutics, 95, pp. 343-352 (2015).
Simonelli et al., "Gene therapy for Leber's congenital amaurosis is safe and effective through 1.5 years after vector administration", Molecular Therapy, 18(3), pp. 643-650 (Mar. 2010).
Sonntag et al., "The Assembly-Activating Protein Promotes Capsid Assembly of Different Adeno-Associated Virus Serotypes", J Virol. 85(23), pp. 12686-12697 (Dec. 2011).
Sun et al., "Adeno-associated virus-delivered short hairpin-structured RNA for androgen receptor gene silencing induces tumor eradication of prostate cancer xenografts in nude mice; a preclinical study", Int J Cancer, 126(3), pp. 764-774 (2009).
Tan et al., "Expression of cone-photoreceptor-specific antigens in a cell line derived from retinal tumors in transgenic mice", Investigative Ophthalmology & Visual Science, 45(3), pp. 764-768 (Mar. 2004).
Thomspon et al., "CLUSTAL W: improving the sensitivity of progressive multiple sequence alignment through sequence weight-

(56) References Cited

OTHER PUBLICATIONS ing, position-specific gap penalties and weight matrix choice", Nucl. Acids Res., 22(22) pp. 4673-4680 (1994).

Trapani et al., "Vector platforms for gene therapy of inherited retinopathies", Prog Retin Eye Res, 0, pp. 108-128 (Nov. 2014).

Wang et al., "Sustained correction of bleeding disorder in hemophilia B mice by gene therapy", Proc. Natl. Acad. Sci., USA, 96, pp. 3906-3910 (Mar. 1999).

Xiao et al., "Production of high-titer recombinant adeno-associated virus vectors in the absence of helper adenovirus", J. Virol., 72(3), pp. 2224-2232 (Mar. 1998).

Xie et al., "The atomic structure of adeno-associated virus (AAV-2), a vector for human gene therapy", Proceedings of the National Academy of Sciences of the United States of America, 99(16), pp. 10405-10410 (Aug. 6, 2002).

Zeitz et al., "Whole-Exome Sequencing Identifies LRIT3 Mutations as a Cause of Autosomal-Recessive Complete Congenital Stationary Night Blindness", Am J Hum Genet., 92, pp. 67-75 (Jan. 10, 2013).

Zhong et al., "Tyrosine-phosphorylation of AAV2 vectors and its consequences on viral intracellular trafficking and transgene expression", Virology, 381(2), pp. 194-202 (Nov. 25, 2008).

Zhong et al., "Next generation of adeno-associated virus 2 vectors: point mutations in tyrosines lead to high-efficiency transduction at lower doses", Proceedings of the National Academy of Sciences of the United States of America, 105(22), pp. 7827-7832 (Jun. 3, 2008).

Dalkara et al., "In vivo-directed evolution of a new adeno-associated virus for therapeutic outer retinal gene delivery from the vitreous", Science Translational Medicine, p. 189ra76 (Jun. 12, 2013).

Michalakis, S., "Development of novel AAV variants with superior photoreceptor transduction properties", Human Gene Therapy, 28(12), p. A75 (Oct. 17, 2017).

International Search Report in International Application No. PCT/EP2018/078175, mailed Jun. 12, 2018 (6 pages).

Written Opinion of the International Searching Authority in International Application No. PCT/EP2018/078175, mailed Jun. 12, 2018 (8 pages).

* cited by examiner

Figure 1:

| | | | | | |
|---|---|---|---|---|---|
| NQTKATA | TGNNPGR | SADPSA | NSTSVNR | LSPDSSS | MSVRPGG |
| NTVRSPT | GLHRSSS | NVASPTR | LLGPGRV | VTASRVA | TNQAASR |
| SQNDSRS | ARECNTT | TGRSATI | GGNSTKC | MRADRDP | GCDPRTS |
| TDNGSRS | GVNGLPK | VTPANPE | MTHAPRA | RMPGHVA | ANPCPDA |
| RANQTSS | LRGDNPQ | VSTTVSC | YLCPTGG | PIPEHAP | GAPPNVG |
| GSNRTSD | DQTGDSE | RADPLEL | VNSGCPS | PGVPNHT | LSPAARS |
| SNNASRT | GSCHDST | SNGPCSA | YVGTDSS | KGGDGNR | SHANPPC |
| PDNFSRS | SHSPPVR | PLSGRTP | ERSNPSK | APAAECF | PSDAQAG |
| ENHVGRN | DLSGAPC | ARDGLPR | AYEPRSD | RASEVPR | VSTTSQR |
| ATNATRS | GAHRSDS | GSGVASS | TGSSQLR | LPPPPR | IGVGTAR |
| GGNSTKS | NSRPAAA | HSARTDS | GISRSGV | SDSTVRP | IRPESPR |
| PTPPGL | DRPQLVR | SGTEGHS | VSTSSSR | ISVRQPV | FELPGHP |
| IGETPGA | RRDESAR | VDKAVVR | TTATPAR | ARVGGGS | TGLSPNR |
| DDNRASP | RSDGGMK | ACSDTGR | ASPALA | NVSAARP | IKDPPVR |
| TTRAPTS | GTELDRA | GGARVAS | IPGRTA | HDAHSSR | PGLAAGW |
| TDNHAR | ARRTDGP | CSAARLV | GTGDNV | DSTGTRD | RRTLSDA |
| APTALRN | DSRPVK | GTGTELD | FDNCTDR | ASARDFA | GGGLERS |
| SPLPATR | GDDRPSR | AQPCALA | GRALQSG | ANSSIRA | AARMPTG |
| NTVRSP | SQPPINR | PSGRPCE | GLAGMDS | ASGSTPT | KSDARAS |
| GLTAAHR | PINNPPR | MSQTPAG | VSPTNGR | GKHGVQS | GSPSHEA |
| KSGAANP | PLRDLGT | TTSRLTS | GRPSIPG | GSDGGGR | VTVPSSR |
| ATDNHAR | KAVSDRS | MVSGAIA | AATPCTP | GYSRPPS | TTPDCPS |
| PNSARLA | QRMDARA | RRSDGQN | NAGRVGP | INATGDR | ASPVVPG |

Figure 1 (cont'):

| | | | | | |
|---|---|---|---|---|---|
| VSSDRSV | EGTGQLC | GATGVGK | AATMTVP | RQESRLT | SSGIRQD |
| VSGVRSA | GQTSRVG | MGAPAQR | CLHDLRT | AKTSLTL | GSGVATG |
| PSSEDSP | PPHLTSR | RGNGQHS | PSRADHN | CQPLRDL | TPARSTD |
| GATSQTE | TTTFPAR | DRRDCAD | CGEAVLE | LGATNPR | GNTPDQA |
| SPAPLSR | YVCPAPS | GECRSRD | NPCAGHP | PNGGAMR | TGNNPGP |
| GGVKGGS | PATARSS | GKLAECF | PTPLGL | KGQVEFR | SKPQALS |
| ASACETS | ARGTIDS | SSRAAVG | TPLVLP | VSSSTPR | SQNDSPS |
| GVVRPPS | SLSGSLT | GRDSNRG | PRPHRS | IGRGQGA | NTVRSPH |
| ASGPRTA | MKREAPH | KHTTTPG | TNNPPP | TRGDGAQ | PAVTLL |
| GGAGRAD | DLSSRTH | NGSPTPS | LALRTA | APAAGLK | WVARIP |
| SNPGRS | PVMRRP | AASSPRT | APGAPL | TDPTRCK | DNPGLA |
| DCGTHS | PVMRRS | INQGPPV | GVLAVR | PSDAQVG | SHANPP |
| GSNVHP | SLAIVS | TNGPSSR | PAAPTT | GMPSTLR | YRPLLR |
| IGETPG | QPLDTH | GSSHAAR | HRSPNSA | NHTLSPR | PLAARA |
| VSMGSR | PPPRVC | ATNPATR | KGASAPP | PAPCSSA | PTRAPP |
| WGSSRGE | LRGDNP | NYNPAAP | DSSRLPD | SGPTLQR | PPPATL |
| GRSDGQR | HSARIDS | RLCSPGE | RRDAAPS | QDGGGGR | RLGGPI |
| EAPQLAG | MPVSRSG | GVSCPTE | IKPGGHA | TTATPGR | PSSQPA |
| LAPRTGN | GGELGRR | RTGTLGI | ASRGIER | GETTLGR | RTAPWA |
| THNHSSS | IGTGTAR | GGNSSKC | RLASGGA | SPVSTTR | PSTPAI |
| RPPDGLR | GSPALRV | MNAPPVR | APGGAPK | SDKFAPT | PDNFPG |
| RGLPQAG | SNATTRA | NRSGEPR | ERSNPTQ | QGSSVNR | PCATSA |
| IHESPGT | RHESRLT | RTNAMER | MPITLPR | PLDARHS | PRWLAS |
| RTPHLAS | IGETPRG | GSSSIQR | RGGEVPR | AQNRSAS | ADPPSA |
| EDAQGHS | ALATPLS | MPPVPQR | GDDSRCS | QHMRASS | KGDGAR |
| DACEAGP | MSAQGPR | SPVVLSR | RTSDGRP | QRMVARA | PGLTEA |
| DHISRER | VPPANLR | GSRAYSS | GSGDGED | MTCPHPA | |
| DCVSTSA | IGGRIGG | SHSRHVA | QGGRSGA | SATCPAP | |
| VTQQLRH | AHHSAHG | SNATPRA | RGSGAGA | GDRVGDP | |
| SRTGSNQ | SDNCHLP | TASDPQA | RNAALTP | NTVHSPT | |
| PSPTSAK | AKAVGYG | KNIHPGA | APQCPDP | SGEALRD | |

Figure 2:

| | | | | | |
|---|---|---|---|---|---|
| RANQTSS | VLAGSPI | GSTANLR | APANLPR | NRSATDA | ERRLGGS |
| SHPRPGV | LSRVSSA | GIGSPGR | GNRPSGN | TPATPVC | SFGGAPR |
| ARSPIHP | HAAGLPK | STNATGR | MGHSSPR | PGSHSLR | PPGLGRS |
| SFGGAPK | SSHGLRP | HSARTDS | PSSPVAR | TAPAVSQ | ERRLGGR |
| AARGGGG | ATAGPTK | GGAGNGK | VTSSTSL | MGAVVAR | PLQAAPT |
| HTGRGES | ASGPLNR | NNPTPSR | ANMGPDC | ARSMTPV | HRAPNPS |
| MARAHVP | IALIRFD | SNTSPGR | ALQRPSH | GKGDTAR | RADQTSS |
| ASRDAQI | AVGVLRS | GRSMSSA | RRGLDPV | PLQAAPH | GIGSPGH |
| VAKPQIG | AITSLTR | SSAPTRS | SQNDSRS | DAGRRAA | RAKQTSS |
| ASAPSAR | PQAARST | VSNARIP | RGSDPPR | AAPTPLR | PSRPPPT |

| | | | | | |
|---|---|---|---|---|---|
| TSHGLRP | VARPQIG | SQAARST | AAKPQIG | AVGVHRS | AIMGPDC |
| RSAGHVV | NRSAADA | ARNPIHP | PTNATGR | YAGRRAA | DAGHRAA |
| ASRGAQI | HGARTDS | ASMGPDC | PLQAASH | VSNAGIP | RRGLNPV |
| AAPTPSR | GRSMRSA | RANRTSS | RGSLQNA | IALIWFD | ASGPLNG |
| PSSSVAR | DEAPWGS | RANQASS | ERRLEGS | SFGSAPR | GEAGNGK |
| AVGVLRG | SSAPTCS | ANMGPGC | GGAGNGE | SFGGTPK | MGAVVAC |
| ASGPHNR | TRSPIHP | SITSPGR | YAAGLPK | GHPRPGV | VLAGGPI |
| AARDGGG | ALQRPSR | AARGGGS | MRHSSPR | GRSVSSA | VPAGSPI |
| SSTSPGR | ASRDAQT | RGSHPNI | SSAPARS | PGSHSPR | ERRLGS |

Figure 3:

| | | | | | |
|---|---|---|---|---|---|
| GAHRSDS | VAGKVPW | NPRATSW | ATHGILK | SSPSMPR | PQPHLAK |
| YSARAPG | KGDTAAR | VGSAAAR | PSGGPPR | NQHSAAR | PALVGTL |
| VQPGSPR | YARANSA | TVSSAGR | GRVPAPG | SPLAHAK | RDSHPIR |
| ASRERER | ATADPRR | PSGAPAR | RRDAAGS | DSVHPHR | RYDTPGR |
| TTIPAGR | LAAGVPR | VDSYDSI | SSPGLPR | VVGVPAR | ASLLTGP |
| NGAATPR | GPGPILR | NVASPDR | RLHPNVP | SVNAPPR | FSGQGAP |
| SQETAGL | VSSALGR | GHLKGLT | VPSANAR | VASQRAS | STVQPSR |
| AATTTGR | GTVQAAS | MNALPRA | RVTTSPN | TGMPGLL | RDRATSP |
| GRLHPVH | SKVNTVA | GSGPTDR | DRSGSLR | SRSASDR | PPGNQAR |
| HPADIRS | DTGTHGR | RADRGLV | ASGRSLI | GKARDSA | NSTSVNR |
| NGRPTSS | VSHTSVG | GPMLQRS | SRVDMVR | GVGPPQH | SVGLGVK |
| NRPASDK | GDPSYRS | NLKPPAA | ANSVARP | GGVLAGR | AGRSGGY |
| QARLDPT | TRSLTHP | GTMRREI | SVPARQH | SSSAGTR | ASPSFGR |
| NAPSTVR | GARSNA | QPRRPGI | GLSPPTR | KEPPTAR | FKHPGAA |
| GHSARSI | GPGAAAK | SISATAR | SSEGVPR | SQAGVLR | RTSHAVG |
| STRLVPA | VPPAPGK | AHGTSRP | AQYSAAV | RSNVVSV | KHERPVS |
| ATSATQR | LSRSSGS | GSTGTVK | PADPRRT | VEYPLAP | NLGPGAK |
| NSTRPGV | ATKAPGY | HRNPAVG | RTGKNGG | SLGGSPR | RRLGGIE |
| NDSRTPC | TAGALGR | SSSARTF | TRDLSPR | GPRTSVL | RVRWLVP |
| VRSHFGS | RGSGAAY | DGWFDTG | PSGLSTK | SATTTSR | VRDATAR |
| TARVNPS | RSGHPGP | ARVAVTP | SSRDSRD | RNTHGLP | NASRPNM |
| SGVAAVR | KHTPLMG | TSLVAGR | AVDHRLP | SRAHVSA | YAVNRPA |
| RPARQLD | ATVGPSR | RTNSGPH | RDGASPR | SRTTSQH | SNPALRM |
| NSGRASS | PGQAANR | RANPHGP | SGARLST | RAAASTG | SAKVAIR |
| RIGQETR | TDRLAAR | GQPMPSR | ASNVLRF | GGIPSGS | AAVNLGR |
| SAPGSPR | NATRPAP | ARSTPY | VSSSSRP | TGRSTGY | GATPRAP |
| NSASQPR | RLNSTAS | SRGHPAP | KTGEPLR | GVGSTVR | VTGTGIR |
| SASAVAR | NSRPAAA | AGRGYTN | WSGGSPK | TVRGLQG | SLDPRRC |
| ISSSTAR | RSGAAV | NDPRRNP | SNRPAAA | STSPSPR | AKVSPNS |
| ALPTSQT | RSDPLVR | VGTGLNR | AGAPSYD | GSQPPGK | GGPYPAR |
| KLAQTVS | VASLAAR | RSNTTVA | PNAVARS | RVSVVSQ | RDGPPAK |
| GIAPVAR | TRVASPS | ASPPLR | QLRRDLE | GAENWTR | SPTPTGR |
| FPPGSAR | GMRATAA | CYLPACA | ATNRVSV | IVSAPTR | GVAARPI |

Figure 3 (cont'):

| | | | | | |
|---|---|---|---|---|---|
| TRGHLAG | ASVSRQS | ARTPSPG | VATPSSR | ADAGLRPC | SSLPCLAR |
| RGHASTV | APARLNS | TRTPSPY | GSPSMPR | RSRYQDAR | PPLVARLA |
| RTHRPDD | GRLSVPH | GAQPRNV | RNQTGAA | PGTGRPPP | PQGRARAR |
| RREGVTA | RGSLQNA | RTAPHFG | HVPPQIR | FPAGPTRA | VQPGSPAR |
| GSYVQAE | RDVASVK | HVSPQIR | SRVGMVR | VIGPLLLR | QHVPPSGR |
| SYTNAAR | SGNADLS | GKVVPHT | PTDPKRV | QAGHCGLR | PPLGLSAR |
| GRGPLPS | GRGNSVS | ARSATAA | ACRSGGY | AALPIPVR | PPPSNLGR |
| SGGNAGK | ATPADRM | HRAPAPM | REGVGGK | GARSNAA | QPPPSLAA |
| GGGRSFS | GGSPPYR | SQPPSQR | HKSARGD | LPPSRRAG | GPSLTPRG |
| MTTASRQ | PSSGHAH | PNQAPPR | GAHRSDP | HHYPRWPR | GPSLTPAR |
| AKALAES | TNPRPSV | TAKGIGL | LLDPRRC | GGIPSRQR | GTHSTPAR |
| GRLTQPS | AASPLEV | GQATKPI | GCLSVPH | TNPPSLGR | QTSDHPPR |
| CVSRGTC | TSTAYSR | GTHSTPR | GGSIHSG | SSMGPARG | PHQQAGER |
| ASRAAGA | SATALGR | AWRSSP | AVNLGR | VPMLPRRR | AGDAAERG |
| FKPATGA | SGIRLAG | SIAGPPR | PRWIVR | PLRSAPPA | ASVSPSER |
| PVTRAIP | SVRGAPPR | PLSAPTR | AAANLGR | MPPASPGR | RQPRPALL |
| SGKPLHG | SSNGTPR | APRANTP | RTGKNGC | LRRQQARC | AGQCCPRQ |
| TSHRPPA | RLDGRAS | QLPVHNA | ASPPLRA | RAWAFAER | PQRGRVAS |
| GVRAHGE | TAPVRMG | SPGAGQR | RVMTSPN | GPLACPPR | RRSPVRLR |
| TDLRPTK | RNAPSHL | PTHIPRS | GLSPPR | RLPFHASR | RRSQVRLR |
| INGVKSM | NDPRGPR | NSAGTPR | TRVAPPS | RCPPPSEV | QPQAARRR |
| VAGSTPR | SSAHKSL | GFRGSGL | AVTANGR | LAPLTLSR | PQHPWPAR |
| NGAHLSR | VSLGGPR | SVNPTRG | YRTTGRV | PTRLLPAR | ALTLTAPR |
| YSAGSPK | SPIVPAR | SPQNLRP | SATTTPR | LSRSSGSA | SVRGAPPR |
| DDLHARK | SRDRPSS | NATPYPR | ARMGSPR | TLHSHATR | GKVVPTPR |
| GAPRPTI | YQTPPLR | AHQGSPR | NAPTSSR | AGRSGGYA | PTGRSTRY |
| NPARAVV | LTSTGAR | FNTGAPR | FNTGAPA | AGRATPTW | PGPRTRVR |
| NFRDASA | KRGPDAV | TASPSHR | RANPRGP | ARADPLNG | QAGPLDAV |
| TMAPRTP | TGARIAP | PAGIVR | RSGHSGP | RQQRPPVC | RAGPPRAR |
| AAPPHTR | TPGSLSR | SSPALQR | TRSQTHP | GSLLVRLR | HNAQWRTQ |
| YRTTGQV | LKSDLSR | VPHAPPQ | GKVVPPH | RPDGPSRP | TRDLSPSR |
| RGAAGTI | PHNKPVS | AARPPAH | GSTGTVR | LRRAPGA | LQLQRKRG |
| GLAQGLR | GRTHPPY | GPTGLPP | VPPTPGK | KATLRLVR | APTVPSLG |
| SRSPHVP | AQMGSPR | PKDPLYR | GPRPILR | PPRRQGQC | ANSRRDPP |
| VHPPQAK | MGAVAAR | SGGANPH | GVENWTR | PSLRPRPC | RCLPPRGY |
| PVLNPPP | STQRVHP | ALAPQYR | HTARPHV | PTLRPRPC | AAAGILKA |
| ARAGRDL | VSSSLQR | IISGPPR | IVSTPTR | AGRSGRIC | FKHPGAAA |
| ARASHLV | DHDSPSV | QTSITPR | QARADRER | SVNPTRGR | GAQPRNVA |
| PPGYAAL | SRHFSGP | IGPSSPR | QRPTRPGV | NAPGVPGR | RVSVVSQA |
| VAQQFGR | SPAMPIR | ATHSFGG | ATVRRRAA | RQRPTHRE | ARPVRAKT |
| NAPGVPR | LRVSLPS | SLTPRH | GRVPAPGG | QRPQHREG | LLRRLPLR |
| TFIGARA | NTTRGNL | SLTPPGH | PRRLPLRR | QRSPAQPG | AGRAAPTE |
| AVTTNGR | SNSPAML | SLPHQAR | VPSANARA | QAPGWHPT | LPVSPCMV |
| FPAGPTR | PRDALGR | CAVNRPA | PVRGAARR | RETALPTR | AGRSPPGR |
| NAPQSSR | SSRITAA | GIQLPGK | AGSYVQAG | RGSGSWRG | LSHAEPRG |
| WHAPTHG | GPSLTPR | SGGRTAS | AGRGYTNV | GPPAPARR | PLSRRAAR |
| HSTTSGS | KEGGVVR | ISMGAPR | GHSARSIA | APPAPARR | ASPSFWPG |
| LTTGAPR | KGLHGGM | PQAAAFK | GTARGALR | VPPRPWPR | QPGAPAPR |
| RGNAHGP | GNQAPAV | SGVRLAG | ASREPGAC | RHDSSRGA | PAPATPSA |
| GRSIHSG | QNRTAAA | SGGRNPH | AALGSLAR | RPYHPRTR | QDRTALTT |
| ALTEGLR | GQRAPVS | LRVVGGA | PGVRASPL | QPTAPRHR | FPAGPTSR |
| AGRSSTW | LPAMATR | PNRVVGT | QCPPASPG | GTMRRESR | FPAGPDSR |
| AAAGILK | | HRAPAPT | PKDPPLPR | QPEGAPAS | GTRPLLWR |

Figure 3 (cont'):

| | | | | | |
|---|---|---|---|---|---|
| QPARLRQG | NPRASSW | AGRGYTD | TDPVPRS | TEVPDHP | GPRPHPA |
| GRPDTLPP | RYDSPGR | AGRVYTN | TNSRPSV | NSAGTLR | DTGTHER |
| ATPRPSAA | GIQLLGK | AGRDYTN | GRTTPVR | AVDHRSR | AGRERER |
| QHLAVAPG | NSTRPRV | AGTGLHQ | ENQAPAV | AGRSPLP | AAPPPYP |
| TASPQSSR | TTGALGR | GRTTPRT | GLTPPHE | SPTPHRS | ARRWPEC |
| QLRGAPPR | TAGTLGR | AGAPSFD | SSGILGT | GPIGLPP | SGKPLHW |
| SIAGPPRR | LPAMATP | NPARRRG | GHSAQSI | NATGRPR | GGGRTAS |
| PPTSLAAR | PPLLWPP | GHSARII | SWGGCGP | GPTGQPP | TSHRLPA |
| AGASTAVR | RQGVPPT | GHSGRSI | SGAAAVR | VPSADAR | YAVNGPA |
| PTTDPVAA | IGPSSPA | RTAPHLV | TRSLDLP | VLSANAR | ARVAATP |
| AGECRLLR | RPPCRYS | GHSARST | SLTPPAR | VPLPTPA | AVSAPCP |
| RPTGPTAA | IGPTLPP | TRTPLPL | GKSSPHR | VPSAQRP | STPHHCC |
| PLALLRAR | TMAPPHP | KHTPPHG | SSPSMPH | RGSGTAY | TSHPPPC |
| PARSSPTP | QAHPPSM | ATVGRSR | KAESLNR | TTIPARP | SGGASPH |
| RRPRHGAR | GGVALMP | NTPAATW | VAAGILK | GAHQSDS | PSPGHAH |
| PRTPRSRG | VASLAGP | NITRGNL | ACDVSSR | TGRLLSR | RTNFGPH |
| AATEARAT | KHTPSMG | RADRGLR | IRWGPAR | KEGVLCG | RTNSGPP |
| HAQAPRHR | GFLARAC | TEMPGLL | ISMGPRA | KEGGCCA | SSLSQRR |
| HRERAIGL | LPAMPIR | SGEANPH | ISSGAPR | NGGGCCA | QAWRRRG |
| RAQRAEHC | NRPASDR | SAKVAVR | ASGRSLT | HAVPPPA | SASAPRG |
| AQAGTLRA | VGSALGR | FKHTGAA | RDPTARP | SSPGLLA | VRRPPPR |
| PAPATPCG | GHPKGLT | KGDTAAL | PPERPTR | SLPHQAH | QLHRDLE |
| LPHPHRSR | QTRLDLT | PEGPLYR | SATTTLR | ASRARGR | RRLGASR |
| GTVQAASA | QARLDLT | GITPVAR | QTSIHPR | RSGAAVA | PRTGSAR |
| GSGPTDRA | SGGECGQ | GIAPVTR | PRRRSTP | VLLAAPA | KQREPAQ |
| AHGTSRPA | LDRSSLA | ARTLPRG | NDSRTPS | EGGVAQP | LSGDCRF |
| LRQAPCMV | GPHWPAP | SHASFPA | TRMPGLL | GTVQAVS | SNPALLM |
| RRTAPLLR | PIAWWGP | TSKPPAA | RGSGAAC | VRPARRR | SGGRTRM |
| PTLRPPPT | SVNPPGG | GTAPVAR | HRAPAPL | SGNADLG | ATPARPH |
| HVAPAPLL | RYDAPGG | SRVDMVC | RDGRPPR | PPRPIFG | HRAPAPW |
| QGAARRYG | PRPAALK | PQQAGER | CSARAPG | HRPRPPG | HRARPHG |
| RPGVRRLG | TDLRRPR | DSAGTPR | VPHAPRR | GSTGTVN | HRARPPW |
| RCWQYPEG | PAGSCPR | YSAGHPG | HSTTSGR | PSAPPGQ | PSRPGPH |
| VPPAPGQG | PIAWWGT | NGPRGPR | VPHASPQ | AGRGYAN | HRAPAPH |
| QPRRPASR | GARACPR | SSGAGTR | APHAPPQ | ARADPST | ATPDRPP |
| PPGVPGLL | GRCPCRP | WHAPAPW | VPPCSPA | RSGHPAR | PSRPGPP |
| RASPCRLA | AGRGYSN | VSHSSVG | VPPCSPR | GGGRTRM | GAQLREL |
| APRPSEFR | GAQPHGM | VAGSTPE | GRLHPAH | AAAPLPM | VAGEVPW |
| APAPSEFR | HVSPADP | SSERGDQ | RDATVQA | AASPSEV | ATAPRSG |
| PGEDGATV | PVLNLPG | SSSAGTE | TISATAR | PPGCAAL | SVNPTGG |
| PPAPPSES | PRPQPSP | SGGARRL | VRSALGG | RNAPPTL | GLSPPTG |
| PANTHWPA | PYQAPPR | SGGARLL | SSPWLPR | ATPPPPC | SGIRRCR |
| PPQPPFPR | PVTRGIP | GGGARRL | GSQPPRE | GVAACPI | SVQCSAA |
| QPRRPGIA | NDSPDPV | AAPPLEV | SLRPAPS | RVAARPI | VSSSRSG |
| PAQAAPGI | SVRGAPP | SGDADLS | RLTRMFP | GVAARPT | SGIRLPG |
| HATAPRHR | PAHIPRS | GAHRSDT | AHGTNRP | VDTPTTR | NQHSAAG |
| AAAGTPEG | RGACRTR | TRVAAPS | AQMGSPA | VSHTSVV | GGVLAAG |
| QPSGPLAG | RGSPQNA | GTRLVPA | DRLSVPH | RTAPPFG | SGVVAVR |
| HSAPAPPA | SLPSPGP | STAAGAC | NASRRTW | VSHASVG | SGGGCGP |
| KHTPLMGT | GSYVQAG | FRLAARG | NASRPNH | YSARVPG | SGVATVR |
| RNNTTVA | RELRAGG | SNRPLLL | GPRTSAL | RTAPRTS | HVPPPDP |
| QARQDPT | AGRGYTY | IPMGAPR | DSAHPHR | GPAPLLR | APPSFGR |
| AKAPAES | AGRATPT | SPPGSAR | PPQQAGE | GPAHPAC | RWCPCRP |

Figure 3 (cont'):

| | | | | | |
|---|---|---|---|---|---|
| GDVLRRP | PTRAEHE | PQGRARA | TAGAPWS | TMASRHP | PSRSARR |
| NQHSAGP | PTRARAR | SATITSR | TRDLVPS | TMAPAPR | NSTPSTA |
| NQHSTAR | RDPPASS | SATATSR | KTGDAPP | TGSLTHP | RGVASNA |
| NAPGVPG | PAAPGPS | AQMGSSR | RPSGHVP | TRSPDPP | RSNVVSA |
| RHLAVAP | QTSITPT | VLPGSPR | MGAVAAP | RGARLST | RTHRPDG |
| NAPGVPP | YRTTGGS | ELPGSPR | IRPQPPP | SGARLTT | IIVGPPR |
| SSNGTPP | KRGLDAV | AQPGSPR | RRPLAND | GAPRPTT | SGGRTAC |
| VAGSTPT | KRGPDTV | NGAATRA | RDSHPHF | GKVVPYT | SVPVRQH |
| VIGVPAR | YRTLGRS | SSHALQR | DRSRLAS | PNRGGSL | RRAGLDP |
| NASSTVR | GADRGLV | AATTDGG | VPSRAAR | TGRSAGY | ALRSAVP |
| GLSPPHE | RADRDLV | HPAGIVR | ASRVPSE | AATTTGH | AATTSAY |
| DSASQPR | ALATGLV | KPGGRSP | GDPSYPQ | SQAGVLH | NDSGPRA |
| RTAPAPG | PHGPEAR | REPPSPR | TSSAPVP | RVATSPN | GFRGSGR |
| LAPVAVA | RADRGHV | ASPPPPR | LRVWGRR | RATTSPN | PALNPPP |
| VRRWRRR | LERHKSL | SAKAAIR | NLSRRRR | RRDDSPN | NAPSPSR |
| RCPWHGY | SGAHKSL | TTILAGR | NSRPPPP | GVVARPI | YSPGSPK |
| RHRRSDV | GPRTRCP | AAMNLGR | ARVASRR | RADPRSR | YSAGPPK |
| YAPTRCG | DPRTSVL | LRSRTLA | GAHRSDV | RSDRPSR | VRSHFGG |
| VAGQYPE | TGMPGRP | SSRTLAA | AASPSLR | GPGPSWR | KTGGPLR |
| SQETAGS | SGMPGLL | MGAVAGP | PTRGSLR | HSARCRP | VKSTRRC |
| HSATSGS | VHSPSTS | PRGTQAR | GAHRSGS | KTVGVPP | MTAASRQ |
| KRASTRR | AFRAFPD | PTRLPPR | GPVLQRS | TTIPRWP | SAKVGYP |
| NTGRASS | RAGYQAD | NAAPYPR | GARRSDS | IGPQLPP | AAVPLDV |
| NSGQASS | GVPRPTI | FNTRAPA | GASPVRL | GPSLTPP | MRATRAR |
| KQLHGGI | GAPQPTI | QTSIAPA | GRSPVRL | QTSITPP | VPPCPPA |
| GKGPRLR | ASGAFPD | NSAGTPA | DAHRSDS | PTSVRSA | APTSPWR |
| NVAPAPA | GAPRPTH | NSTGTPA | AKVVPNS | ASRGLRA | STSPSPQ |
| FPWGRR | SVGSSAR | LRNTGPR | PKVSPNS | GMPCYCR | ARASRLV |
| TPWPVAA | GQRAPVG | VSHGGPR | TNALPRA | NLDGRRA | VPHCSPA |
| NDPRRNR | LSRSSGG | FNTGPPA | MNALRGP | TRRWYAG | KRPQSSR |
| QLRRDLD | TRGTLRA | LIPGPPA | TERPPRP | PVTRATP | GGRCSSD |
| PTPALQD | RTSHRRR | QTVDHPP | SKVSTVA | VEVPACP | SNSPAMP |
| RRAPAPR | RTNHAVG | GPSPTPR | SKVYTVA | TYRLPAP | PNSPAML |
| RLDDTGL | RPARQLG | RRRSTPR | RSDTTVA | SPRSTLL | SNPPAML |
| VVRSVPS | LRVSGAR | GPSAYPR | PEQHHRR | REQRSRT | SNSPATL |
| RDVASVN | GATPPSR | GPSPYPR | FKPAAGA | RSNRGER | TVRGLRG |
| TGFAPTN | VTGTGTS | RRAPSTA | SKPATGA | NFRDCDA | AVATNGR |
| PTRLLPR | RDSHPFA | DSVHHR | YARASSA | PNLGRSA | RTSRAVG |
| NFRECER | RDSLPIR | DSVRPHR | NSAPRRR | PTGVPSP | TPSTGPL |
| NFRVCER | RDSHPHS | PGRPLTA | NPKPPAA | SVNAPAA | PLSRPEP |
| RHLGGIE | RVYATHS | VGAGLNR | GMRVTAA | LPASLPQ | TGRSTGT |
| GVRARGE | EQPMPSR | IGTGLNR | SRSPQFP | LSTGAAA | YSSGAPR |
| GFGSSGE | SSPFMPR | VGTGQNR | ASTRMFP | FKHRALR | RPRRPGI |
| WSGGLPE | PLVAASR | QQHLRQP | RRPPECS | APRSAST | SPAMPIC |
| GSQSPGK | TRGLSPR | LRQRGLE | SRSPRVP | QGRRQPQ | NGAATPP |
| WSGGSPE | SSPGPPR | GREGSGE | RNTHSLP | SLDPWRC | MTTTSRQ |
| GGTGTVK | PLSAPLA | YPADIRS | TGARTAP | RVSVVSP | PSGLSTR |
| REYRDGQ | PAERPHS | PHNKPVE | PVTRAVP | RVFRRST | VGVLRPV |
| GSTRDGQ | DRSGSAA | ASVSVRA | GDRATSP | LEGGGGR | RPGVLRP |
| SGRNAGK | AATTAGR | GDPSYAA | PVTARSP | RRHAGRR | GAQHRNV |
| RDGPPPR | AATATGR | GDLSYRS | RSGHPAP | NLKAAPP | NAPGAPG |
| HGFAPTK | ATTTTGA | SDPSYRS | TMASRTP | SATAPGR | PNAGSSP |
| ADLRPTK | PGTRSGA | RLNSRPA | KMAPRTP | RTRKNGG | SLDPPAL |

Figure 3 (cont'):

| | | | | | |
|---|---|---|---|---|---|
| REAWAGP | PPQLHGQ | TTPRPSV | SPASFPA | MNALPQA | AAPPPCP |
| RDGASPT | SSRGAPP | GNQAPRC | NAPGVLR | RNAHGLP | VVLDGLA |
| VAPTLSV | PRERSWP | GNRGPCC | HRVPADP | RTGRPPR | PRPCRHA |
| DDRRPAP | SVPLAST | GNHGPCC | HVSPPDP | AVVRLSP | VGAVAAR |
| FKPATGR | TQMGTPA | VSSCLQR | SPIRARP | QGPGDLP | NASPPNM |
| VAGRVPW | VQPAARA | HFDGGPG | WSGGSPR | TMAPRHP | SVRGGTP |
| PPLGCPR | TTTPRWP | ARAGRDR | AGGGVPP | GHLQGSH | DAPVVRR |
| INGGEEY | SIAGPPC | RDGSPAK | AVTTNGT | SLTPPLA | NSRGDPR |
| INGVKSK | ALSTSQA | RPPTAPP | RGGLQNA | SLDAPPA | NCGQALT |
| TFIGAVP | YAINRPA | NASRPEH | GQGRPPH | RPLGLLS | SPSAGQR |
| RTHRLTT | NGAHRLA | AVDHPPP | DDLHAGR | GVTGLLQ | AVVRSVP |
| RTRRPDD | RDGASPK | NATRPVP | PQPYLAK | GVGPPSS | TVRLAAR |
| GGSPVPT | RANSGPH | RPTGLPP | PHAPPGQ | RHSVPQS | KLARTVS |
| RSGRPGP | ALYGGPS | MNAPSAG | PRRPTGQ | TGMPRPP | GARPVRL |
| SRSASGR | NLGLGAK | NGTSVNR | ATHGIPQ | PLWWPRL | PQHDLGS |
| SRTRVGQ | NSAGDPP | WHRPHPV | AQYGAAV | KTGEPLP | DPRATSW |
| SDSRTPC | LDDRRPR | LASPPTQ | AQYTRCC | GPSFTPP | KPHPLMG |
| NGAPLSR | NATGRPG | WHRPHPS | YRTTGHV | GGSPPYP | GGGRSLS |
| PRDDLAE | SGVAAVG | WHCPHPT | GPRASVL | GPDAAAL | GDLHARK |
| EEPPTAR | DGGGRPR | KAESLYR | ASGRSPD | ASTGCGR | NDLHARK |
| NATPAGP | PPTDSLR | KGGVAQP | RCAAAHH | NLKPPHR | DDRTDAR |
| RTNSGPR | AGAPSCA | YSAPPLR | TGSAWPP | SRSPPPF | RTAASTG |
| NRPASDQ | SPRPTLV | CGHASTV | TRGTVAA | SRTTSHA | HLLLPPS |
| NRPPPDK | TELGRWP | AASPLRG | PHQPRRR | SSTRPRG | IRPSVPR |
| GSNGPPG | RDSPVPD | RNRPPPT | GRAHAVS | RGPLPHY | KLAQIVS |
| ACCSGGY | GAPPVRL | IDSYDSI | TRDLSPS | GPGPHSC | AARVNPS |
| APNLTGP | GTVQAAE | DSARAPG | SSLSSHS | SPASFPT | PTDPRRT |
| SRSPTFP | GLSPPRG | DTGTHWA | IVNAPLA | RFLSSLQ | HHPRGPP |
| RYQGSGL | GRSDRSD | DTGTMGV | IVSAPLA | QRPPSLA | CTPAHPW |
| GVGSAVR | GRWASST | SSEGEPR | IASAPTR | STSPSPP | NGAPTAR |
| QQSRPSA | RARSRSR | SRDRLSS | KGPPTAR | RAWAFAE | HWPQLPP |
| TVPLRAA | QPGARRQ | SRDRPSQ | PEGRASG | LAGAGAP | TAGVPA |
| SRSPTFR | SSSAGDQ | WLSPALR | PLAGIVR | RCDGAFG | SVRGHP |
| PSWRSCA | PQPTWPR | TVAPPPL | PPLGLSA | GSRDSRD | PSSTSP |
| SVGLGVR | AVNSGPR | SGGAEPA | AAVNRGP | TSHPPPA | PLSAPL |
| SVGRGVK | ARADSPS | AARPPRP | MGAVVAR | NDSRTPV | ASQRAH |
| SVGLGDK | PVLNPSP | NAPSTRG | GAHSTPP | RPRRLVR | DAPRVR |
| QPALCGP | AAPSPIP | AVSGRPG | VSLGDPR | ARSIHSG | NLKPPR |
| TMSLTHP | PTHIPRI | SQETAGW | RWFAPLP | PTPHPSQ | NSAGPR |
| GAENWTH | TPHPPPL | GAQLRNV | MGAVATR | VRSHFSS | RARSNA |
| AHQGSLR | LPHRARP | RSRCRGG | LPCYGRP | SIAGPPV | GARSNT |
| NRPASDE | PKDPPLP | KGRARRY | GVGPCRP | SPRRRPA | ASPPHR |
| GAPAQEC | ATKARGL | INGVEEY | GRLAQPS | IVSAPTS | SNRPAA |
| LRVSLPG | SGGGTAS | AGRGSTW | RPRQQCQ | ASNVPPV | GPRSNA |
| HPVDIRE | SGGRHGV | ATHSSGG | AHSGQSP | RPGRCHS | |
| RVRWPVP | DAPRRPP | RARACPR | PAERPPP | RPPCSPA | |
| LGRSSGS | LPPGSAR | SPALLPT | PQRGGSL | AAPPPLP | |

Figure 4:

| Variants identified in whole retina | Variants identified in rods | Variants identified in cones |
|---|---|---|
| LRGDNPQ | RGSDPPR | NGRPTSS |
| VSPTNGR | RGSHPNI | RGSGAAY |
| LRGDNP | ERRLRGS | AVTTNGR |
| RGSGAGA | RGSLQNA | RGSLQNA |
| TRGDGAQ | | GFRGSGL |
| | | HKSARGD |
| | | AVTANGR |
| | | RGSGSWRG |
| | | RGSPQNA |
| | | SSERGDQ |
| | | RGSGAAC |
| | | RGSGTAY |
| | | PTRGSLR |
| | | GFRGSGR |
| | | AVATNGR |
| | | AGRGSTW |
| | | NSRGDPR |

Figure 5:

| Peptide | # of NGS reads in DNA from whole retina | # of NGS reads in DNA MAC-sorted rods | # of NGS reads in DNA from FAC-sorted cones |
|---|---|---|---|
| GAHRSDS | 12 | 0 | 333 |
| NSRPAAA | 12 | 0 | 43 |
| GLSPPTR | 1 | 0 | 37 |
| SSPGLPR | 1 | 0 | 37 |
| NSTSVNR | 8 | 0 | 32 |
| RGSLQNA | 0 | 2 | 25 |
| VSSSLQR | 1 | 0 | 21 |
| PNQAPPR | 1 | 0 | 17 |
| RANQTSS | 30 | 332 | 0 |
| HSARTDS | 9 | 141 | 0 |
| NNPTPSR | 1 | 137 | 0 |
| SQNDSRS | 67 | 88 | 0 |

SEQUENCE LISTING

<160> NUMBER OF SEQ ID NOS: 23

<210> SEQ ID NO 1
<211> LENGTH: 735
<212> TYPE: PRT
<213> ORGANISM: adeno-associated virus 2

<400> SEQUENCE: 1

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
        130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415
```

```
Asp Val Pro Phe His Ser Ser Tyr Ala His Ser Gln Ser Leu Asp Arg
             420                 425                 430

Leu Met Asn Pro Leu Ile Asp Gln Tyr Leu Tyr Leu Ser Arg Thr
         435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
             485                 490                 495

Asn Ser Glu Tyr Ser Trp Thr Gly Ala Thr Lys Tyr His Leu Asn Gly
         500                 505                 510

Arg Asp Ser Leu Val Asn Pro Gly Pro Ala Met Ala Ser His Lys Asp
515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                 565                 570                 575

Gly Ser Val Ser Thr Asn Leu Gln Arg Gly Asn Arg Gln Ala Ala Thr
             580                 585                 590

Ala Asp Val Asn Thr Gln Gly Val Leu Pro Gly Met Val Trp Gln Asp
         595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                 645                 650                 655

Pro Ser Thr Thr Phe Ser Ala Ala Lys Phe Ala Ser Phe Ile Thr Gln
             660                 665                 670

Tyr Ser Thr Gly Gln Val Ser Val Glu Ile Glu Trp Glu Leu Gln Lys
         675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                 725                 730                 735

<210> SEQ ID NO 2
<211> LENGTH: 54
<212> TYPE: DNA
<213> ORGANISM: Artificial Sequence
<220> FEATURE:
<223> OTHER INFORMATION: bottom sequence
<220> FEATURE:
<221> NAME/KEY: misc_feature
<222> LOCATION: (13)..(13)
<223> OTHER INFORMATION: n is A or C or G
<220> FEATURE:
<221> NAME/KEY: misc_feature
<222> LOCATION: (14)..(15)
<223> OTHER INFORMATION: n is A or C or G or T
<220> FEATURE:
<221> NAME/KEY: misc_feature
<222> LOCATION: (16)..(16)
<223> OTHER INFORMATION: n is A or C or G
```

```
<220> FEATURE:
<221> NAME/KEY: misc_feature
<222> LOCATION: (17)..(18)
<223> OTHER INFORMATION: n is A or C or G or T
<220> FEATURE:
<221> NAME/KEY: misc_feature
<222> LOCATION: (19)..(19)
<223> OTHER INFORMATION: n is A or C or G
<220> FEATURE:
<221> NAME/KEY: misc_feature
<222> LOCATION: (20)..(21)
<223> OTHER INFORMATION: n is A or C or G or T
<220> FEATURE:
<221> NAME/KEY: misc_feature
<222> LOCATION: (22)..(22)
<223> OTHER INFORMATION: n is A or C or G
<220> FEATURE:
<221> NAME/KEY: misc_feature
<222> LOCATION: (23)..(24)
<223> OTHER INFORMATION: n is A or C or G or T
<220> FEATURE:
<221> NAME/KEY: misc_feature
<222> LOCATION: (25)..(25)
<223> OTHER INFORMATION: n is A or C or G
<220> FEATURE:
<221> NAME/KEY: misc_feature
<222> LOCATION: (26)..(27)
<223> OTHER INFORMATION: n is A or C or G or T
<220> FEATURE:
<221> NAME/KEY: misc_feature
<222> LOCATION: (28)..(28)
<223> OTHER INFORMATION: n is A or C or G
<220> FEATURE:
<221> NAME/KEY: misc_feature
<222> LOCATION: (29)..(30)
<223> OTHER INFORMATION: n is A or C or G or T
<220> FEATURE:
<221> NAME/KEY: misc_feature
<222> LOCATION: (31)..(31)
<223> OTHER INFORMATION: n is A or C or G
<220> FEATURE:
<221> NAME/KEY: misc_feature
<222> LOCATION: (32)..(33)
<223> OTHER INFORMATION: n is A or C or G or T

<400> SEQUENCE: 2
ttggcgcgcc gcnnnnnnnn nnnnnnnnnn nnnggcggcc gcttttttcc ttga          54

<210> SEQ ID NO 3
<211> LENGTH: 15
<212> TYPE: DNA
<213> ORGANISM: Artificial Sequence
<220> FEATURE:
<223> OTHER INFORMATION: primer

<400> SEQUENCE: 3
ctcaaggaaa aaagc                                                     15

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
atgtccgtcc gtgtgtgg                                                  18

<210> SEQ ID NO 5
<211> LENGTH: 22
<212> TYPE: DNA
<213> ORGANISM: Artificial Sequence
<220> FEATURE:
```

```
<223> OTHER INFORMATION: primer

<400> SEQUENCE: 5
gtatctacca acctccagag ag                                              22

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gtgttgacat ctgcggtagc                                                 20

<210> SEQ ID NO 7
<211> LENGTH: 35
<212> TYPE: DNA
<213> ORGANISM: Artificial Sequence
<220> FEATURE:
<223> OTHER INFORMATION: single strand DNA oligo
<220> FEATURE:
<221> NAME/KEY: misc_feature
<222> LOCATION: (11)..(31)
<223> OTHER INFORMATION: N = A or C or G or T

<400> SEQUENCE: 7
cgcggccgca nnnnnnnnnn nnnnnnnnnn ngccg                                35

<210> SEQ ID NO 8
<211> LENGTH: 35
<212> TYPE: DNA
<213> ORGANISM: Artificial Sequence
<220> FEATURE:
<223> OTHER INFORMATION: single strand DNA oligo
<220> FEATURE:
<221> NAME/KEY: misc_feature
<222> LOCATION: (9)..(29)
<223> OTHER INFORMATION: N = A or C or G or T

<400> SEQUENCE: 8
cgcgcggcnn nnnnnnnnn nnnnnnnnnt gcggc                                 35

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ctttgggaag caaggctcag                                                 20

<210> SEQ ID NO 10
<211> LENGTH: 7
<212> TYPE: PRT
<213> ORGANISM: Artificial Sequence
<220> FEATURE:
<223> OTHER INFORMATION: insertion sequence

<400> SEQUENCE: 10

Gly Leu Ser Pro Pro Thr Arg
1               5

<210> SEQ ID NO 11
<211> LENGTH: 7
<212> TYPE: PRT
```

```
<213> ORGANISM: Artificial Sequence
<220> FEATURE:
<223> OTHER INFORMATION: insertion sequence

<400> SEQUENCE: 11

Ser Ser Pro Gly Leu Pro Arg
1               5

<210> SEQ ID NO 12
<211> LENGTH: 7
<212> TYPE: PRT
<213> ORGANISM: Artificial Sequence
<220> FEATURE:
<223> OTHER INFORMATION: insertion sequence

<400> SEQUENCE: 12

Asn Ser Thr Ser Val Asn Arg
1               5

<210> SEQ ID NO 13
<211> LENGTH: 7
<212> TYPE: PRT
<213> ORGANISM: Artificial Sequence
<220> FEATURE:
<223> OTHER INFORMATION: insertion sequence

<400> SEQUENCE: 13

Val Ser Ser Ser Leu Gln Arg
1               5

<210> SEQ ID NO 14
<211> LENGTH: 7
<212> TYPE: PRT
<213> ORGANISM: Artificial Sequence
<220> FEATURE:
<223> OTHER INFORMATION: insertion sequence

<400> SEQUENCE: 14

Pro Asn Gln Ala Pro Pro Arg
1               5

<210> SEQ ID NO 15
<211> LENGTH: 7
<212> TYPE: PRT
<213> ORGANISM: Artificial Sequence
<220> FEATURE:
<223> OTHER INFORMATION: insertion sequence

<400> SEQUENCE: 15

Asn Asn Pro Thr Pro Ser Arg
1               5

<210> SEQ ID NO 16
<211> LENGTH: 7
<212> TYPE: PRT
<213> ORGANISM: Artificial Sequence
<220> FEATURE:
<223> OTHER INFORMATION: insertion sequence

<400> SEQUENCE: 16

Gly Ala His Arg Ser Asp Ser
1               5

<210> SEQ ID NO 17
<211> LENGTH: 7
<212> TYPE: PRT
<213> ORGANISM: Artificial Sequence
```

```
<220> FEATURE:
<223> OTHER INFORMATION: insertion sequence

<400> SEQUENCE: 17

Arg Ala Asn Gln Thr Ser Ser
1               5

<210> SEQ ID NO 18
<211> LENGTH: 7
<212> TYPE: PRT
<213> ORGANISM: Artificial Sequence
<220> FEATURE:
<223> OTHER INFORMATION: insertion sequence

<400> SEQUENCE: 18

His Ser Ala Arg Thr Asp Ser
1               5

<210> SEQ ID NO 19
<211> LENGTH: 7
<212> TYPE: PRT
<213> ORGANISM: Artificial Sequence
<220> FEATURE:
<223> OTHER INFORMATION: insertion sequence

<400> SEQUENCE: 19

Ser Gln Asn Asp Ser Arg Ser
1               5

<210> SEQ ID NO 20
<211> LENGTH: 7
<212> TYPE: PRT
<213> ORGANISM: Artificial Sequence
<220> FEATURE:
<223> OTHER INFORMATION: insertion sequence

<400> SEQUENCE: 20

Asn Ser Arg Pro Ala Ala Ala
1               5

<210> SEQ ID NO 21
<211> LENGTH: 7
<212> TYPE: PRT
<213> ORGANISM: Artificial Sequence
<220> FEATURE:
<223> OTHER INFORMATION: motif

<400> SEQUENCE: 21

Arg Gly Ser Leu Gln Asn Ala
1               5

<210> SEQ ID NO 22
<211> LENGTH: 4
<212> TYPE: PRT
<213> ORGANISM: Artificial Sequence
<220> FEATURE:
<223> OTHER INFORMATION: motif

<400> SEQUENCE: 22

Gly Asn Arg Gln
1

<210> SEQ ID NO 23
<211> LENGTH: 9
<212> TYPE: PRT
<213> ORGANISM: Artificial Sequence
<220> FEATURE:
```

```
<223> OTHER INFORMATION: 7m8

<400> SEQUENCE: 23

Leu Ala Leu Gly Glu Thr Thr Arg Pro
1               5
```

AAV VECTORS

CROSS-REFERENCE TO RELATED APPLICATIONS

This application is a national phase entry pursuant to 35 U.S.C. § 371 of International Application No. PCT/EP2018/078175, filed Oct. 16, 2018, which claims priority to European Application No. EP 17196567.6 filed Oct. 16, 2017, the entire contents of which are incorporated by reference herein for all purposes.

FIELD OF THE INVENTION

The present invention relates to an adeno-associated virus (AAV), comprising an insertion of at least 6-8 amino acids between the positions corresponding to position 587 and 588 of SEQ ID NO: 1. Also envisioned are AAVs of the present invention for use as a medicament and pharmaceutical compositions comprising the AAV of the present invention. Further, the present invention relates to an in vitro use of AAV of the present invention for transduction of the nucleus of retinal cells. Also concerned is a method for screening an insertion sequence as well as a peptide obtainable by the method for screening. Also contemplated are kits comprising the AAV of the present invention.

DESCRIPTION

Recombinant adeno-associated virus (AAV) vectors have proven to be a very suitable delivery system for efficient and long-term transfer of genes into retinal cells (Boye et al. (2013) "A comprehensive review of retinal gene therapy" Molecular therapy, 21 (2013) 509-519 and Trapani et al. (2014) "Vector platforms for gene therapy of inherited retinopathies" Prog. Retin Eye Res.). AAVs are non-pathogenic viruses that belong to the Parvovirus family and Dependovirus genus and replicate only in the presence of adeno-, papilloma- or herpes-viruses (Nathwani et al. (2014) "Long-term safety and efficacy of factor IX gene therapy in hemophilia B" N. Engl. J. Med., 371 (2014) 1994-2004) and possess an approx. 5 kb single-stranded DNA genome (Trapani et al. (2014) "Vector platforms for gene therapy of inherited retinopathies" Prog. Retin Eye Res.).

AAVs have been tested extensively for safety and long-term expression of transgenes in large animal models, non-human primates and a number of trials in humans (MacLaren et al. (2014) "Retinal gene therapy in patients with choroideremia: initial findings from a phase 1/2 clinical trial" Lancet 383, 1129-1137, Maguire et al. (2008) "Safety and efficacy of gene transfer for Leber's congenital amaurosis" N. Engl. J. Med., 358 2240-2248, Simonelli et al. (2010) "Gene therapy for Leber's congenital amaurosis is safe and effective through 1.5 years after vector administration" Molecular therapy: the journal of the American Society of Gene Therapy 18, 643-650, Nathwani et al. (2014) "Long-term safety and efficacy of factor IX gene therapy in hemophilia B" N. Engl. J. Med. 371, 1994-2004).

AAVs are the preferred gene transfer vectors for gene supplementation therapy (also gene augmentation therapy). Gene supplementation therapy is an attractive approach for the treatment of inherited diseases that aims at restoration of insufficient or lacking gene function caused by a pathogenic mutation. The goal is to restore regular physiological function of the affected cell type and/or to inhibit or delay the degenerative processes by supplementation of a gene function.

Gene therapy aims at restoration of insufficient or lacking gene function resulting from a pathogenic mutation. This approach is particularly attractive for the treatment of recessively inherited diseases where aberrant transcripts or proteins are not expected to interfere with the treatment. The goal is to stop or prevent the degenerative process and to restore regular physiological function of the affected cell type or tissue by supplementation of the normal gene function in sufficient amounts and at the proper location.

Although, AAVs show some degree of spreading within tissues and organisms (Le Guiner et al. (2011) "Biodistribution and shedding of AAV vectors" Methods in molecular biology 807, 339-359) they generally need to be administered locally in most therapeutic approaches and in particular for ocular gene therapy. For the transduction of photoreceptors or retinal pigment epithelium (RPE) cells AAV particles are administered to the subretinal space (i.e. a cavity that is formed after injection of liquids between the RPE and the photoreceptors) (Mühlfriedel et al. (2013) "Optimized technique for subretinal injections in mice" Methods in molecular biology 935, 343-349, Ochakovski et al. (2017) "Retinal Gene Therapy: Surgical Vector Delivery in the Translation to Clinical Trials." Front Neurosci. 11:174).

Structurally, AAVs are small (25 nm), non-enveloped viruses with an icosahedral capsid. Naturally occurring or engineered AAV variants (also AAV serotypes) that differ in the composition and structure of their capsid (cap) protein have varying tropism, i.e. ability to transduce different (retinal) cell types (Boye et al. (2013) "A comprehensive review of retinal gene therapy" Molecular therapy 21 509-519 and Trapani et al. (2014) "Vector platforms for gene therapy of inherited retinopathies" Prog Retin Eye Res). When combined with ubiquitously active promoters this tropism defines the site of gene expression. Whereas in combination with cell-type specific promoters the degree of site-specificity (i.e. transgene expression only in rod or cone photoreceptors) is defined by the combination of both, the tropism of the AAV serotype and the specificity of the promoter (Schön et al. (2015) "Retinal gene delivery by adeno-associated virus (AAV) vectors: Strategies and applications" European journal of pharmaceutics and biopharmaceutics). Administration of AAVs into the eye's vitreous results in transduction of cells within the inner retina, mainly of ganglion cells and Müller glial cells (Trapani et al. (2014) "Vector platforms for gene therapy of inherited retinopathies" Prog. Retin Eye Res.).

None of the naturally occurring AAV serotypes is capable of transducing photoreceptors when administered intravitreally because of the physical barrier at the inner limiting membrane (ILM) or the lack of appropriate receptors at the ILM.

A prerequisite for successful gene therapy approaches is the efficient and long lasting transgene expression in the target cells with only minimal off-target expression and lowest possible adverse effects. Although, the available AAV vectors constitute valuable gene delivery tools there is still a strong demand for the development of improved AAVs.

For targeting photoreceptors AAVs need to be administered into the subretinal space. This very invasive surgical procedure results in detachment of the retina from the RPE. Retinal detachment usually is temporal and the retina reattaches without any severe or long-term deleterious effects on retinal function and morphology. However, the risk for collateral damage due to the subretinal injection might be increased in the degenerated retina and/or if the detachment involves the foveo-macular region. Therefore, improved AAV vectors are needed, in particular regarding the bioavailability, route of delivery and the target cell specificity.

Thus, there still exists a need for the development of further improved AAV vectors. Here, we describe novel AAV that evolved from an in vivo selection with improved characteristics for gene transfer into retinal cells and especially photoreceptor cells.

The present invention complies with this need as described herein and as described in the Examples, Figures and claims.

The present invention relates to an adeno-associated virus (AAV), the AAV comprising an insertion of at least 6-8 amino acids between the positions corresponding to position 587 and 588 of SEQ ID NO: 1; wherein the insertion sequence has from the N-terminus to the C-terminus the formula I:

$$X_{1A}\text{-}X_{1B}\text{-}X_2\text{-}X_3\text{-}X_4\text{-}X_5\text{-}X_6\text{-}X_7 \qquad \text{(formula I)}$$

wherein $X_5$ is selected from P (Pro), L (Leu) and V (Val);
wherein $X_7$ is R (Arg);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present, or
wherein $X_5$ is selected from S (Ser) and T (Thr);
wherein $X_7$ is S (Ser);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present, or
wherein $X_5$ is selected from A (Ala) and Q (Gln);
wherein $X_7$ is A (Ala);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present,
wherein viral AAV DNA is present in mouse retinal nuclear extracts after 24 hours,
when the AAV is administered intravenously into the tail vein of a C57-Bl6J mouse, and
wherein viral AAV DNA is present in MAC-sorted rods using anti-CD73-coated magnetic beads and/or FACS-sorted cones, wherein the cones express eGFP and are FACS sorted based on their eGFP expression, 24 hours after administration, when the AAV is administered intravenously into the tail vein of a C57-Bl6J mouse for rod sorting and into the tail vein of RG-eGFP mice line R685933 for cone sorting.

Furthermore, the present invention relates to an AAV of the present invention for use as a medicament.

In addition, the present invention relates to an AAV of the present invention for use in treating a photoreceptor cell disease.

The present invention further concerns pharmaceutical composition comprising an AAV of the present invention.

Also, the present invention relates to an in vitro use of an AAV of the present invention for transduction of the nucleus of retinal cells.

Furthermore, the present invention relates to a method for screening an insertion sequence, the method comprising
i) intravenously administering an AAV library, wherein each AAV comprises an insertion sequence, into a subject;
ii) isolating viral AAV DNA from retinal nuclear extracts;
iii) subcloning the isolated viral AAV DNA into a second AAV library;
iv) intravenously administering the second AAV library as obtained in step iii) into a subject;
v) isolating viral AAV DNA from rod or cone photoreceptors;
vi) determining the sequence of the insertion sequence, thereby obtaining the insertion sequence.

The present invention additionally relates to a peptide (insertion sequence) obtainable by the screening method of the present invention.

The present invention also relates to a kit comprising an AAV the present invention.

THE FIGURES SHOW

FIG. 1: Peptide insertions from whole retina
The following novel AAVs with the listed peptide insertions in position 587 of AAV2VP1 conferred the ability to target cells of the retina and transfer their genome into the nucleus of retinal cells within 24 hours after intravenous delivery could be identified (only variants with 2 or more NGS reads are listed, the variants with more than 20 NGS reads are marked in bold letters).

FIG. 2: Peptide insertions from rod photoreceptors
In addition, the following novel AAVs with the listed peptide insertions in position 587 of AAV2 VP1 conferred the ability to target rod photoreceptors within 24 hours after intravenous delivery could be identified (only peptides with 2 or more NGS reads are listed, the variants with more than 20 NGS reads are marked in bold letters).

FIG. 3: Peptide insertions from cone photoreceptors
Finally, the following novel AAVs with the listed peptide insertions in position 587 of AAV2 VP1 conferred the ability to target cone photoreceptors within 24 hours after intravenous delivery could be identified (only peptides with 2 or more NGS reads are listed, the variants with more than 20 NGS reads are marked in bold letters).

FIG. 4: Identified peptide insertions with RGD, RGS or NGR motifs.
Some of the identified AAVs contained putative integrin binding motifs like RGD, RGS or NGR in their insertion sequence. These insertions sequences are summarized FIG. 4.

FIG. 5: Peptide insertions identified in more than one tissue/cell population. The number of NGS reads in each experiment is shown. Several AAVs were detected in more than one experiment. These overlapping AAVs comprising the indicated insertion sequences with the respective numbers of NGS reads are summarized in FIG. 5.

FIG. 6: Representative in vivo confocal scanning laser ophthalmoscopy (cSLO) images showing eGFP autofluorescence in the fundus of 10 week old C57-BL6J mice 2 weeks after a single intravitreal injection of 1 μl (containing approximately 2×10E9 vector genomes) of viral suspension of AAV-sc-CMV-eGFP packaged with one of the novel AAV2 variants (peptide insertion sequences are given on top of each image). Strong eGFP autofluorescence (grey) in multiple retinal cell types and in a large area of the retina was observed.

Figure 7:
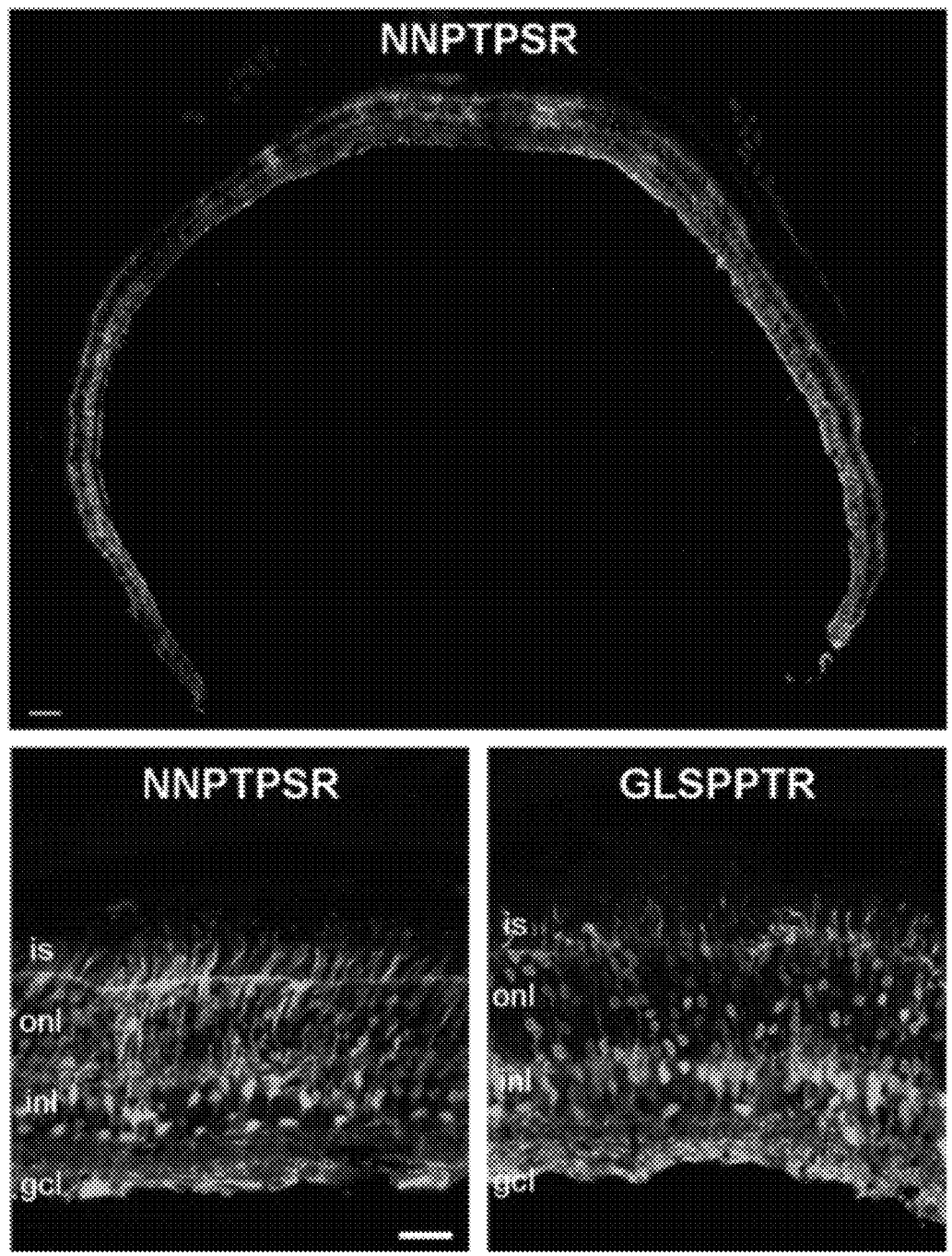

FIG. 7: Representative confocal scanning microscopy images showing eGFP fluorescence in retinal cross sections from 11 week old C57-BL6J mice 3 weeks after a single intravitreal injection of 1 μl (containing approximately 2×10E9 vector genomes) of viral suspension of AAV-sc-CMV-eGFP packaged with one of the novel AAV2 (peptide insertion sequences are given on top of each image column). Strong eGFP fluorescence (grey) in multiple retinal cell types and layers and across the whole area of the retinal cross-section was observed for variants "NNPTPSR" (see overview image in the top panel and close-up view in the lower left panel) and "GLSPPTR" (only close-up view is shown in the lower right panel). In particular, many photoreceptor inner segments (is) and cell bodies within the outer nuclear layer (onl) were eGFP positive, inl, innernuclear layer; gel, ganglion cell layer. The scale bar marks 100 µm in the top panel and 25 µm in the lower panels.

Figure 8:
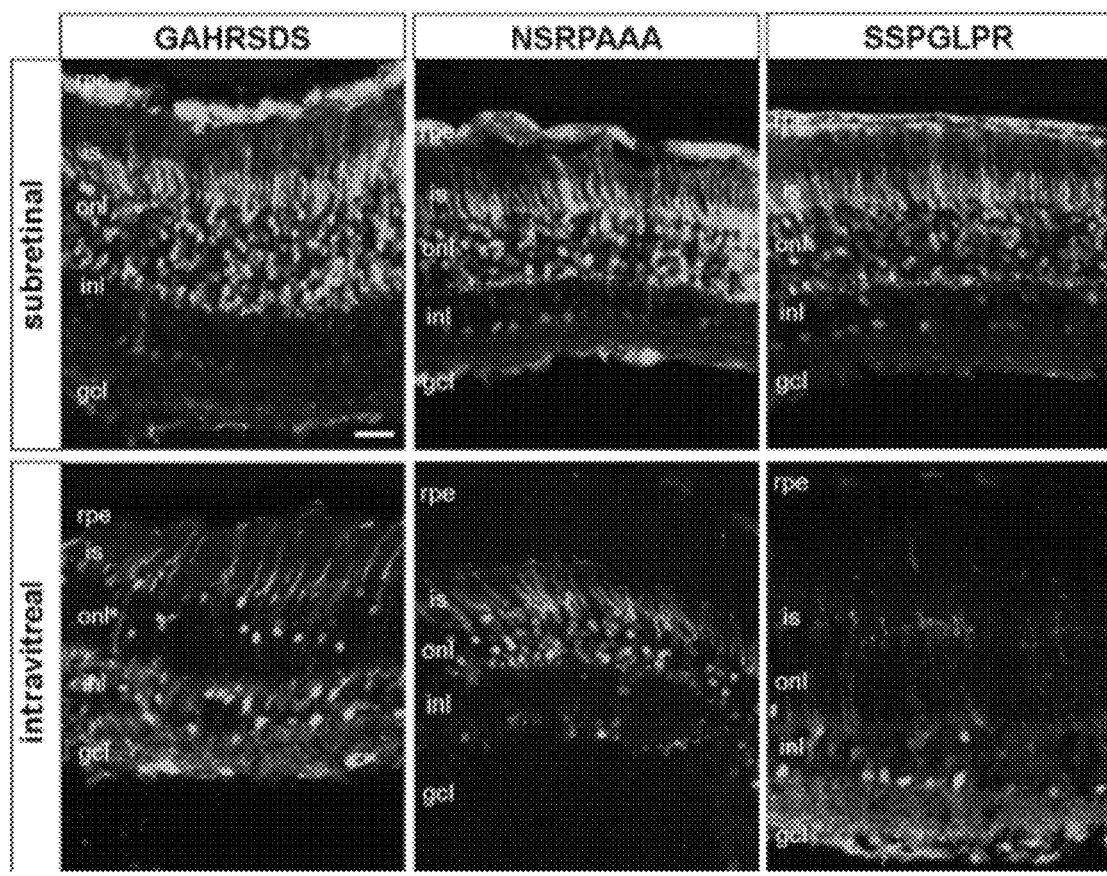

FIG. 8: Representative confocal scanning microscopy images showing eGFP fluorescence in retinal cross sections from 11 week old C57-BL6J mice 3 weeks after a single subretinal (upper panels) or intravitreal (lower panels) injection of 1 µl (containing approximately 2×10E9 vector genomes) of viral suspension of AAV-sc-CMV-eGFP packaged with one of the novel AAV2 (peptide insertion sequences are given on top of each image column). Strong eGFP fluorescence (grey) in multiple retinal cell types and layers was observed. In particular, many photoreceptor inner segments (is) and cell bodies within the outer nuclear layer (onl) were eGFP positive. After subretinal injections strong eGFP fluorescence was also observed in retinal pigment epithelial cells (rpe). inl, inner nuclear layer; gel, ganglion cell layer. The scale bar marks 25 µm.

Figure 9:
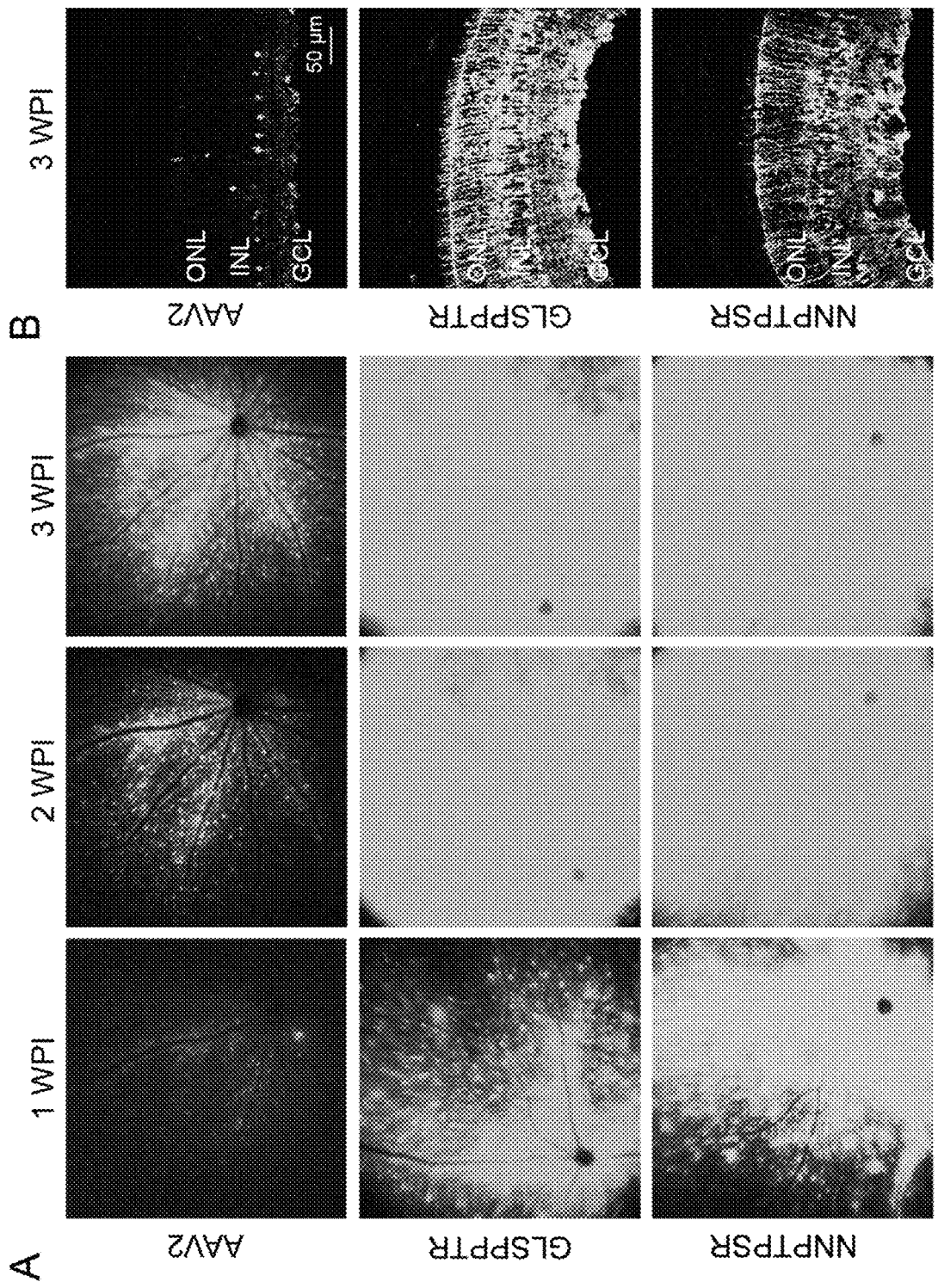

FIG. 9: (A) Representative in vivo confocal scanning laser ophthalmoscopy (cSLO) images showing eGFP autofluorescence in the fundus of 2 month old C57-BL6J mice at 1, 2 and 3 weeks after a single intravitreal injection (WPI) of 1 µl (containing approximately 2×10E9 vector genomes) of viral suspension of AAV-sc-CMV-eGFP packaged with one of the novel AAV variants (GLSPPTR or NNPTPSR; peptide insertion sequences are given on top of each image). Strong eGFP autofluorescence (grey) in multiple retinal cell types and in a large area of the retina was observed. All images were collected with the same laser and detector settings. (B) Representative confocal scanning microscopy images showing the immunosignal obtained with anti-eGFP antibody (grey) in retinal cross sections from 2 month old C57-BL6J mice at 3 weeks after a single intravitreal injection (WPI) of 1 µl (containing approximately 2×10E9 vector genomes) of viral suspension of AAV-sc-CMV-eGFP packaged with AAV2 or one of the novel AAV variants (GLSPPTR or NNPTPSR; peptide insertion sequences are given on top of each image column). Strong eGFP immunosignal (grey) in multiple retinal cell types and layers was observed for the novel variants GLSPPTR and NNPTPSR, respectively. In contrast, AAV2 resulted in weaker labeling of sparse cells. All images were collected with the same laser and detector settings. In particular, many photoreceptor cell bodies within the outer nuclear layer (onl) were eGFP positive. inl, inner nuclear layer; gcl, ganglion cell layer.

Figure 10:
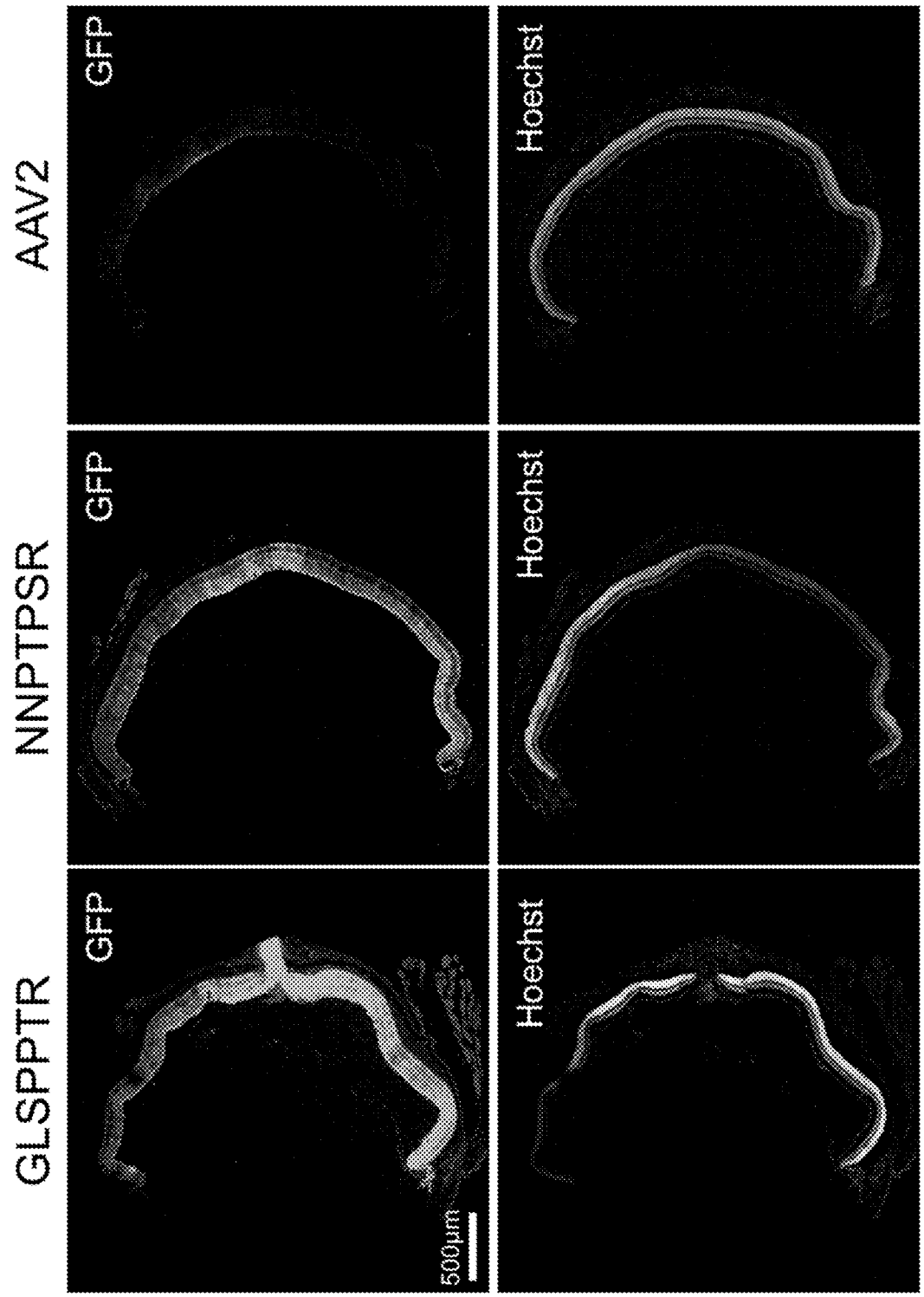

FIG. 10: Representative confocal scanning microscopy overview images showing the immunosignal obtained with anti-eGFP antibody (upper panels, grey) in retinal cross sections from 2 month old C57-BL6J mice at 3 weeks after a single intravitreal injection (WPI) of 1 µl(containing approximately 2×10E9 vector genomes) of viral suspension of AAV-sc-CMV-eGFP packaged with AAV2 or one of the novel AAV variants (GLSPPTR or NNPTPSR; peptide insertion sequences are given on top of each image column). Strong eGFP immunosignal (grey) in multiple retinal cell types and layers and throughout the retinal crosssection was observed for the novel variants GLSPPTR and NNPTPSR, respectively. In contrast, AAV2 resulted in weaker labeling in a smaller area of the retina. All images were collected with the same laser and detector settings. Corresponding Hoechst 33342 nuclear cell staining (grey) images are shown below each of the eGFP images.

Figure 11:
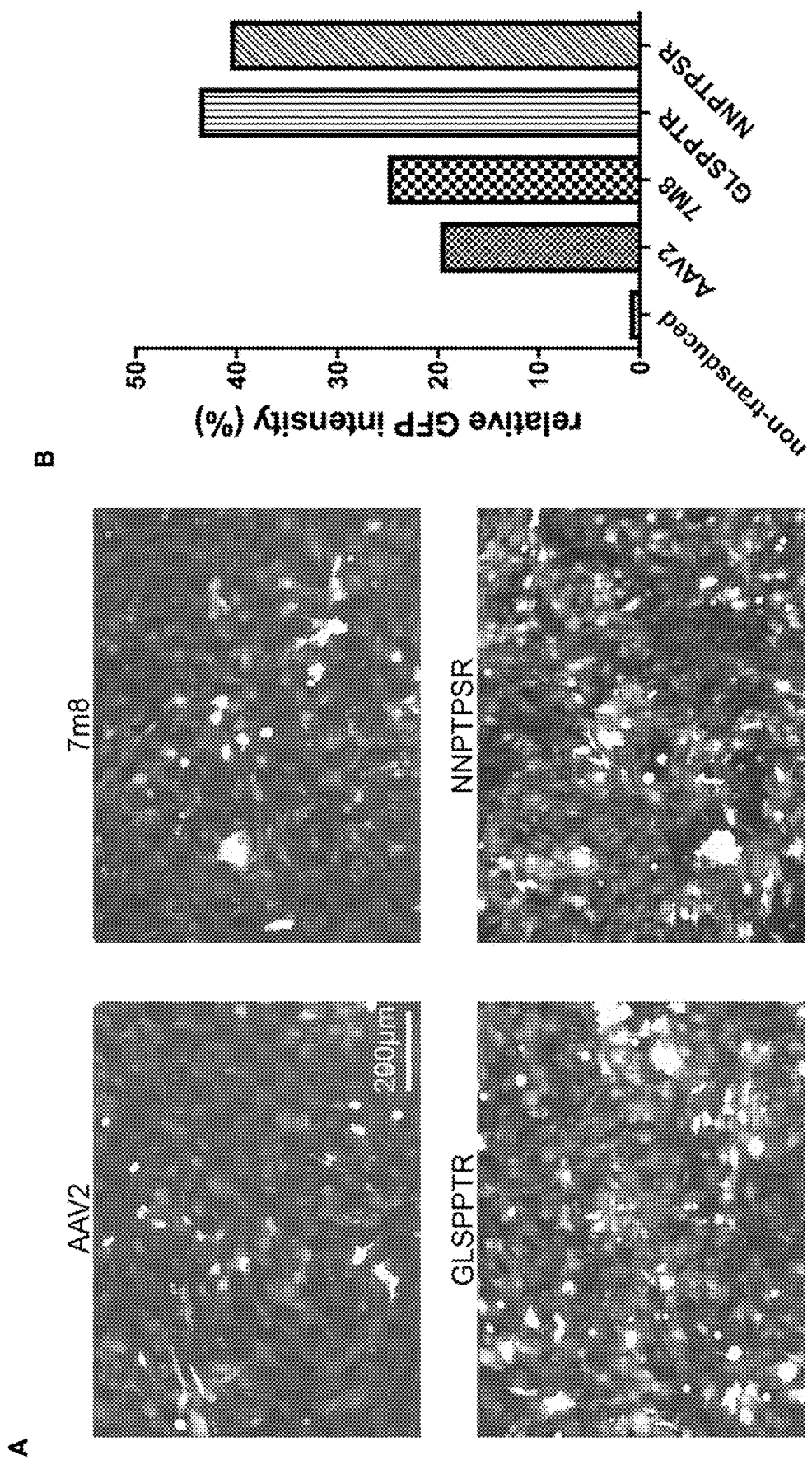

FIG. 11: Transduction efficiencies of AAV vectors in 661w cells. (A) Representative epifluorescence images from 661w cell cultures at 48 hours after transduction with MOI 100,000 of AAV-sc-CMV-eGFP packaged with AAV2, 7m8, or one of the novel AAV variants (GLSPPTR or NNPTPSR; peptide insertion sequences are given on top of each image column). (B) Graph showing the % relative eGFP intensity as measured with FACS in non-transduced 661w cell cultures and in 661w cell cultures at 48 hours after transduction with MOI 100,000 of AAV-sc-CMV-eGFP packaged with AAV2, 7m8, or one of the novel AAV variants (GLSPPTR or NNPTPSR; peptide insertion sequences are given on top of each image column).

Figure 12:
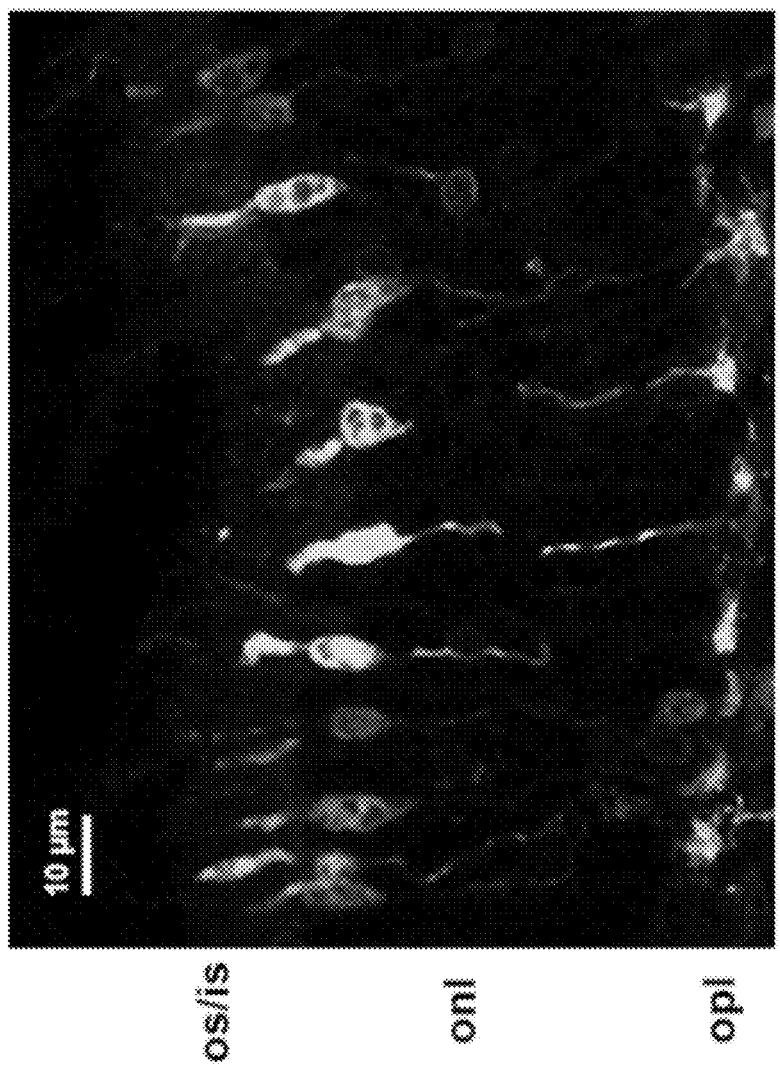

FIG. 12: Representative confocal scanning microscopy images showing cone photoreceptor expression of eGFP on retinal cross sections from 10 week old C57-BL6J mice 6 weeks after a single intravitreal injection of 1 µl (containing approximately 2×10E9 vector genomes) of viral suspension of ss-mSWS-eGFP packaged with the novel AAV2 "GLSPPTR" capsid. AAV-ss-mSWS-eGFP drives expression of eGFP under control of the mouse S opsin promoter. Strong anti-eGFP immunosignal (grey) in cone photoreceptors was observed. Quantification of double-labeling with the cone marker cone arrestin revealed that 78.7±3.1% (n=4) of cone arrestin-positive cones were positive for eGFP. OS/IS, outer and inner segments. ONL, outer nuclear layer. INL, inner nuclear layer. OPL, outer plexiform layer.

Figure 13:
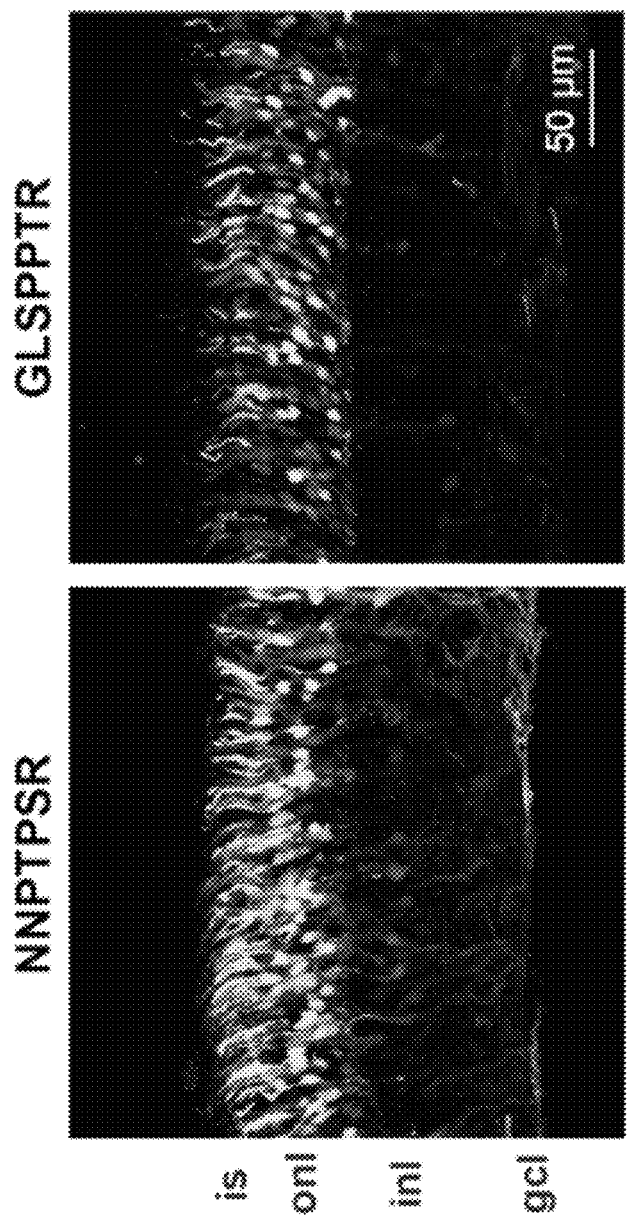

FIG. 13: Representative confocal scanning microscopy images showing AAV-mediated eGFP expression in human retinal explants at nine days in vitro (DIV) after transduction with 1×10E11 total vg (viral genomes) of sc-CMV-eGFP packaged with one of the novel AAV2 (peptide insertion sequences are given on top of each image column). Strong native eGFP fluorescence (grey) in multiple retinal cell types and layers was observed. In particular, many photoreceptor inner segments (is) and cell bodies within the outer nuclear layer (onl) were eGFP positive. IS, inner segments. ONL, outer nuclear layer. INL, inner nuclear layer. ONL, inner nuclear layer. GCL, ganglion cell layer.

Figure 14:
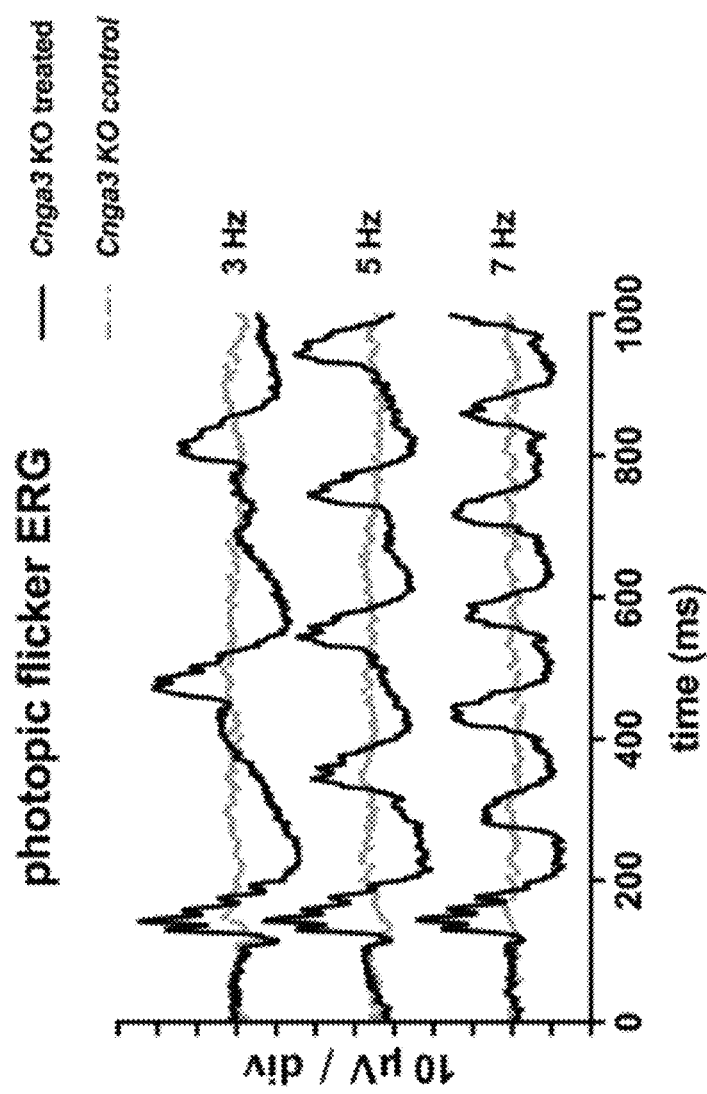

FIG. 14: Representative photopic flicker ERG measurements from a 3 month old Cnga3-deficient mouse 2 months after a single intravitreal injection of 1 µl (containing approximately 1×10E10 total vg of ss-mSWS-mCnga3-WPRE (Michalakis et al. (2010) Restoration of Cone Vision in the CNGA3$^{-/-}$ Mouse Model of Congenital Complete Lack of Cone Photoreceptor Function Mol. Ther.: 2057-2063) packaged with the novel AAV2 "GLSPPTR" capsid. Traces from the treated eye (black) and untreated control eye (dashed grey) at 3.1 log cd sec/m$^2$ and indicated frequency are shown.

Figure 15:
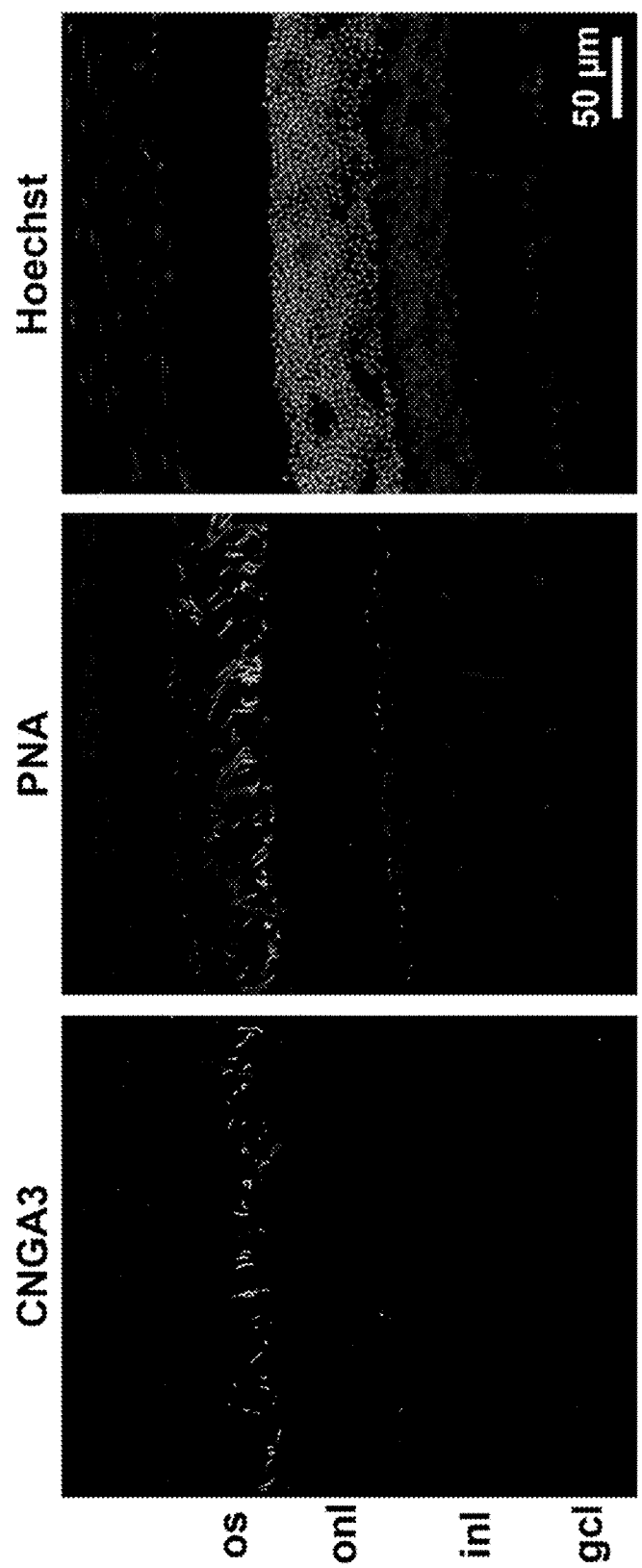

FIG. 15: Representative confocal scanning microscopy images showing cone photoreceptor expression of CNGA3 protein on retinal cross sections from a 3 month old Cnga3-deficient mouse 2 months after a single intravitreal injection of 1 µl (containing approximately 1×10E10 total vg of ss-mSWS-mCnga3-WPRE (Michalakis et al. (2010) Restoration of Cone Vision in the CNGA3$^{-/-}$ Mouse Model of Congenital Complete Lack of Cone Photoreceptor Function Mol. Ther.: 2057-2063) packaged with the novel AAV2 "GLSPPTR" capsid. Strong anti-CNGA3 immunosignal is found in peanut agglutinin (PNA) positive cone photoreceptors. os, outer segments. onl, outer nuclear layer. inl, inner nuclear layer. gcl, ganglion cell layer.

Figure 16:
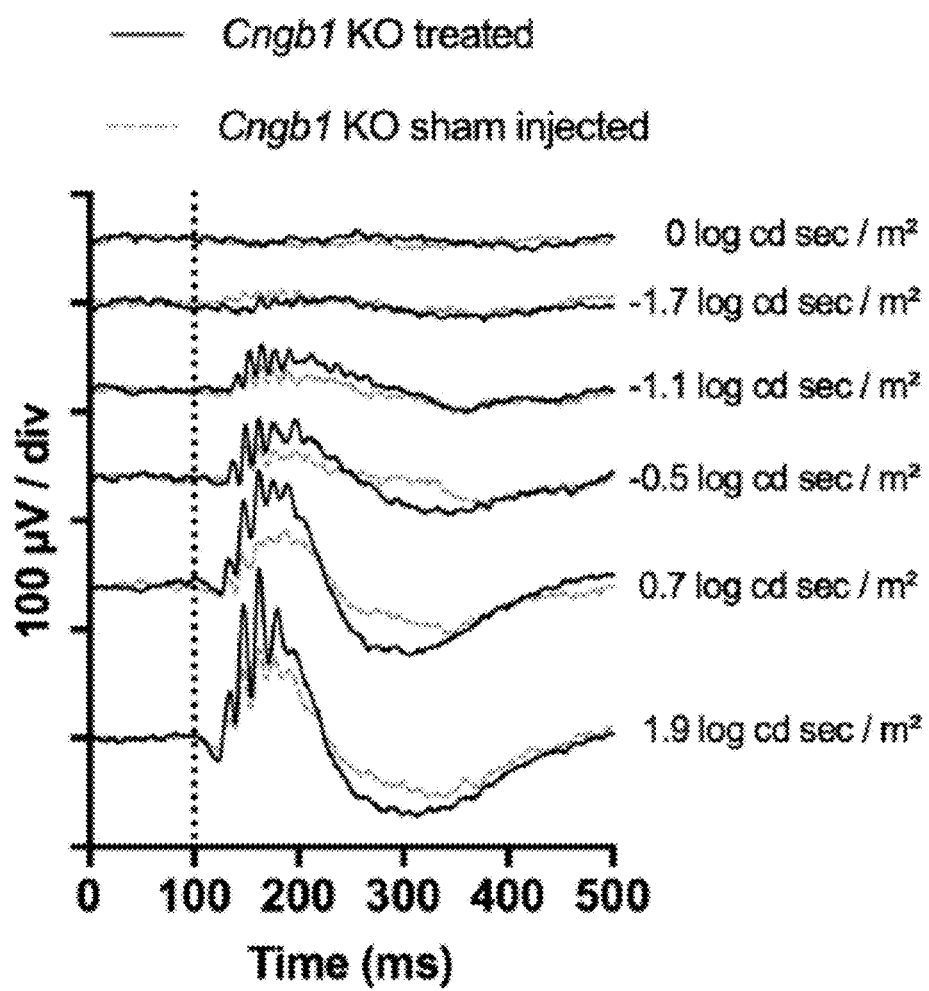

FIG. 16: Representative scotopic single flash ERG measurements from 3 month old Cngb1-deficient mice 2 months after a single intravitreal injection of 1 µl (containing approximately 1×10E10 total vg of ss-mRho-mCngb1-sv40 (Koch et al. 2012) Gene therapy restores vision and delays degeneration in the CNGB1−/− mouse model of retinitis pigmentosa. Hum. Mol. Genet.: 4486-4496) packaged with the novel AAV2 "NNPTPSR" capsid. Traces from the treated eye (black) and untreated control eye (dashed grey) at indicated light stimulus luminance are shown.

The present inventors have found novel AAV capsids with novel peptide insertions that are very valuable for all studies aiming for efficient transduction of retinal cell types and in particular of photoreceptors. Moreover, these novel AAV capsid variants allow for crossing natural barriers for transduction of retinal cell types (and in particular photoreceptors) from the intravitreal or from systemic compartments.

That AAV of the present invention are especially beneficial, is also a result of the special selection process. The selection process comprises two or even three selection rounds, which an AAV of the present invention has to pass. Firstly, an AAV peptide display library similar as described in Perabo et al. (2003) "In vitro selection of viral vectors with modified tropism: the adeno-associated virus display." Molecular Therapy, Vol. 8, No. 1 was provided. In particular, for the construction of plasmid pWt.oen, the HCMV promoter/enhancer cassette and the GFP open reading frame in the plasmid pEGFPC-1 (Clontech, Palo Alto, CA) were substituted with the wildtype AAV-2 genome-encoding fragment of plasmid pUC-AV2 (Girod et al. (1999) "Genetic capsid modifications allow efficient re-targeting of adeno-associated virus type 2. Nat. Med. 5: 1052-1056). A DNA fragment encoding amino acids AAAstopA and the restriction sites NotI and AscI was inserted between amino acid positions 587 and 588 by PCR mutagenesis. To generate a library of AAV plasmids (Library#1) a pool of single-stranded DNA molecules was synthesized as 5'-TTGGCGCGCCGCVNNVNNVNNVNNVNNVNN VNNGGCGGCCGCTTTTTTCCTTGA-3' (bottom strand; SEQ ID NO. 2) and HPLC purified (Metabion GmbH, Martinsried, Germany). For the synthesis of double-stranded molecules a 5'-CTCAAGGAAAAAAGC-3' (SEQ ID NO. 3) primer was used. dsDNA molecules were cloned into the NotI-AscI large fragment of plasmid pWt.oen.

Library#1 was electroporated into *Escherichia coli* strain DH5α using a gene pulser (Bio-Rad, Hercules, CA) and amplified DNA was purified. The efficiency of the transformation was controlled by plating sample aliquots. DNA of more than 20 clones was controlled by sequencing with the primer 5'-ATGTCCGTCCGTGTGTGG-3' (SEQ ID No. 4). The screened sequences showed no homology, indicating a complete randomization of the inserted sequence.

For the production of viruses, 15 150-mm petri dishes of HEK293 cells at 80% confluence were cotransfected with 37.5 µg of DNA. For the production of the AAV library, Library#1 and plasmid pXX6 (obtained from J. Samulski, Chapel Hill, N.C.; Xiao, Li and Samulski (1998) "Production of high-titer recombinant adeno-associated virus vectors in the absence of helper adenovirus." J. Virol. 72: 2224-2232) were cotransfected at a molar ratio of 1:1 in HEK293 cells. After 48 h cells were collected and pelleted by centrifugation. Cells were resuspended in 150 mM NaCl, 50 mM Tris-HCl (pH 8.5), freeze-thawed several times, and treated with Benzonase (50 U/ml) for 30 min at 37° C. Cell debris was removed by centrifugation, and supernatant was loaded onto an iodixanol gradient and subjected to 69,000 rpm for 1 h at 18° C. as described (Zolotukhin et al. (1999) "Recombinant adeno-associated virus purification using novel methods improves infectious titer and yield. Gene Ther. 6: 973-985). Virions were then harvested from the 40% iodixanol phase and titrated by DNA dot-blot hybridization with a rep probe (Girod et al. (1999) "Genetic capsid modifications allow efficient re-targeting of adeno-associated virus type 2. Nat. Med. 5: 1052-1056). This procedure resulted in library #1.

As described above the AAV peptide display library was packaged in HEK293 cells followed by coupling of geno- and phenotype (as described in PCT/EP2008/004366). The latter is required to ensure that the genome encodes the peptide that is displayed on the capsid. In addition, the AAV library had been depleted for mutants binding to HSPG through the peptide sequence that had been inserted to minimize the presence of AAV bearing secondary high affinity binding sites for HSPG (Sallach et al. (2014) "Tropism-modified AAV vectors overcome barriers to successful cutaneous therapy. Mol. Ther. 22:929-39).

In selection round 1, living adult C57BL/6J mice received a single tail vain injection of 100 µl containing approximately 8×10^10 total vector genomes (vg) of the AAV peptide display Library #1. 24 hours later the mice were euthanized by cervical dislocation and the eye was proptosed by placing Dumont #7 curved forceps (Fine Science Tools, Heidelberg) around the rear part close to the optic nerve and applying gentle pressure. The cornea was cut along the equator with a sharp blade. Subsequently, the retina was detached from the retinal pigment epithelium (RPE) and removed from remaining eye tissue, together with the lens and the vitreous body, by gently pulling the forceps upwards. After rinsing the tissue in ice cold 0.1 M phosphate buffer (PB) and removing the lens and any remaining RPE cells with the forceps, the two retinas per mouse were pooled and transferred into an Eppendorf tube, shock frozen in liquid nitrogen and stored at −80° C. for further use. Nuclei were isolated (to ensure that only nuclear DNA was analyzed) from whole retina using the Subcellular Protein Fractionation Kit for Tissues (Thermo Fischer Scientific, #87790). Nuclear DNA was isolated using the DNeasy Blood & Tissue Kit (Qiagen, #69504) and further analyzed by sequencing with a Roche 454 sequencing system for the occurrence of AAV genomes using specific assays targeting the AAV library DNA. Subsequently, the viral DNA around the insertion site was amplified by PCR with primers 5'-GTATCTACCAACCTCCAGAGAG-3' (SEQ ID NO. 5) and 5'-GTGTTGACATCTGCGGTAGC-3' (SEQ ID NO. 6) and cloned via the NotI-AscI sites into the plasmid pWt.oen generating thereby a plasmid pool.

For the production of AAV Library #2, 15 150-mm petri dishes of 293 cells at 80% confluence were cotransfected at a molar ratio of 1:1 with 37.5 µg of the plasmid DNA pool obtained from selection round 1 and plasmid pXX6. After 48 h cells were collected and pelleted by centrifugation. Cells were resuspended in 150 mM NaCl, 50 mM Tris-HCl (pH 8.5), freeze-thawed several times, and treated with Benzonase (50 U/ml) for 30 min at 37° C. Cell debris was removed by centrifugation, and supernatant was loaded onto an iodixanol gradient and subjected to 69,000 rpm for 1 h at 18° C. as described (Zolotukhin et al. (1999) "Recombinant adeno-associated virus purification using novel methods improves infectious titer and yield. Gene Ther. 6: 973-985). Virions were then harvested from the 40% iodixanol phase and titrated by DNA dot-blot hybridization with a rep or a gfp probe (Girod et al. (1999) "Genetic capsid modifications allow efficient re-targeting of adeno-associated virus type 2. Nat. Med. 5: 1052-1056). This procedure resulted in Library #2.

Library #2 was phenotype-genotype coupled (as described in PCT/EP2008/004366), titered and subjected to a new round of in vivo selection. In particular, adult live C57BL/6J mice received a single tail vain injection of 50 µl, containing approx. 5×10^11 total vg. The subsequent steps of selection round 2 were performed as described for selection round 1 resulting in the novel plasmid pool used for generation of Library #3.

For the production of AAV Library #3, 15 150-mm petri dishes of 293 cells at 80% confluence were cotransfected at a molar ratio of 1:1 with 37.5 µg of the plasmid DNA pool obtained from selection round 1 and plasmid pXX6. After 48 h cells were collected and pelleted by centrifugation. Cells were resuspended in 150 mM NaCl, 50 mM Tris-HCl (pH 8.5), freeze-thawed several times, and treated with Benzonase (50 U/ml) for 30 min at 37° C. Cell debris was removed by centrifugation, and supernatant was loaded onto an iodixanol gradient and subjected to 69,000 rpm for 1 h at 18° C. as described (Zolotukhin et al. (1999) "Recombinant adeno-associated virus purification using novel methods improves infectious titer and yield. Gene Ther. 6: 973-985). Virions were then harvested from the 40% iodixanol phase and titrated by DNA dot-blot hybridization with a rep or a gfp probe (Girod et al. (1999) "Genetic capsid modifications allow efficient re-targeting of adeno-associated virus type 2. Nat. Med. 5: 1052-1056). This procedure resulted in Library #3.

In selection round 3a, living adult C57BL/6J mice received a single tail vain injection of 100 µl containing approximately 5×10^11 total vg of the AAV peptide display Library #3. After 24 hours retinas were isolated following the procedure described for selection rounds 1 and 2 with the exception that the pooled retinas were not frozen, but immediately processed for isolation of rod photoreceptors. In particular, a papain dissociation was performed as described in (Feodorova et al. (2015) "Quick and reliable method for retina dissociation and separation of rod photoreceptor perikarya from adult mice." MethodsX 2:39-46) and rods were isolated by anti-CD73-based MACS sorting according to (Eberle et al. (2014) "Subretinal transplantation of MACS purified photoreceptor precursor cells into the adult mouse retina." J. Vis. Exp. 84:e50932). Rod nuclei were isolated (to ensure that only nuclear DNA was analyzed) from MACS-sorted rods using the Subcellular Protein Fractionation Kit for Tissues (Thermo Fischer Scientific, #87790). Nuclear DNA was isolated using the DNeasy Blood & Tissue Kit (Qiagen, #69504). Sequencing with a Roche 454 sequencing system was performed to determine the inserted peptide sequences most predominantly found in rods.

In selection round 3b living adult RG-eGFP mice (Fei et al. (2003) "Development of the cone photoreceptor mosaic in the mouse retina revealed by fluorescent cones in transgenic mice." Mol. Vision 9:31-42) expressing enhanced green fluorescent protein (eGFP) in cone photoreceptors received a single tail vain injection of 100 µl containing approximately 5×10^11 total vg of the AAV peptide display Library #3. After 24 hours retinas were isolated following the procedure described for selection rounds 1 and 2 with the exception that the pooled retinas were not frozen, but immediately processed for isolation of cone photoreceptors. In particular, a papain dissociation was performed as described in (Feodorova et al. (2015) "Quick and reliable method for retina dissociation and separation of rod photoreceptor perikarya from adult mice." MethodsX 2:39-46) and cones were FACS sorted (marker eGFP) according to (Becirovic et al. (2016) In Vivo Analysis of Disease-Associated Point Mutations Unveils Profound Differences in mRNA Splicing of Peripherin-2 in Rod and Cone Photoreceptors." PLOS Genetics 12(1):e1005811). Cone nuclei were isolated (to ensure that only nuclear DNA was analyzed) from FACS-sorted cones using the Subcellular Protein Fractionation Kit for Tissues (Thermo Fischer Scientific, #87790). Nuclear DNA was isolated using the DNeasy Blood & Tissue Kit (Qiagen, #69504). Sequencing with a Roche 454 sequencing system was performed to determine the inserted peptide sequences most predominantly found in cones.

For the generation of novel helper plasmids for the production of AAV vectors with the novel capsid variants synthetic single strand DNA oligos coding for the top (5'-CGCGGCCGCANNNNNNNNNNNNN NNNNNNNGCCG-3') (SEQ ID NO. 7) and bottom (5'-CGCGCGGCNNNNNNNNNNNNNNNNNNN NNNTGCGGC-3') (SEQ ID NO. 8) strands encoding selected insertion sequences as obtained in the previous selection rounds flanked by 2-3 alanines on either end were synthesized (Eurofins Genomics GmbH, Ebersberg, Germany), hybridized to form double stranded DNA oligos with and flanked by overhangs Mlul-Ascl restriction site were annealed and ligated into the Mlul-Ascl restriction sites of the AAV trans plasmid pRC99 (Nickiin et al. (2001) "Efficient and selective AAV2-mediated gene transfer directed to human vascular endothelial cells" Molecular therapy: the journal of the American Society of Gene Therapy 4, 174-181 and Girod et al. (1999) "Genetic capsid modifications allow efficient re-targeting of adeno-associated virus type 2" Nature medicine 5, 1052-1056) expressing AAV2 Rep and Cap genes resulting in the generation of AAV2 VP1-3 open reading frame with the intended peptide insertions at a position corresponding to amino acid 587 of VP1. The insertion of the sequence destroys the Mlul/Ascl sites and generates a novel Eagl site which can be used for screening of correct clones. The correct sequence of the resulting plasmids was verified by standard sequencing using the primer 5'-CTTTGGGAAGCAAGGCTCAG-3' (SEQ ID NO. 9).

These modified pRC99 plasmids were used to produce AAV particles with the desired novel AAV capsid modification for biological testing. AAV production was performed by standard techniques described in (Michalakis et al. (2010) "Restoration of cone vision in the CNGA3−/− mouse model of congenital complete lack of cone photoreceptor function, Molecular therapy: the journal of the American Society of Gene Therapy 18, 2057-2063 and Becirovic et al. (2016) "AAV Vectors for FRET-Based Analysis of Protein-Protein Interactions in Photoreceptor Outer Segments." Front Neurosci. 10:356). A self-complementary (sc) AAV cis plasmid containing a CMV-eGFP expression cassette (AAV-sc-CMV-eGFP) (Hacker et al. (2005) "Adeno-associated virus serotypes 1 to 5 mediated tumor cell directed gene transfer and improvement of transduction efficiency." J. Gene Med. 7(11):1429-38) was used as cis plasmid.

For the production of capsid modified AAV variants, 15 150-mm petri dishes of 293 cells at 80% confluence were cotransfected at a molar ratio of 1:1 with 37.5 µg of each of the modified pRC99 plasmids, plasmid pXX6 and plasmid AAV-sc-CMV-eGFP. After 48 h cells were collected and pelleted by centrifugation. Cells were resuspended in 150 mM NaCl, 50 mM Tris-HCl (pH 8.5), freeze-thawed several times, and treated with Benzonase (50 U/ml) for 30 min at 37° C. Cell debris was removed by centrifugation, and supernatant was loaded onto an iodixanol gradient and subjected to 69,000 rpm for 1 h at 18° C. as described (Zolotukhin et al. (1999) "Recombinant adeno-associated virus purification using novel methods improves infectious titer and yield. Gene Ther. 6: 973-985). Virions were then harvested from the 40% iodixanol phase, rebuffered to phosphate buffered saline (PBS) using Amicon Ultra-4 centrifugal filter units, 100 kDa (Millipore), and genomic particle titers were determined by qPCR (LightCycler System, Roche Diagnostics, Mannheim, Germany) using ITR specific primers (D'Costa et al. (2016) "Practical utilization of recombinant AAV vector reference standards: focus on vector genomes titration by free ITR qPCR." Mol. Ther. Methods Clin. Dev. 5:16019).

In this way AAV helper plasmids for the production of AAV capsid variant vectors with a high transduction efficiency of retinal photoreceptors have been obtained. The presence of a specific genome encoding a modified AAV capsid in the target cell (e.g. cone photoreceptor) 24 hours after intravenous injection suggests that these particular capsid modifications enable to overcome the following biological barriers:
1. Escape from the host immune system
2. Escape from the systemic clearance
3. Blood vessel endothelial cell barrier and retina-blood-barrier (RBB)
4. Within the retina: escape from the retinal blood vessels and diffusion into the retinal tissue
5. If entry from the choroidal blood vessels is assumed: transfer through the Bruch's membrane, the retinal pigment epithelial cell barrier and the photoreceptor extracellular matrix and probably the outer limiting membrane to finally enter the photoreceptor cells. If the entry pathway is the photoreceptor outer segment the connecting cilium has to be overcome as well
6. If entry from the vitreal blood vessels is assumed: transfer though the inner limiting membrane, ganglion cell layer, the inner plexiform layer, the inner nuclear layer, the outer plexiform layer to finally enter the photoreceptors at their synaptic endings
7. Upon cell entry, the AAV particles have to traffic through and escape the endolysosomal vesicles system, uncoat and shuttle their genome through the nuclear membrane into the cell nucleus
8. Thus, detection of specific AAV genomes in the screening in the nuclei of the target cells suggests that all these barriers had to be successfully overcome In addition, the libraries had been depleted for heparin binding. This is of particular importance since it has been assumed that transduction of retinal cells and photoreceptors in particular generally requires heparin binding. By using heparin-binding depleted libraries specifically selected for novel AAVs that most probably use distinct cell entry and trafficking mechanisms compared to the standard AAVs and previously generated AAVs.

As mentioned above, the novel capsids are of great value for all applications aiming for efficient transduction of retinal cells. This can be in the living animal or in explant tissue culture or in cell culture. Moreover, this can be for basic research or for clinical applications like ocular gene therapy. Furthermore, the applications are not limited to gene expression, but can also include gene knock down using siRNA (shRNA) technology or gene editing with e.g. nucleases like the zinc finger, TALEN or CAS9/CRISPR systems. Finally, the novel AAVs are also useful as a cargo system for other molecules including but not limited to DNA, RNA, peptides, proteins, chemical compounds.

The present invention relates to an adeno-associated virus (AAV), the AAV comprising an insertion of at least 6-8 amino acids between the positions corresponding to position 587 and 588 of SEQ ID NO: 1, wherein the insertion sequence has from the N-terminus to the C-terminus the formula I:

$$X_{1A}\text{-}X_{1B}\text{-}X_2\text{-}X_3\text{-}X_4\text{-}X_5\text{-}X_6\text{-}X_7 \qquad \text{(formula I)}$$

wherein $X_5$ is selected from P (Pro), L (Leu) and V (Val);
wherein $X_7$ is R (Arg);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present, or
wherein $X_5$ is selected from S (Ser) and T (Thr);
wherein $X_7$ is S (Ser);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present, or
wherein $X_5$ is selected from A (Ala) and Q (Gln);
wherein $X_7$ is A (Ala);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present,
wherein viral AAV DNA is present in mouse retinal nuclear extracts after 24 hours,
when the AAV is administered intravenously into the tail vein of a C57-Bl6J mouse, and
wherein viral AAV DNA is present in MAC-sorted rods using anti-CD73-coated magnetic beads and/or FACS-sorted cones, wherein the cones express eGFP and are FACS sorted based on their eGFP expression, 24 hours after administration, when the AAV is administered intravenously into the tail vein of a C57-Bl16J mouse for rod sorting and into the tail vein of RG-eGFP mice line R685933 for cone sorting.

An adeno-associated virus (AAV) as used herein may be used to refer to any AAV virus itself or parts thereof, e.g. the viral capsid, the viral genome, and the like. The term "AAV" also encompasses all subtypes, both naturally occurring and recombinant forms, and variants thereof.

Non-limiting examples of AAVs include AAV type 1 (AAV-1), AAV type 2 (AAV-2), AAV type 3 (AAV-3), AAV type 3B (AAV-3B), AAV type 4 (AAV-4), AAV type 5 (AAV-5), AAV type 6 (AAV-6), AAV type 7 (AAV-7), AAV type 8 (AAV-8), AAV9, AAV10, AAV11, AAV12, AAV13, rh10, avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

In particular, the experiments as described herein were performed with modified AAV2 capsids. However, other AAV capsids (from other AAVs as described herein) also tolerate peptide insertions in the corresponding capsid positions (Michelfelder et al. (2011) "Peptide ligands incorporated into the threefold spike capsid domain to re-direct gene transduction of AAV8 and AAV9 in vivo" PloS one 6, e23101).

Therefore the peptide insertions (insertion sequences as described herein) can be transferred to the other known AAV capsids, e.g. to any of the capsids of any of the AAVs as described herein or e.g. into AAV8, AAV9, AAV7 or AAV5. These AAVs can have a higher efficiency and broader transduction profiles in the retina compared to AAV2.

Moreover, the AAV capsid peptide insertions can be combined with the capsid tyrosine, threonine and serine mutations (Petrs-Silva et al. (2009) "High-efficiency transduction of the mouse retina by tyrosine-mutant AAV serotype vectors" Molecular therapy: the journal of the American Society of Gene Therapy 17, 463-471 and Zhong et al. (2008) "Next generation of adeno-associated virus 2 vectors: point mutations in tyrosines lead to high-efficiency transduction at lower doses" Proceedings of the National Academy of Sciences of the United States of America, 105, 7827-7832) to reduce proteasome-mediated degradation and enhance transduction efficacy.

The AAV can be AAV2.

Furthermore, the AAV may be a naturally occurring (wild type AAV), a variant or recombinant AAV. By "naturally occurring" or "wild-type" AAV it is meant any adeno-associated virus or derivative thereof comprising viral proteins such as the viral capsid that consists of viral (capsid) proteins that occur in nature. Thus, the AAV of the present invention can be a naturally occurring AAV only comprising an insertion sequence as described herein between the positions corresponding to position 587 and 588 of SEQ ID NO: 1.

By an "AAV variant" or a "variant AAV" it is meant to include an AAV viral particle comprising a variant, or mutant, of an AAV protein such as a mutant AAV protein. Examples of variant AAV proteins include AAV proteins comprising at least one amino acid difference (e.g., amino acid substitution, amino acid insertion, amino acid deletion) relative to a corresponding parental AAV protein, i.e. an AAV protein from which it was derived, a wild type AAV protein, etc., where the variant AAV protein does not consist of an amino acid sequence present in a naturally occurring AAV protein. For example, such variant AAVs may comprise a mutation in the capsid protein VP3 in addition to the inventive insertion sequence.

In addition to differing structurally, i.e. at the sequence level, from the corresponding parental AAV, the AAV variant may differ functionally from the corresponding parental AAV. Put another way, the variant capsid protein comprising the at least one amino acid difference relative to a corresponding parental AAV capsid protein may confer functional characteristics on the AAV variant that are not possessed by the corresponding parental AAV. For example, the AAV variant may have a different cellular tropism, i.e. a different affinity for and/or ability to infect a particular type of cell, e.g. the AAV variant may bind to a cell, e.g. a retinal cell, with an increased (or decreased) affinity than the parental AAV, and/or infect/transduce a cell, e.g. a retinal cell, with an increased (or decreased) efficiency than the parental AAV such that more (or less) cells of a cell population is transduced/infected with the same titer of viral particles. As a second example, the AAV variant may have a greater (or lesser) affinity for antibodies produced by the host animal, e.g. the AAV variant may bind with greater (or lesser) affinity to neutralizing antibodies and be cleared from the host tissue to a greater (or lesser) extent. Thus, the AAV of the present invention can be a mutant (variant) AAV comprising an insertion sequence as described herein between the positions corresponding to position 587 and 588 of SEQ ID NO: 1.

By "recombinant AAV" or "rAAV" it is meant to include any AAV that comprises a heterologous polynucleotide sequence in its viral genome. In general, the heterologous polynucleotide is flanked by at least one, and generally by two naturally occurring or variant AAV inverted terminal repeat sequences (ITRs). The term rAAV vector encompasses both rAAV vector particles and rAAV vector plasmids. The virus vector as described herein also is a rAAV. Thus, for example, a rAAV that comprises a heterologous polynucleotide sequence would be a rAAV that includes a nucleic acid sequence not normally included in a naturally-occurring, wild-type AAV, for example, a transgene (e.g. a non-AAV RNA-coding polynucleotide sequence, non-AAV protein-coding polynucleotide sequence), a non-AAV promoter sequence, a non-AAV poly-adenylation sequence, etc.

Such recombinant AAV vectors are common general knowledge in the art and so the skilled person also knows how to construct such recombinant AAVs.

A "rAAV vector genome" or "rAAV genome" is an AAV genome (i.e. vDNA) that comprises one or more heterologous nucleic acid sequences. rAAV vectors can generally require only the terminal repeat(s) (TR) in as to generate virus. All other viral sequences are considered dispensable and may be supplied in trans (Muzyczka, (1992) Curr. Topics Microbiol. Immunol. 158:97). Typically, the rAAV vector genome will only retain the one or more TR sequence so as to maximize the size of the transgene that can be efficiently packaged by the vector/capsid. The structural and non-structural protein coding sequences may be provided in trans (e.g., from a vector, such as a plasmid, or by stably integrating the sequences into a packaging cell). In embodiments of the invention the rAAV vector genome comprises at least one TR sequence (e g., AAV TR sequence), optionally two TRs (e.g., two AAV TRs), which typically will be at the 5' and 3' ends of the vector genome and flank the heterologous nucleic acid, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e. mediates the desired functions such as replication, virus packaging, integration and/or provirus rescue, and the like). The TR can be an AAV TR or a non-AAV TR For example, a non-AAV TR sequence such as those of other parvoviruses (e.g. canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/ or addition. Further, the TR can be partially or completely synthetic, such as the "double-D sequence" as described in U.S. Pat. No. 5,478,745 to Samulski et al.

An 'AAV terminal repeat" or "AAV TR" may be from any AAV, including but not limited to serotypes 1 , 2, 3, 3B, 4, 5, 6, 7, 8, 9, 10, 11, 12 or 13 or any other AAV now known or later discovered. An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like The virus vectors of the invention can further be "targeted" virus vectors (e.g., having a directed tropism) and/or a "hybrid" parvovirus (i.e, in which the viral TRs and viral capsid are from different parvoviruses) as described in international patent publication WO 00/28004 and Chao et al., (2000) Molecular Therapy 2:619.

Also embraced by the term recombinant AAV are AAVs, which comprise e.g. only the capsid of the AAV and carry within the capsid a non-nucleic acid cargo such as protein, polypeptide or another molecule in addition to or in substitution of its genome. For example, the capsid may comprise a nucleic acid which is heterologous to the AAV-related genome. It is also envisioned that the capsid carried a nucleic acid which is heterologous (not the AAV nucleic acid). How such recombinant AAVs are produced is e.g. described in U.S. Pat. No. 9,610,354 B2 or WO1996000587 A1.

A capsid protein as used herein refers to an AAV capsid protein. Typically, the AAV capsid is composed of 60 capsid protein subunits, VP1, VP2, and VP3 that are arranged in an icosahedral symmetry usually in a ratio of 1:1:10 or 1:1:20. It was reported that VP2 and VP3 are crucial for correct virion assembly. More recently, however, it was shown VP2 to be unnecessary for the complete virus particle formation and an efficient infectivity, and also presented that VP2 can tolerate large insertions in its N terminus, while VP1 cannot, probably because of the PLA2 domain presence. Notably, the N-terminus of VP1 is sequestered within the mature capsid. It can contain a phospholipase A2-like region and putative nuclear localization signals. Thus, the capsid protein can comprise a VP1 capsid protein of the present invention and further one or both of AAV VP2 and/or VP3 capsid proteins.

The sequences for the VP1, VP2 and VP3 capsid protein are known to the skilled person. Also envisioned are variants of any one of VP1, VP2 and VP3 as long as they are still able to assemble a capsid (see also Table 1 shown herein summarizing some sequences). Methods to analyse if a capsid is assembled are also known to the skilled person and e.g. described in Sonntag et al. (2011) "The Assembly-Activating Protein Promotes Capsid Assembly of Different Adeno-Associated Virus Serotypes" J. Virol. 85(23): 12686-12697.

A "variant" of a capsid protein of the present invention encompasses a capsid protein comprising a mutation. The mutation can be present with regard to any capsid sequence. For example, the mutation may be present with regard to any one the sequences as indicated in Table 1 as long as it results in a mutated capsid protein. Such mutations can include one or more point mutations, such as 1, 2, 5, 10, 15, 20, 50 or more point mutations. A variant can also comprise insertions (addition of one or more nucleotides to the DNA/RNA or addition of one or more amino acids in a certain capsid protein such as VP1, VP2, and/or VP3), such as 1, 2, 3, 5, 6, or more insertions. Both, point mutations and insertions can be selected according to general rules known in the art, which can have no effect on the activity of the amino acid sequence compared to e.g. an amino acid sequence of SEQ ID NO: 1.

A variant can also include a deletion of a nucleic acid base or amino acid resulting in in a capsid protein with a reduced number of amino acids. Thus, a polypeptide can comprise a deletion of 1, 2, 3, 4, 5, 10, 20, 30 or more amino acid residues in comparison to its wildtype sequence e.g. of any of the sequences as shown in Table 1. Also encompassed are deletions of more than 1, 2, 3, 4, 10, 20, 30, 40, 50, 60, 70, 80, 90, 100, 200, 300 or more nucleic acid bases compared to a nucleic acid molecule shown in Table 1. The variant can however still have the same functional properties as any of the polypeptides or the nucleic acid molecules depicted in Table 1.

Given that also variants of the capsid proteins (polypeptides, nucleic acid molecules) as described herein are encompassed by the present invention, the present invention also encompasses capsid nucleic acid sequences or polypeptide sequences which have a sequence identity of 80%, 85%, 90%, 95%, 97%, 99% or 100% with any of the polypeptides/nucleic acid molecules indicated in Table 1.

Thus, a recombinant AAV carrying a polypeptide, protein or molecule can comprise VP1, VP3 and/or VP2 capsid proteins as the only AAV proteins present in that vector.

Thus, the AAV of the present invention can be a recombinant AAV comprising an insertion sequence as described herein between the positions corresponding to position 587 and 588 of SEQ ID NO: 1.

It is also envisioned that the AAV comprises or has a sequence having a sequence identity of at least 70%, 75%, 80%, 85%, 90%, 95%, 97%, 99% or 100% with a naturally occurring AAV type 1 (AAV-1), AAV type 2 (AAV-2), AAV type 3 (AAV-3), AAV3B, AAV type 4 (AAV-4), AAV type 5 (AAV-5), AAV type 6 (AAV-6), AAV type 7 (AAV-7), AAV type 8 (AAV-8), AAV9, AAV10, AAV11, AAV12, rh10, avian AAV, bovine AAV, canine AAV, equine AAV, primate AAV, non-primate AAV, and ovine AAV. It is also envisioned that the AAV has a sequence identity of at least 70%, 75%, 80%, 85%, 90%, 95%, 97%, 99% or 100% with a sequence as referenced in Table 1.

The term "polypeptide" when used herein means a peptide, a protein, or a polypeptide, which is used interchangeable and which encompasses amino acid chains of a given length, wherein the amino acid residues are linked by covalent peptide bonds. The polypeptides may comprise amino acids of the 20 gene-encoded amino acids. These are known to the skilled person. Also encompassed are amino acids other than the 20 gene-encoded amino acids, namely unnatural amino acids. Examples of such unnatural amino acids include D-amino acids, homo amino acids, N-methyl amino acids, alpha-methyl amino acids, beta (homo) amino acids, gamma amino acids, helix/turn stabilizing motifs, backbone modifications (e.g. peptoids). Also envisioned are unusual amino acids found in nature and which are known to the skilled person. Examples include selenocysteine, hydroxyproline (Hyp), beta-alanine, citrulline (Cit), ornithine (Orn), norleucine (Nle), 3-nitrotyrosine, nitroarginine, pyroglutamic acid (Pyr). Thus, the term polypeptide can also include amino acid sequences comprising an amino acid other than the amino acids as shown in the 20-gene-ecoded amino acids. It may e.g. comprise one or more unusual amino acids found in nature and/or one or more unnatural amino acids.

The term polypeptide also refers to, and does not exclude, modifications of the polypeptide. Such modifications are known to the skilled artesian and for example listed in WO 2010/093784.

With regard to the term "nucleic acid molecule" when used herein encompasses any nucleic acid molecule having a nucleotide sequence of bases comprising purine- and pyrimidine bases which are comprised by said nucleic acid molecule, whereby said bases represent the primary structure of a nucleic acid molecule. Nucleic acid sequences can include DNA, cDNA, genomic DNA, RNA, both sense and antisense strands. The polynucleotide of the present invention can be composed of any polyribonucleotide or polydeoxribonucleotide, which may be unmodified RNA or DNA or modified RNA or DNA.

A variety of modifications can be made to DNA and RNA; thus, the term "nucleic acid molecules" can embrace chemically, enzymatically, or metabolically modified forms. "Modified" bases include, for example, tritylated bases and unusual bases such as inosine.

In accordance with the present invention, the term "identical" or "percent identity" in the context of two or more nucleic acid molecules or amino acid sequences, refers to two or more sequences or subsequences that are the same, or that have a specified percentage of amino acid residues or nucleotides that are the same (e.g., at least 95%, 96%, 97%, 98% or 99% identity), when compared and aligned for maximum correspondence over a window of comparison, or over a designated region as measured using a sequence comparison algorithm as known in the art, or by manual alignment and visual inspection. Sequences having, for example, 80% to 95% or greater sequence identity are considered to be substantially identical. Such a definition also applies to the complement of a test sequence. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Also available to those having skill in this art are the BLAST and BLAST 2.0 algorithms (Altschul Nucl. Acids Res. 25 (1977), 3389-3402). The BLASTN program for nucleic acid sequences uses as defaults a word size (W) of 28, an expectation threshold (E) of 10, match/mismatch score 1, −2, gap costs linear and a comparison of both strands. For amino acid sequences, the BLASTP program uses as defaults a word size (W) of 6, and an expectation threshold (E) of 10, gap costs are Existence: 11 and Extension: 1. Furthermore, the BLOSUM62 scoring matrix (Henikoff Proc. Natl. Acad. Sci., USA, 89, (1989), 10915) can be used.

For example, BLAST2.0, which stands for Basic Local Alignment Search Tool (Altschul, Nucl. Acids Res. 25 (1997), 3389-3402; Altschul, J. Mol. Evol. 36 (1993), 290-300; Altschul, J. Mol. Biol. 215 (1990), 403-410), can be used to search for local sequence alignments.

The AAVs as described herein have an insertion of at least 6-8 amino acids between the positions corresponding to position 587 and 588 of SEQ ID NO: 1. The insertion sequence can have 6 amino acids. The insertion sequence can also have 7 amino acids. The insertion sequence can have 8 amino acids. Thus, also envisioned are AAVs comprising an insertion sequence as described herein, wherein $X_{1A}$ is absent and $X_{1B}$ is present or wherein $X_{1B}$ is absent and $X_{1A}$ is present.

The insertion sequence has from the N-terminus to the C-terminus the formula I: $X_{1A}$-$X_{1B}$-$X_2$-$X_3$-$X_4$-$X_5$-$X_6$-$X_7$ (formula I). In this formula, $X_5$ can be selected from P (Pro), L (Leu) and V (Val); wherein $X_7$ can be R (Arg); $X_{1A}$, $X_{1B}$, $X_2$, $X_3$, $X_4$, $X_6$ can be independently any amino acid; and $X_{1A}$ and/or $X_{1B}$ can be independently optionally absent or present, wherein optionally viral AAV DNA is present in mouse retinal nuclear extracts after 24 hours, when the AAV is administered intravenously into the tail vein of a C57-Bl6J mouse.

Thus, the present invention also relates to an adeno-associated virus (AAV), the AAV comprising
an insertion of at least 6-8 amino acids between the positions corresponding to position 587 and 588 of SEQ ID NO: 1 (insertion sequence); wherein the insertion sequence has from the N-terminus to the C-terminus the formula I:

  (formula I), wherein $X_5$ is selected from P (Pro), L (Leu) and V (Val);
wherein $X_7$ is R (Arg);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present, wherein optionally viral AAV DNA is present in mouse retinal nuclear extracts after 24 hours, when the AAV is administered intravenously into the tail vein of a C57-Bl6J mouse.

Similarly, the present invention relates to an adeno-associated virus (AAV) VP1 capsid protein, the AAV VP1 capsid protein comprising an insertion of at least 6-8 amino acids between the positions corresponding to position 587 and 588 of SEQ ID NO: 1 (insertion sequence), wherein the insertion sequence has from the N-terminus to the C-terminus the formula I:

  (formula I), wherein $X_5$ is selected from P (Pro), L (Leu) and V (Val);
wherein $X_7$ is R (Arg);
wherein $X_{1A}$, $X_{1B}$, $X_2$, $X_3$, $X_4$, $X_6$ are independently any amino acid;

In particular, in the AAV or the AAV VP1 capsid protein $X_5$ can be P (Pro). Alternatively, $X_5$ can be L (Leu). Alternatively, $X_5$ can be V (Val). Additionally or alternatively $X_{1A}$ and/or $X_{1B}$ can be selected from G, S, N, V and P, preferably $X_{1A}$ and/or $X_{1B}$ are N. Additionally or alternatively $X_2$ can be selected from L, S and N, preferably $X_2$ can be S. Additionally or alternatively $X_3$ can be selected from S, P, T, Q. $X_3$ can also be selected from S and P. Additionally or alternatively $X_4$ can be selected from P, G, S, A and T, preferably $X_4$ can be S. Additionally or alternatively $X_6$ can be selected from T, P, N, Q and S, preferably $X_6$ can be P. Thus, the AAV or the AAV VP1 capsid protein of the present invention can comprise the insertion sequence GLSPPTR (SEQ ID NO: 10), SSPGLPR (SEQ ID NO: 11), NSTSVNR (SEQ ID NO: 12), VSSSLQR (SEQ ID NO: 13), PNQAPPR (SEQ ID NO: 14) or NNPTPSR (SEQ ID NO: 15) as described herein.

Alternatively in formula I, $X_5$ can be selected from S (Ser) and T (Thr); $X_7$ can be S (Ser); $X_{1A}$, $X_{1B}$, $X_2$, $X_3$, $X_4$, $X_6$ can independently be any amino acid; and $X_{1A}$ and/or $X_{1B}$ can independently be optionally absent or present.

Thus, the present invention also relates to an adeno-associated virus (AAV), the AAV comprising
an insertion of at least 6-8 amino acids between the positions corresponding to position 587 and 588 of SEQ ID NO: 1, wherein the insertion sequence has from the N-terminus to the C-terminus the formula I:

  (formula I), wherein $X_5$ is selected from S (Ser) and T (Thr);
wherein $X_7$ is S (Ser);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present, wherein optionally viral AAV DNA is present in mouse retinal nuclear extracts after 24 hours, when the AAV is administered intravenously into the tail vein of a C57-Bl6J mouse.

Similarly, the present invention also relates to an adeno-associated virus (AAV) VP1 capsid protein, the AAV VP1 capsid protein comprising
an insertion of at least 6-8 amino acids between the positions corresponding to position 587 and 588 of SEQ ID NO: 1, wherein the insertion sequence has from the N-terminus to the C-terminus the formula 1:

  (formula I), wherein $X_5$ is selected from S (Ser) and T (Thr);
wherein $X_7$ is S (Ser);
wherein $X_{1A}$, $X_{1B}$, $X_2$, $X_3$, $X_4$, $X_6$ are independently any amino acid;

wherein $X_{1A}$ and/or $X_{1B}$ are independently optionally absent or present.

In particular in the AAV or the AAV VP1 capsid protein $X_5$ can be S (Ser). Alternatively, $X_5$ can be T (Thr). Additionally or alternatively $X_{1A}$ and/or $X_{1B}$ can be selected from G, R, H and S. Additionally or alternatively $X_2$ can be selected from A, S and Q, preferably, $X_2$ can be A. Additionally or alternatively $X_3$ can be selected from H, N and A, preferably $X_3$ can be N. Additionally or alternatively $X_4$ can be selected from R, Q and D, preferably $X_4$ can be R. Additionally or alternatively $X_6$ can be selected from R, S and D, preferably $X_6$ can be D.

Thus, the AAV or the AAV VP1 capsid protein of the present invention can also comprise the insertion sequence GAHRSDS (SEQ ID NO. 16), RANQTSS (SEQ ID NO. 17), HSARTDS (SEQ ID NO. 18) or SQNDSRS (SEQ ID NO. 19).

Alternatively, in formula I, $X_5$ can be selected from A (Ala) and Q (Gln); $X_7$ can be A (Ala); $X_{1A}$, $X_{1B}$, $X_2$, $X_3$, $X_4$, $X_6$ can independently be any amino acid; and $X_{1A}$ and/or $X_{1B}$ can independently be optionally absent or present.

Thus, the present invention also relates to an adeno-associated virus (AAV), the AAV comprising
an insertion of at least 6-8 amino acids between the positions corresponding to position 587 and 588 of SEQ ID NO: 1, wherein the insertion sequence has from the N-terminus to the C-terminus the formula I:

$$X_{1A}\text{-}X_{1B}\text{-}X_2\text{-}X_3\text{-}X_4\text{-}X_5\text{-}X_6\text{-}X_7 \quad \text{(formula I)},$$

wherein $X_5$ is selected from A (Ala) and Q (Gln);
wherein $X_7$ is A (Ala);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present, wherein optionally viral AAV DNA is present in mouse retinal nuclear extracts after 24 hours, when the AAV is administered intravenously into the tail vein of a C57-Bl6J mouse.

Similarly, the present invention also relates to an adeno-associated virus (AAV) VP1 capsid protein, the AAV VP1 capsid protein comprising an insertion of at least 6-8 amino acids between the positions corresponding to position 587 and 588 of SEQ ID NO: 1, wherein the insertion sequence has from the N-terminus to the C-terminus the formula 1:

$$X_{1A}\text{-}X_{1B}\text{-}X_2\text{-}X_3\text{-}X_4\text{-}X_5\text{-}X_6\text{-}X_7 \quad \text{(formula I)},$$

wherein $X_5$ is selected from A (Ala) and Q (Gln);
wherein $X_7$ is A (Ala);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present.

In particular in the AAV or the AAV VP1 capsid protein $X_5$ can be A (Ala). Alternatively, $X_5$ can be Q (Gln). Additionally or alternatively $X_{1A}$ and/or $X_{1B}$ can be selected from N and R. Additionally or alternatively $X_2$ can be selected from S and G. Additionally or alternatively $X_3$ can be selected from R and S. Additionally or alternatively $X_4$ can be selected from P and L. Additionally or alternatively $X_6$ can be selected from A and N.

Thus, the AAV or the AAV VP1 capsid protein of the present invention can also comprise the insertion sequence NSRPAAA (SEQ ID NO. 20) or RGSLQNA (SEQ ID NO. 21).

The insertion of at least 6-8 amino acids is in between the positions corresponding to position 587 and 588 of SEQ ID NO: 1. The term "position" when used in accordance with the present invention means the position of either an amino acid within an amino acid sequence of SEQ ID NO. 1. Notably, SEQ ID NO. 1 corresponds to the VP1 protein of the capsid of AAV2.

The term "corresponding" as used herein also includes that a position is not only determined by the number of the preceding nucleotides/amino acids. The position of a given nucleotide in accordance with the present invention which may be substituted may vary due to deletions or additional nucleotides elsewhere in a (mutant, recombinant or wild-type) AAV capsid protein VP1 including the promoter and/or any other regulatory sequences or gene (including exons and introns). Similarly, the position of a given amino acid in accordance with the present invention which may be substituted may very due to deletion or addition of amino acids elsewhere in a (mutant or wild-type) AAV capsid protein VP1.

Thus, under a "corresponding position" in accordance with the present invention it is preferably to be understood that amino acids may differ in the indicated number but may still have similar neighbouring nucleotides/amino acids. Said amino acids which may be exchanged, deleted or added are also comprised by the term "corresponding position". Specifically, the skilled person may, when aligning the reference sequence (subject sequence) SEQ ID No: 1 with an amino acid sequence of interest (query sequence), for example, inspect a sequence of interest for the sequence motif GNRQ (positions 586-589 of SEQ ID NO: 1; SEQ ID NO. 22) when looking for the amino acid position as specified herein (i.e., a position corresponding to 587 and 588 of the amino acid sequence shown in SEQ ID No: 1).

In order to determine whether an amino acid residue in a given (mutant or wild-type) amino acid sequence corresponds to a certain position in the amino acid sequence of SEQ ID No: 1, the skilled person can use means and methods well-known in the art, e.g., alignments, either manually or by using computer programs such as BLAST2.0, which stands for Basic Local Alignment Search Tool or ClustalW or any other suitable program which is suitable to generate sequence alignments.

It is also envisioned that the insertion sequence is flanked by one or more flexible amino acids on one or both ends of the insertion sequence. Flexible amino acids allow adjacent protein domains to move freely relative to one another. Any flexible amino acid is embraced by the expression flexible amino acid. The person skilled in the art knows which amino acids are flexible and which are less flexible.

A "flexible amino acid" as used herein can be selected from A (Ala), L (Leu), G (Gly), S (Ser) and T (Thr). The flexible amino acid can also be selected from G (Gly), S (Ser) and A (Ala). The flexible amino acid can also be Ala.

The insertion sequence can be flanked on one or both ends with any number of flexible amino acids. For example, the insertion sequence can be flanked on one or both ends with 1, 2, 3, 4, 5, 6, 7, 8, 9, or more flexible amino acids.

Also encompassed are AAVs or AAV VP1 capsid proteins of the present invention, wherein the insertion sequence has from the N-terminus to the C-terminus the formula II:

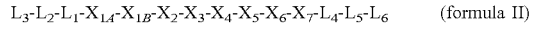
$$L_3\text{-}L_2\text{-}L_1\text{-}X_{1A}\text{-}X_{1B}\text{-}X_2\text{-}X_3\text{-}X_4\text{-}X_5\text{-}X_6\text{-}X_7\text{-}L_4\text{-}L_5\text{-}L_6 \quad \text{(formula II)}$$

wherein $L_1$, $L_2$, $L_3$, $L_4$, $L_5$ and $L_6$ are independently a flexible amino acid; and
wherein $L_1$, $L_2$, $L_3$, $L_4$, $L_5$ and $L_6$ are independently optionally absent or present.

It is also envisioned that additionally $L_1$, $L_2$, $L_3$, $L_4$, $L_5$ and $L_6$ are independently selected from A (Ala), L (Leu), G (Gly), S (Ser) and T (Thr). It is further envisioned that in the insertion sequence as described herein one of $X_{1A}$ or $X_{1B}$ is present and the other one of $X_{1A}$ or $X_{1B}$ is absent, and that within formula (II) all of $L_1$, $L_2$, $L_3$, $L_4$ and $L_5$ are present, and wherein $L_6$ is absent.

Thus, the insertion sequence including flexible amino acids can have a length of 7 to 14 amino acids. The insertion sequence including flexible amino acids can thus have a length of 7, 8, 9, 10, 11, 12, 13, or 14 amino acids. However, when more flexible amino acids are present, then the insertion sequence including the flexible amino acids can also have a length of 15, 16, 17, 18, 19, 20 or more amino acids.

It is also envisioned that the AAV or the AAV VP1 capsid protein of the present invention comprises an insertion sequence as described herein, in which $X_{1A}$ and/or $X_{1B}$ and/or $X_2$ and/or $X_3$ is/are not an acidic amino acid. Additionally or alternatively the insertion sequence as described herein does not comprise amino acid E (glutamate).

An "acidic amino acid" as used herein refers to amino acids D (Asp) and E (glutamate).

Additionally or alternatively the insertion sequence as used herein can comprise 1, 2, 3 or 4 acidic amino acids. For example, the insertion sequence can comprise one acidic amino acid. The amino acid can be D (Asp).

It is further envisioned that the AAV or the AAV VP1 capsid protein of the present invention comprises an insertion sequence as described herein, wherein one of $X_{1A}$ or $X_{1B}$ is present and the other one of $X_{1A}$ or $X_{1B}$ is absent and wherein $X_2$ is not a basic or acidic amino acid.

As used herein a "basic amino acid" is any one of K (Lys), R (Arg) and H (His).

It is further contemplated that the AAV or the AAV VP1 capsid protein of the present invention comprises an insertion sequence as described herein, which does not comprise a K (Lys) or H (His) at any position. It is also envisioned that the insertion sequence comprises R (Arg) as the only basic amino acid. Additionally, the insertion sequence can comprise D (Asp) as the only acidic amino acid.

It is further envisioned that the AAV or the AAV VP1 capsid protein of the present invention, which comprises an insertion sequence as described herein in which $X_{1A}$ and/or $X_{1B}$ and/or $X_2$ and/or $X_3$ and/or $X_4$ and/or $X_6$ is not a hydrophobic-aromatic amino acid.

A "hydrophobic amino acid" as described herein is an amino acid selected from F (Phe), W (Trp) or Y (Tyr).

It is also envisioned that the AAV or the AAV VP1 capsid protein of the present invention comprises an insertion sequence as described herein, which does not comprise any hydrophobic amino acid.

It is further contemplated that the AAV or the AAV VP1 capsid protein of the present invention comprises an insertion sequence as described herein, which does not comprise any one of the amino acids F (Phe), W (Trp), Y (Tyr), K (Lys), E (Glu), C (Cys), M (Met), I (Ile) and H (His).

Furthermore, it is contemplated that the AAV or the AAV VP1 capsid protein of the present invention comprises an insertion sequence as described herein, wherein $X_{1A}$ or $X_{1B}$ is a special amino acid, a hydrophobic aliphatic amino acid or polar amino acid with uncharged side group.

As used herein a "special amino acid" includes C (Cys), G (Gly) and P (Pro).

A "hydrophobic aliphatic amino acid" as used herein includes A (Ala), L (Leu), V (Val) and I (Ile).

A "polar amino acid with uncharged side group" as used herein comprises S (Ser), T (Thr), N (Asn) and Q (Gln).

Thus in the insertion sequence as described herein, $X_{1A}$ and/or $X_{1B}$ can be selected from A, L, V, I, S, T, N, Q, C, P and G. In the insertion sequence as described herein $X_{1A}$ and/or $X_{1B}$ can also be selected from G, P and N. In the insertion sequence as described herein $X_{1A}$ and/or $X_{1B}$ can also be selected from G, N, S and A.

In the insertion sequence as described herein $X_{1A}$ and/or $X_{1B}$ can also be any amino acid other than L, K, D, E, I, C, M, F, W, Y. In the insertion sequence as described herein $X_{1A}$ and/or $X_{1B}$ can also be any amino acid.

Additionally or alternatively the AAV or the AAV VP1 capsid protein of the present invention comprises an insertion sequence as described herein, wherein $X_2$ can be a hydrophobic aliphatic amino acid or polar amino acid with uncharged side group. Thus in the insertion sequence as described herein $X_2$ can be selected from S, T, N, Q, A, L, V and I. $X_2$ can also be selected from N and L. In the insertion sequence as described herein $X_2$ can also be selected from L, N, S and A. $X_2$ can also be any amino acid. In the insertion sequence as described herein $X_2$ can also be any amino acid other than D, E, I, C, M, F, W and Y.

Additionally or alternatively the AAV or the AAV VP1 capsid protein of the present invention comprises an insertion sequence as described herein, wherein $X_3$ can be selected from a hydrophobic aliphatic amino acid or special amino acid or polar amino acid with uncharged side group. Thus, in the insertion sequence as described herein $X_3$ can be selected from A, L, V, I, S, T, N, Q, C, G and P. In the insertion sequence as described herein $X_3$ can also be selected from S, Q and P. In the insertion sequence as described herein $X_3$ can also be selected from P, S, G and A. $X_3$ can also be P. In the insertion sequence as described herein $X_3$ can also be any amino acid. In the insertion sequence as described herein $X_3$ can also be any amino acid other than L, E, I, C, M, F, W and Y.

Additionally or alternatively the AAV or the AAV VP1 capsid protein of the present invention comprises an insertion sequence as described herein, wherein $X_4$ can be a hydrophobic aliphatic or basic or acidic amino acid or special amino acid or polar amino acid with uncharged side group. Thus in the insertion sequence as described herein $X_4$ can be selected from K, R, H, D, E, S, T, N, Q, A, V, I, L, C, G and P. In the insertion sequence as described herein $X_4$ can also be selected from P, A and T. In the insertion sequence as described herein $X_4$ can also be selected from P, T, S and G. In the insertion sequence as described herein $X_4$ can be selected from P or T. In the insertion sequence as described herein $X_4$ can be P. $X_4$ can be T. In the insertion sequence as described herein $X_4$ can also be any amino acid other than L, E, I, C, M, F, W and Y.

Additionally or alternatively the AAV or the AAV VP1 capsid protein of the present invention comprises an insertion sequence as described herein, wherein $X_6$ can be an acidic amino acid, a basic amino acid, a polar amino acid with uncharged side group or a special amino acid. Thus in the insertion sequence as described herein $X_6$ can be selected from K, R, H, D, E, S, T, N, Q, A, C, G and P. In the insertion sequence as described herein $X_6$ can also be selected from T, P and S. $X_6$ can also be selected from S, T, P and A. In the insertion sequence as described herein $X_6$ can also be selected from S, T, P and A. $X_6$ can also be selected from S or T. In the insertion sequence as described herein $X_6$ can be S. In the insertion sequence as described herein $X_6$ can be T.

The AAV or the AAV VP1 capsid protein of the present invention can also comprise an insertion sequence as described herein, wherein one of $X_{1A}$ or $X_{1B}$ is present and one of $X_{1A}$ or $X_{1B}$ is absent; and wherein $X_{1A}$ or $X_{1B}$ is selected from A, L, V, I, S, T, N, Q, C, P and G, preferably $X_{1A}$ or $X_{1B}$ is selected from G, P and N; and/or wherein $X_2$ is selected from S, T, N, Q, A, L, V and I, preferably $X_2$ is selected from N and L; and/or wherein $X_3$ is selected from A, L, V, I, S, T, N, Q, C, G and P, preferably $X_3$ is selected from S, Q and P; and/or wherein $X_4$ is selected from K, R, H, D, E, S, T, N, Q, A, V, I, L, C, G and P, preferably $X_4$ is selected from P, A and T; and/or wherein $X_6$ is selected from K, R, H, D, E, S, T, N, Q, A, C, G and P, preferably $X_6$ is selected from T, P and S.

The AAV of the present invention is capable to transduce retinal cells. Thus, use of the AAV of the present invention can result in that viral AAV DNA is present in mouse retinal nuclear extracts after 24 hours, when the AAV is administered intravenously into the tail vein of a C57-Bl6J (also written as C57BL/6J herein) mouse. Mice can be purchased from Charles River (http://www.crivercom/products-services/basic-research/find-a-model/jax-mice-strain-c57bl-6j?loc=DE).

The C57BL/6J inbred strain was created by Dr. CC Little from the mating of female 57 with male 52 from Miss Abbie Lathrop's stock. The same cross gave rise to the C57L and C57BR strains.

The skilled artesian knows the genotype of this mouse line and also knows where he can obtain such a mouse strain. The person skilled in the art also knows the differences between the substrains as described e.g. in Mekasa et al. (2009) "Genetic differences among C57BL/6 Substrains" Exp. Anim. 58(2), 141-149.

This mouse line is commercially available and can e.g. be obtained from Charles River Laboratories or Janvier labs.

In particular, a maximum of 8×10E10 genomic particles of an AAV library #1 as described elsewhere herein is injected into the tail vein of 4 week old C57-BL6J mice. 24 hours after intravenous injection into the tail vein, the retinal tissue is harvested as described herein elsewhere in detail. Afterwards, the genome of AAV with the ability to enter the nucleus of retinal cells within 24 hours after intravenous administration is amplified with PCR as described herein elsewhere in detail.

It is also envisioned that the AAV of present invention that viral AAV DNA is present in mouse retinal nuclear extracts after 24 hours, when the AAV is administered intravenously into the tail vein of a C57-Bl6J (C57/BL6J) mouse and that after determining the insertion sequence (selection round 1) and subcloning the detected insertion sequence in a further AAV, the viral DNA of the further AAV is present in mouse retinal nuclear extracts after 24 hours, when the AAV is administered intravenously into the tail vein of a C57-Bl6J (C57BL/6J) mouse (selection round 2). In the second selection round the same procedure as described herein for the first selection round and also in the Examples is followed.

To detect viral DNA in cones firstly virus as obtained in selection round 1 and 2 as described herein is injected into the tail vein of a 4 week old C57BL6J mouse or a RG-eGFP mouse line R685933 as described herein.

At most 5×10^11 genomic particles obtained from the second selection round as described herein are injected into the tail vein of a 4 week old C57BL6J or RG-eGFP mouse line R685933 as described herein.

The RG-eGFP mice (line R685933) are described by Fei and Hughes (2001) "Transgenic expression of the jellyfish green fluorescent protein in the cone photoreceptors of the mouse." Vis Neurosci. 18(4):615-23. The RG-eGFP mice (line R685933) can be purchased from MMRRC (https://www.mmrrc.org/catalog/sds.php?mmrrc_id=43).

To detect viral DNA in rods 24 hours after injection mice are euthanized by cervical dislocation and the eye was proptosed by placing Dumont #7 curved forceps (Fine Science Tools, Heidelberg) around the rear part close to the optic nerve and applying gentle pressure. The cornea was cut along the equator with a sharp blade. Subsequently, the retina was detached from the retinal pigment epithelium (RPE) and removed from remaining eye tissue, together with the lens and the vitreous body, by gently pulling the forceps upwards. After rinsing the tissue in ice cold 0.1 M phosphate buffer (PB) and removing the lens and any remaining RPE cells with the forceps, the two retinas per mouse were pooled and transferred into an Eppendorf tube and immediately processed for isolation of rod photoreceptors. In particular, a papain dissociation was performed as described in (Feodorova et al. (2015) "Quick and reliable method for retina dissociation and separation of rod photoreceptor perikarya from adult mice." MethodsX 2:39-46) and rods were isolated by anti-CD73-based MACS sorting according to (Eberle et al. (2014) "Subretinal transplantation of MACS purified photoreceptor precursor cells into the adult mouse retina." J. Vis. Exp. 84:e50932). Rod nuclei were isolated (to ensure that only nuclear DNA was analyzed) from MACS-sorted rods using the Subcellular Protein Fractionation Kit for Tissues (Thermo Fischer Scientific, #87790). Nuclear DNA was isolated using the DNeasy Blood & Tissue Kit (Qiagen, #69504). Sequencing with a Roche 454 sequencing system was performed to determine the inserted peptide sequences most predominantly found in rods. Additionally or alternatively the AAV of the present invention is such that viral AAV DNA is present in MAC-sorted rods using anti-CD73-coated magnetic beads and/or FACS-sorted cones, wherein the cones express eGFP and are FACS sorted based on their eGFP expression, 24 hours after administration, when the AAV is administered intravenously into the tail vein of a C57BL/6J mouse.

To detect viral AAV DNA in cones 24 hours after injection mice are euthanized by cervical dislocation and the eye was proptosed by placing Dumont #7 curved forceps (Fine Science Tools, Heidelberg) around the rear part close to the optic nerve and applying gentle pressure. The cornea was cut along the equator with a sharp blade. Subsequently, the retina was detached from the retinal pigment epithelium (RPE) and removed from remaining eye tissue, together with the lens and the vitreous body, by gently pulling the forceps upwards. After rinsing the tissue in ice cold 0.1 M phosphate buffer (PB) and removing the lens and any remaining RPE cells with the forceps, the two retinas per mouse were pooled and transferred into an Eppendorf tube and immediately processed for isolation of cone photoreceptors. In particular, a papain dissociation was performed as described in (Feodorova et al. (2015) "Quick and reliable method for retina dissociation and separation of rod photoreceptor perikarya from adult mice." MethodsX 2:39-46) and cones were FACS sorted (marker eGFP) according to (Becirovic et al. (2016) In Vivo Analysis of Disease-Associated Point Mutations Unveils Profound Differences in mRNA Splicing of Peripherin-2 in Rod and Cone Photoreceptors." PLOS Genetics 12(1):e1005811). Cone nuclei were isolated (to ensure that only nuclear DNA was analyzed) from FACS-sorted cones using the Subcellular Protein Fractionation Kit for Tissues (Thermo Fischer Scientific, #87790). Nuclear DNA was isolated using the DNeasy Blood & Tissue Kit (Qiagen, #69504). Sequencing with a Roche 454 sequencing system was performed to determine the inserted peptide sequences most predominantly found in cones.

Cone photoreceptors are FAC-sorted based on eGFP fluorescence from RG-eGFP mice line R685933 as described herein. Subsequently, viral DNA is isolated from the sorted rod and cone photoreceptors and sequenced using next-generation sequencing (NGS).

The present invention also relates to an AAV capsid comprising the AAV VP1 capsid protein of the present invention.

The present invention also relates to a virus vector comprising the AAV capsid of the present invention and a transgene, a molecule or a polypeptide, wherein the nucleic acid, molecule or the polypeptide are encapsidated by the AAV capsid. The nucleic acid, molecule or the polypeptide are optionally providing for a medical effect.

The present invention also relates to an AAV or viral vector of the present invention for use as a medicament. The present invention also relates to an AAV or the viral vector of the present invention for use in therapy.

For these purposes the AAV of the present invention may serve as a cargo system for other molecules. Non-limiting examples of such molecules are DNA, RNA, peptides, proteins or chemical compounds. Thus, the AAV used for therapy or used in the pharmaceutical composition as described herein can be a recombinant AAV as described herein. Such AAV can comprise a transgene.

The transgene can encode a product which is useful in biology and medicine, such as proteins, peptides, RNA, enzymes, or catalytic RNAs. Desirable RNA molecules include shRNA, tRNA, dsRNA, ribosomal RNA, catalytic RNAs, and antisense RNAs. One example of a useful RNA sequence is a sequence which extinguishes expression of a targeted nucleic acid sequence in the treated subject.

The rAAV or viral vector described herein can comprise a transgene such as a minigene. The minigene can be composed of, at a minimum, a heterologous nucleic acid sequence (the transgene), as described herein, and its regulatory sequences, and 5' and 3' AAV inverted terminal repeats (ITRs). It is this minigene that can be packaged into a capsid protein and delivered to a selected target cell.

The transgene can be e.g. a nucleic acid sequence, heterologous to the vector sequences flanking the transgene, which encodes a polypeptide, protein, or other product, of interest. The nucleic acid coding sequence can be operatively linked to regulatory components in a manner which permits transgene transcription, translation, and/or expression in a target cell. The heterologous nucleic acid sequence (transgene) can be derived from any organism. The AAV or viral vector may comprise one or more transgenes.

The composition of the transgene sequence will depend upon the use to which the resulting vector will be put. For example, the transgene is selected to provide optogenetic therapy. In optogenetic therapy, artificial photoreceptors are constructed by gene delivery of light-activated channels or pumps to surviving cell types in the remaining retinal circuit. This is particularly useful for patients, who have lost a significant amount of photoreceptor function, but whose bipolar cell circuitry to ganglion cells and optic nerve remains intact. In one embodiment, the heterologous nucleic acid sequence (transgene) can be an opsin. The opsin sequence can be derived from any suitable single- or multicellular-organism, including human, algae and bacteria. The opsin can e.g. be rhodopsin, photopsin, L/M wavelength (red/green)-opsin, or short wavelength (S) opsin (blue). In another embodiment, the opsin is channel rhodopsin or halo rhodopsin.

The transgene can also be selected for use in gene augmentation therapy, i.e., to provide replacement copy of a gene that is missing or defective. The transgene may be readily selected by one of skill in the art to provide the necessary replacement gene. In one embodiment, the missing/defective gene is related to an ocular disorder. The transgene can also be YX, GRM6, TRPM1L or GPR179 and the ocular disorder is Congenital Stationary Night Blindness. See, e.g., Zeitz et al, Am. J. Hum. Genet. 2013 Jan. 10; 92(I):67-75.

The transgene can also be selected for use in gene suppression therapy, i.e., expression of one or more native genes is interrupted or suppressed at transcriptional or translational levels. This can e.g. be accomplished using short hairpin RNA (shRNA) or other techniques well known in the art. See, e.g., Sun et al, Int. J. Cancer. 2010 Feb. 1; 126(3):764-74 and O'Reilly M, et al. Am. J. Hum. Genet. 2007 July; 81(1): 127-35. The transgene may be readily selected by one of skill in the art based upon the gene which is desired to be silenced.

The transgene can comprise more than one transgene. This may be accomplished using a single vector carrying two or more heterologous sequences, or using two or more AAV or viral vectors each carrying one or more heterologous sequences.

The AAV or the viral vector can also be used for gene suppression (or knockdown) and gene augmentation co-therapy. In knockdown/augmentation co-therapy, the defective copy of the gene of interest is silenced and a non-mutated copy is supplied. This can be accomplished using two or more coadministered vectors. See, Millington-Ward et al, Molecular Therapy, April 2011, 19(4): 642-649. The transgenes may be readily selected by one of skill in the art based on the desired result.

The transgene can be selected for use in gene correction therapy. This may be accomplished using, e.g., a zinc-finger nuclease (ZFN)-induced DNA double-strand break in conjunction with an exogenous DNA donor substrate as well as TALEN or CAS9/CRISPR systems in conjunction with exogenous RNA donor substrate. See, e.g., Ellis et al. (2013) "Zinc-finger nuclease-mediated gene correction using single AAV vector transduction and enhancement by Food and Drug Administration-approved drugs" Gene Ther. 20(1):35-42 and Singh, Braddick, Dhar (2017) 'Exploring the potential of genome editing CRISPR-Cas9 technology.' Gene; 599, pp. 1-18. The transgenes may be readily selected by one of skill in the art based on the desired result. For example, the Cas9 and multiple gRNAs can be packaged into separate AAV vectors, increasing overall packaging capacity but necessitating purification and co-infection of two AAVs.

The transgene can comprise or consist of reporter sequences, which upon expression produce a detectable signal. Such reporter sequences include, without limitation, DNA sequences encoding β-lactamase, β-galactosidase (LacZ), alkaline phosphatase, thymidine kinase, green fluorescent protein (GFP), red fluorescent protein (RFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences as described herein, when associated with regulatory elements, which drive their expression, can provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

The transgene may be used to correct or ameliorate gene deficiencies (as in the applications discussed above), which may include deficiencies in which normal genes are expressed at less than normal levels or deficiencies in which the functional gene product is not expressed. A preferred type of transgene sequence encodes a therapeutic protein or polypeptide which is expressed in a target cell.

The invention further includes using multiple transgenes, e.g., to correct or ameliorate a gene defect caused by a multi-subunit protein. In certain situations, a different transgene may be used to encode each subunit of a protein, or to encode different peptides or proteins. This is desirable when the size of the DNA encoding the protein subunit is large. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases.

The regulatory sequences include conventional control elements which can be operably linked to the transgene in a manner which permits its transcription, translation and/or expression in a cell transfected with the vector or infected with the virus produced as described herein. As used herein, "operably linked" sequences include both expression control sequences that are contiguous with the gene of interest and expression control sequences that act in trans or at a distance to control the gene of interest.

Expression control sequences as used herein can include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters, are known in the art and may be utilized.

The regulatory sequences useful in the AAVs provided herein may also contain an intron, desirably located between the promoter/enhancer sequence and the gene. One desirable intron sequence is derived from SV-40, and is a 100 bp mini-intron splice donor/splice acceptor referred to as SD-SA. Another suitable sequence includes the woodchuck hepatitis virus post- transcriptional element. (See, e.g., L. Wang and I. Verma, 1999 Proc. Natl. Acad. Sci., USA, 96:3906-3910). PolyA signals may be derived from many suitable species, including, without limitation SV-40, human and bovine.

Another regulatory component of the AAV described herein is an internal ribosome entry site (IRES). An IRES sequence, or other suitable systems, may be used to produce more than one polypeptide from a single gene transcript. An IRES (or other suitable sequence) is used to produce a protein that contains more than one polypeptide chain or to express two different proteins from or within the same cell. An exemplary IRES is the poliovirus internal ribosome entry sequence, which supports transgene expression in photoreceptors, RPE and ganglion cells. Preferably, the IRES is located 3' to the transgene in the rAAV vector.

The AAV of the present invention can comprise a promoter (or a functional fragment of a promoter). The selection of the promoter to be employed in the AAV may be made from among a wide number of constitutive or inducible promoters that can express the selected transgene in the desired target cell. The target cell can be a photoreceptor cell. The promoter may be derived from any species, including human. Desirably, the promoter can be "cell specific". The term "cell-specific" means that the particular promoter selected for the recombinant vector can direct expression of the selected transgene in a particular cell or ocular cell type. Useful promoters include, without limitation, the rod opsin promoter (RHO), the red-green opsin promoter, the blue opsin promoter, the cGMP-Phosphodiesterase promoter, the SWS promoter (blue short wavelength-sensitive (SWS) opsin promoter), the mouse opsin promoter (Beltran et al 2010 cited above), the rhodopsin promoter (Mussolino et al, Gene Ther, July 2011, 18(7):637-45); the alpha-subunit of cone transducin (Morrissey et al, BMC Dev, Biol, January 2011, 11:3); the cone arrestin (ARR3) promoter (Kahle N A et al., Hum Gene Ther Clin Dev, September 2018, 29(3): 121-131), the beta phosphodiesterase (PDE) promoter; the retinitis pigmentosa (RP1) promoter (Nicord et al, J. Gene Med, December 2007, 9(12): 1015-23); the NXNL2/NXNL 1 promoter (Lambard et al, PLoS One, October 2010, 5(10):e13025), the RPE65 promoter; the retinal degeneration slow/peripherin 2 (Rds/perph2) promoter (Cai et al, Exp Eye Res. 2010 August; 91(2): 186-94); the VMD2 promoter (Achi et al, Human Gene Therapy, 2009 (20:31-9)), and the ABCA4 promoter.

Selection of these and other common vector and regulatory elements are conventional and many such sequences are available. See, e.g., Sambrook et al, and references cited therein at, for example, pages 3.18-3.26 and 16.17-16.27 and Ausubel et al., Current Protocols in Molecular Biology, John Wiley & Sons, New York, 1989). Of course, not all vectors and expression control sequences will function equally well to express all of the transgenes as described herein. However, one of skill in the art may make a selection among these, and other, expression control sequences without departing from the scope of this invention.

Generally therapy or treatment or prevention of a disease comprises administering to a mammalian subject in need thereof, an effective amount of a composition comprising a rAAV or viral vector described herein, e.g. carrying a nucleic acid sequence encoding transgene, or fragment thereof, under the control of regulatory sequences which express the product of the gene in the subject's ocular cells, and optionally further a pharmaceutically acceptable carrier.

The present invention also relates to a pharmaceutical composition comprising an AAV or viral vector as described herein. Such pharmaceutical compositions can further comprise a carrier, preferably a pharmaceutically acceptable carrier. The pharmaceutical composition can be in the form of an injectable solution. The injectable solutions or suspensions may be formulated according to known art, using suitable non-toxic, pharmaceutically acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

For injectable formulations, the pharmaceutical compositions can be in lyophilized powder in admixture with suitable excipients in a suitable vial or tube. Before use in the clinic, the drugs may be reconstituted by dissolving the lyophilized powder in a suitable solvent system to form a composition suitable for intravenous or intramuscular injection or for subretinal, intravitreal or subconjunctival injection.

It is also envisaged that the pharmaceutical composition of the present invention is formulated/administered as eye drops.

The AAV of the present invention or the pharmaceutical composition of the present invention can be administered in a therapeutically effective amount. The "therapeutically effective amount" for the AAV can vary with factors including but not limited to stability of the active compound in the patient's body, the severity of the conditions to be alleviated, the total weight of the patient treated, the route of administration, the ease of absorption, distribution, and excretion of the active compound by the body, the age and sensitivity of the patient to be treated, adverse events, and the like, as will be apparent to a skilled artisan. The amount of administration can be adjusted as the various factors change over time.

In principle the AAV/pharmaceutical composition of the present invention can be administered in any suitable way. The AAV of the present invention e.g. comprising the desired transgene for use in the target photoreceptor cells can be formulated into a pharmaceutical composition intended for subretinal or intravitreal injection. Other forms of administration that may be useful in the methods described herein include, but are not limited to, direct delivery to a desired organ (e.g., the eye e.g. eye drops), oral, inhalation, intranasal, intratracheal, intravenous, intramuscular, subcutaneous, intradermal, and other parental routes of administration. Routes of administration may be combined, if desired.

Furthermore, it may be desirable to perform non-invasive retinal imaging and functional studies to identify areas of specific ocular cells to be targeted for therapy.

The AAV may be administered in a physiologically acceptable carrier to a subject, as described herein. The concentration of AAV in the pharmaceutical composition or upon administration can be between 10E8 and 10E12 total vector genomes per µl, preferably between 6×10E8 and 6×0E9 per µl. The AAV can also be administered in a concentration of about 10E9 vector genomes per µl.

The AAV of the present invention may be administered alone or in combination with other treatments. Thus, also the pharmaceutical composition may additionally or alternatively comprise one or more further active ingredients.

The pharmaceutical composition/AAV for the use of the invention can administered to a subject. The AAV and pharmaceutical compositions as described herein are applicable for both human therapy and veterinary applications. The subject can be a mammal or a bird. Examples of suitable mammals include, but are not limited to, a mouse, a rat, a cow, a goat, a sheep, a pig, a dog, a cat, a horse, a guinea pig, a canine, a hamster, a mink, a seal, a whale, a camel, a chimpanzee, a rhesus monkey and a human, with human being preferred. Examples of suitable birds include, but are not limited to, a turkey, a chicken, a goose, a duck, a teal, a mallard, a starling, a Northern pintail, a gull, a swan, a Guinea fowl or water fowl to name a few. The pharmaceutical composition may additionally comprise a pharmaceutically acceptable carrier.

The present invention also relates to an AAV of the present invention for use in treating a photoreceptor cell disease. In these embodiments the AAV (e.g. rAAV) or viral vector may comprise a heterologous nucleic acid encoding a therapeutic polypeptide, a therapeutic nucleic acid, a therapeutic protein/polypeptide or therapeutic molecule.

The present invention further relates to a method of treating a subject (e.g. preferably, a subject in need thereof), the method comprising administering an AAV of the present invention. Preferably, the AAV is administered in a therapeutically effective amount.

The AAV of the present invention could also be used in an in vitro diagnostic method. Thus, the present invention also relates to a method for diagnosis, the method comprising contacting the AAV of the present invention with a sample that has been obtained from a subject.

The present invention also relates to the manufacture of a medicament, the medicament comprising the AAV of the present invention.

The present invention also relates to a preparation comprising the AAV of the present invention.

The heterologous nucleic acid can be under the control of a promoter sequence that is expressed in the retina. The heterologous nucleic acid can be operably linked to a promoter suitable for expression of the therapeutic polypeptide or therapeutic nucleic acid in one or more retina cell types such as rods and cones. For example, the promoter can be a rhodopsin kinase (RK) promoter, an opsin promoter, a Cytomegalovirus (CMV) promoter, a chicken β-actin (CBA) promoter.

The AAV of the present invention can comprise a heterologous nucleic acid for delivery of the heterologous nucleic acid to the photoreceptor cells of a subject.

The heterologous nucleic acid therapeutic nucleic acid, a therapeutic protein/polypeptide or therapeutic molecule can be used to treat an ocular disorder selected from the group consisting of: autosomal recessive severe early-onset retinal degeneration (Leber's Congenital Amaurosis), congenital achromatopsia, Stargardt's disease, Best' s disease, Doyne's disease, cone dystrophy, retinitis pigmentosa, X-linked retinoschisis, Usher's syndrome, age related macular degeneration, atrophic age related macular degeneration, neovascular AMD, diabetic maculopathy, proliferative diabetic retinopathy (PDR), cystoid macular oedema, central serous retinopathy, retinal detachment, intra-ocular inflammation, glaucoma, and posterior uveitis.

The photoreceptor cells disease as described herein can be any disease affecting the photoreceptor cells such as the rods and/or cones. Non-limiting examples of a photoreceptor cell disease include blindness, achromatopsia, age-related macular degeneration, retinal degeneration, retinal dystrophy, retinitis pigmentosa, cone dystrophy, rod-cone dystrophy, color blindness, macular degeneration, night blindness, retinoschisis, choroideremia, diabetic retinopathy, hereditary optic neuropathy, Oguchi disease type I, retinitis punctata albescens (RPA), progressive retinal atrophy (PRA), fundus albipunctatus (FA) or congenital stationary night blindness (CSNB).

The present invention also relates to an in vitro use of an AAV or viral vector of the present invention for transduction of the nucleus of retinal cells.

The present invention also relates to a method for screening an insertion sequence, the method comprising
i) intravenously administering an AAV library, wherein each AAV comprises an insertion sequence, into a subject;

ii) isolating viral AAV DNA from retinal nuclear extracts;
iii) determining the sequence of the insertion sequence, thereby obtaining the insertion sequence.

The present invention also relates to a method for screening an insertion sequence, the method comprising
i) intravenously administering an AAV library, wherein each AAV comprises an insertion sequence, into a subject;
ii) isolating viral AAV DNA from retinal nuclear extracts;
iii) subcloning the isolated viral AAV DNA into a second AAV library;
iv) intravenously administering the second AAV library as obtained in step iii) into a subject;
v) isolating viral AAV DNA from rod or cone photoreceptors;
vi) determining the sequence of the insertion sequence, thereby obtaining the insertion sequence.

In the method for screening an insertion sequence as described herein steps i), ii) and iii) can be repeated.

The AAV library is the viral library as described elsewhere herein. The subcloning was performed as described elsewhere herein.

The present invention also relates to a peptide (insertion sequence) obtainable by the method of screening as described herein.

The present invention also relates to a kit comprising an AAV of the present invention or a pharmaceutical composition of the present invention. The kit can further comprise one or more of
(i) buffer(s);
(ii) oligonucleotide(s);
(iii) active ingredients;
(iv) syringe(s) suitable for intravitreal injection.

The present invention also relates to a kit comprising an AAV of the present invention or a pharmaceutical composition of the present invention. The kit can further comprise one or more of
(i) buffer(s);
(ii) oligonucleotide(s);
(iii) active ingredients;
(iv) a container suitable for providing eye drops.

The present invention also relates to a syringe suitable for intravitreal injection comprising a solution comprising the AAV or viral vector of the present invention or comprising the pharmaceutical composition of the present invention.

The present invention also provides for a method for generating an AAV of the present invention. For example, the AAV can be generated by culturing a host cell which contains a nucleic acid sequence encoding an AAV capsid protein as described herein, or fragment thereof; a functional rep gene; composed of, at a minimum, AAV inverted terminal repeats (ITRs) and optionally a heterologous nucleic acid sequence encoding a desirable transgene; and sufficient helper functions to permit packaging into the AAV capsid protein. The components required to be cultured in the host cell to package an AAV in an AAV capsid may be provided to the host cell in trans. Alternatively, any one or more of the required components (e.g., rep sequences, cap sequences, and/or helper functions) may be provided by a stable host cell which has been engineered to contain one or more of the required components using methods known to those of skill in the art.

Most suitably, such a stable host cell will contain the required component(s) under the control of an inducible promoter. However, the required component(s) may be under the control of a constitutive promoter. Examples of suitable inducible and constitutive promoters are provided herein. In still another alternative, a selected stable host cell may contain selected component(s) under the control of a constitutive promoter and other selected component(s) under the control of one or more inducible promoters. For example, a stable host cell may be generated which is derived from HEK293 cells (which contain E1 helper functions under the control of a constitutive promoter), but which contains the rep and/or cap proteins under the control of inducible promoters. Still other stable host cells may be generated by one of skill in the art.

The rep sequences, cap sequences, and helper functions required for producing the rAAV described herein may be delivered to the packaging host cell in the form of any genetic element which transfers the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, 1993 J. Virol, 70:520-532 and U.S. Pat. No. 5,478,745, among others.

The present invention is further characterized by the following items:

1. An adeno-associated virus (AAV), the AAV comprising an insertion of at least 6-8 amino acids between the positions corresponding to position 587 and 588 of SEQ ID NO: 1, wherein the insertion sequence has from the N-terminus to the C-terminus the formula I:

$$X_{1A}\text{-}X_{1B}\text{-}X_2\text{-}X_3\text{-}X_4\text{-}X_5\text{-}X_6\text{-}X_7 \quad \text{(formula I)}$$

wherein $X_5$ is selected from P (Pro), L (Leu) and V (Val);
wherein $X_7$ is R (Arg);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present, or
wherein $X_5$ is selected from S (Ser) and T (Thr);
wherein $X_7$ is S (Ser);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present, or
wherein $X_5$ is selected from A (Ala) and Q (Gln);
wherein $X_7$ is A (Ala);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present,
wherein viral AAV DNA is present in mouse retinal nuclear extracts after 24 hours, when the AAV is administered intravenously into the tail vein of a C57-Bl6J mouse, and
wherein viral AAV DNA is present in MAC-sorted rods using anti-CD73-coated magnetic beads and/or FACS-sorted cones, wherein the cones express eGFP and are FACS sorted based on their eGFP expression, 24 hours after administration, when the AAV is administered intravenously into the tail vein of a C57-Bl6J mouse for rod sorting and into the tail vein of RG-eGFP mice line R685933 for cone sorting.

2. An adeno-associated virus (AAV), the AAV comprising an insertion of at least 6-8 amino acids between the positions corresponding to position 587 and 588 of SEQ ID NO: 1

(insertion sequence); wherein the insertion sequence has from the N-terminus to the C-terminus the formula 1:

$$X_{1A}\text{-}X_{1B}\text{-}X_2\text{-}X_3\text{-}X_4\text{-}X_5\text{-}X_6\text{-}X_7 \qquad \text{(formula I)},$$

wherein $X_5$ is selected from P (Pro), L (Leu) and V (Val);
wherein $X_7$ is R (Arg);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present, wherein optionally viral AAV DNA is present in mouse retinal nuclear extracts after 24 hours, when the AAV is administered intravenously into the tail vein of a C57-Bl6J mouse.

3. An adeno-associated virus (AAV), the AAV comprising an insertion of at least 6-8 amino acids between the positions corresponding to position 587 and 588 of SEQ ID NO: 1, wherein the insertion sequence has from the N-terminus to the C-terminus the formula I:

$$X_{1A}\text{-}X_{1B}\text{-}X_2\text{-}X_3\text{-}X_4\text{-}X_5\text{-}X_6\text{-}X_7 \qquad \text{(formula I)},$$

wherein $X_5$ is selected from S (Ser) and T (Thr);
wherein $X_7$ is S (Ser);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present, wherein optionally viral AAV DNA is present in mouse retinal nuclear extracts after 24 hours, when the AAV is administered intravenously into the tail vein of a C57-Bl6J mouse.

4. An adeno-associated virus (AAV), the AAV comprising an insertion of at least 6-8 amino acids between the positions corresponding to position 587 and 588 of SEQ ID NO: 1, wherein the insertion sequence has from the N-terminus to the C-terminus the formula 1:

$$X_{1A}\text{-}X_{1B}\text{-}X_2\text{-}X_3\text{-}X_4\text{-}X_5\text{-}X_6\text{-}X_7 \qquad \text{(formula I)},$$

wherein $X_5$ is selected from A (Ala) and Q (Gln);
wherein $X_7$ is A (Ala);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present, wherein optionally viral AAV DNA is present in mouse retinal nuclear extracts after 24 hours, when the AAV is administered intravenously into the tail vein of a C57-Bl6J mouse.

5. An adeno-associated virus (AAV) VP1 capsid protein, the AAV VP1 capsid protein comprising an insertion of at least 6-8 amino acids between the positions corresponding to position 587 and 588 of SEQ ID NO: 1 (insertion sequence), wherein the insertion sequence has from the N-terminus to the C-terminus the formula I:

$$X_{1A}\text{-}X_{1B}\text{-}X_2\text{-}X_3\text{-}X_4\text{-}X_5\text{-}X_6\text{-}X_7 \qquad \text{(formula I)},$$

wherein $X_5$ is selected from P (Pro), L (Leu) and V (Val);
wherein $X_7$ is R (Arg);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present.

6. An adeno-associated virus (AAV) VP1 capsid protein, the AAV VP1 capsid protein comprising an insertion of at least 6-8 amino acids between the positions corresponding to position 587 and 588 of SEQ ID NO: 1, wherein the insertion sequence has from the N-terminus to the C-terminus the formula I:

$$X_{1A}\text{-}X_{1B}\text{-}X_2\text{-}X_3\text{-}X_4\text{-}X_5\text{-}X_6\text{-}X_7 \qquad \text{(formula I)},$$

wherein $X_5$ is selected from S (Ser) and T (Thr);
wherein $X_7$ is S (Ser);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present.

7. An adeno-associated virus (AAV) VP1 capsid protein, the AAV VP1 capsid protein comprising an insertion of at least 6-8 amino acids between the positions corresponding to position 587 and 588 of SEQ ID NO: 1, wherein the insertion sequence has from the N-terminus to the C-terminus the formula I:

$$X_{1A}\text{-}X_{1B}\text{-}X_2\text{-}X_3\text{-}X_4\text{-}X_5\text{-}X_6\text{-}X_7 \qquad \text{(formula I)},$$

wherein $X_5$ is selected from A (Ala) and Q (Gln);
wherein $X_7$ is A (Ala);
wherein $X_{1A}$, $X_{1B}$, $X_2$, $X_3$, $X_4$, $X_6$ are independently any amino acid;
wherein $X_{1A}$ and/or $X_{1B}$ are independently optionally absent or present.

8. The AAV or the AAV2 capsid protein of any one of items 1-7, wherein $X_{1A}$ is absent and $X_{1B}$ is present or wherein $X_{1B}$ is absent and $X_{1A}$ is present.

9. The AAV or the AAV VP1 capsid protein of any one of items 1-8, wherein the insertion sequence has from the N-terminus to the C-terminus the formula II:

$$L_3\text{-}L_2\text{-}L_1\text{-}X_{1A}\text{-}X_{1B}\text{-}X_2\text{-}X_3\text{-}X_4\text{-}X_5\text{-}X_6\text{-}X_7\text{-}L_4\text{-}L_5\text{-}L_6 \qquad \text{(formula II)},$$

wherein L is a flexible amino acid; and
wherein $L_1$, $L_2$, $L_3$, $L_4$, $L_5$ and $L_6$ are independently selected from Ala, Leu, Gly, Ser and Thr; and
wherein $L_1$, $L_2$, $L_3$, $L_4$, $L_5$ and $L_6$ are independently optionally absent or present.

10. The AAV or the AAV VP1 capsid protein of any one of the preceding items, wherein one of $X_{1A}$ or $X_{1B}$ is present and the other one of $X_{1A}$ or $X_{1B}$ is absent, and wherein all of $L_1$, $L_2$, $L_3$, $L_4$ and $L_5$ are present, and wherein $L_6$ is absent.

11. The AAV or the AAV2 capsid protein of any one of the preceding items, wherein $X_{1A}$ and/or $X_{1B}$ and/or $X_2$ and/or $X_3$ is not an acidic amino acid.

12. The AAV or the AAV VP1 capsid protein of any one of the preceding items, wherein one of $X_{1A}$ or $X_{1B}$ is present and the other one of $X_{1A}$ or $X_{1B}$ is absent and wherein $X_2$ is not a basic or acidic amino acid.

13. The AAV or the AAV VP1 capsid protein of any one of the preceding items, wherein $X_{1A}$ and/or $X_{1B}$ and/or $X_2$ and/or $X_3$ and/or $X_4$ and/or $X_6$ is not a hydrophobic-aromatic amino acid.

14. The AAV or the AAV VP1 capsid protein of any one of the preceding items, wherein one of $X_{1A}$ or $X_{1B}$ is present and one of $X_{1A}$ or $X_{1B}$ is absent; and
wherein $X_{1A}$ or $X_{1B}$ is selected from A, L, V, I, S, T, N, Q, C, P and G, preferably $X_{1A}$ or $X_{1B}$ is selected from G, P and N and/or
wherein $X_2$ is selected from S, T, N, Q, A, L, V and I, preferably $X_2$ is selected from N and L; and/or
wherein $X_3$ is selected from A, L, V, I, S, T, N, Q, C, G and P, preferably $X_3$ is selected from S, Q and P; and/or
wherein $X_4$ is selected from K, R, H, D, E, S, T, N, Q, A, V, I, L, C, G and P, preferably $X_4$ is selected from P, A and T; and/or
wherein $X_6$ is selected from K, R, H, D, E, S, T, N, Q, A, C, G and P, preferably $X_6$ is selected from T, P and S.

15. The AAV or the AAV VP1 capsid protein of any one of the preceding items for use as a medicament/treating a disease.

16. The AAV of any one of the preceding items for use in treating a photoreceptor cell disease.

17. An AAV capsid comprising the AAV VP1 capsid protein of any one of the preceding items and optionally further comprising one or more of AAV capsid protein VP2 and/or VP3.

18. A virus vector comprising the AAV capsid of item 17 and a transgene, molecule or a polypeptide, wherein the transgene, molecule or the polypeptide are encapsidated by the AAV capsid.

19. Pharmaceutical composition comprising the AAV or the virus vector of any one of the preceding items.

20. In vitro use of an AAV or of the virus vector of any one of items 1-18 for transduction of the nucleus of retinal cells.

21. A method for screening an insertion sequence, the method comprising
i) intravenously administering an AAV library, wherein each AAV comprises an insertion sequence, into a subject;
ii) isolating viral AAV DNA from retinal nuclear extracts;
iii) subcloning the isolated viral AAV DNA into a second AAV library;
iv) intravenously administering the second AAV library as obtained in step iii) into a subject;
v) isolating viral DNA from rod or cone photoreceptors;
vi) determining the sequence of the insertion sequence, thereby obtaining the insertion sequence.

22. A peptide (insertion sequence) obtainable by the method of item 21.

23. Kit comprising an AAV or the virus vector of any one of items 1-18.

24. The virus vector of any one of the preceding items for use as a medicament/treating a disease.

25. The virus vector of any one of the preceding items for use in treating a photoreceptor cell disease.

Genomic sequences and VP1 protein sequences of different AAVs as described herein.

TABLE 1

Genomic sequences and VP1 protein sequences of different AAVs.

| | Uniprot Number; sequence version (last modified) | NCBI Reference Sequence incl. version number |
|---|---|---|
| AAV1 sequence (complete genome) | | NC_002077.1 |
| AAV1 VP1 sequence | | |
| AAV2 sequence | | NC_001401.2 |
| AAV2 VP1 sequence | SEQ ID No. 1 | |
| AAV3 sequence (complete genome) | | NC_001729.1 |
| AAV3 VP1 sequence | Q65311-1; Nov. 1, 1996 - v1 | |
| AAV3b sequence (complete genome) | | AF028705.1 |
| AAV3B VP1 sequence | | AAB95452.1 |
| AAV4 sequence (complete genome) | | NC_001829.1 |
| AAV4 VP1 sequence | O41855-1; Jan. 1, 1998 - v1 | |
| AAV5 sequence | | NC_006152.1 |
| AAV5 VP1 sequence | Q9YIJ1-1; May 1, 1999 - v1 | |
| AAV6 sequence | | AF028704.1 |
| AAV6 VP1 sequence | O56137-1; Jun. 1, 1998 - v1 | AAB95450.1 |
| AAV7 sequence | | NC_006260.1 |
| AAV7 VP1 sequence | Q8JQG0-1; Oct. 1, 2002 - v1 | |
| AAV8 sequence | | NC_006261.1 |
| AAV8 VP1 sequence | Q8JQF8-1; Oct. 1, 2002 - v1 | |
| AAV9 sequence | | AX753250.1 |
| AAV9 VP1 sequence | | AAS99264.1 |
| AAV10 sequence | | |
| AAV10 VP1 sequence | Q5Y9B4-1; Nov. 23, 2004 - v1 | |
| AAV11 sequence | | |
| AAV11 VP1 sequence | Q5Y9B2-1; Nov. 23, 2004 - v1 | |
| AAV12 sequence | | |
| AAV12 VP1 sequence | A9RAI0-1; Feb. 5, 2008 - v1 | |
| AAV13 sequence | | |
| AAV13 VP1 sequence | B5SUY7-1; Nov. 4, 2008 - v1 | |

Sequences as used in the present invention.

TABLE 2

Sequences described herein.

| No. | Name | Sequence |
|---|---|---|
| 1 | Uniprot Number P03135 CAPSD_AAV2S Capsid protein VP1 OS = Adeno-associated virus 2 (isolate Srivastava/1982) | MAADGYLPDWLEDTLSEGIRQWWKLKPGPPPPKPAERHKDDS RGLVLPGYKYLGPFNGLDKGEPVNEADAAALEHDKAYDRQLDS GDNPYLKYNHADAEFQERLKEDTSFGGNLGRAVFQAKKRVLE PLGLVEEPVKTAPGKKRPVEHSPVEPDSSSGTGKAGQQPARK RLNFGQTGDADSVPDPQPLGQPPAAPSGLGTNTMATGSGAPM ADNNEGADGVGNSSGNWHCDSTWMGDRVITTSTRTWALPTY NNHLYKQISSQSGASNDNHYFGYSTPWGYFDFNRFHCHFSPR DWQRLINNNWGFRPKRLNFKLFNIQVKEVTQNDGTTTIANNLTS TVQVFTDSEYQLPYVLGSAHQGCLPPFPADVFMVPQYGYLTLN NGSQAVGRSSFYCLEYFPSQMLRTGNNFTFSYTFEDVPFHSSY AHSQSLDRLMNPLIDQYLYYLSRTNTPSGTTTQSRLQFSQAGA SDIRDQSRNWLPGCYRQQRVSKTSADNNNSEYSWTGATKYH LNGRDSLVNPGPAMASHKDDEEKFFPQSGVLIFGKQGSEKTNV DIEKVMITDEEEIRTTNPVATEQYGSVSTNLQRGNRQAATADVN |

TABLE 2 -continued

Sequences described herein.

| No. | Name | Sequence |
|---|---|---|
|  | GN = VP1<br>PE = 1<br>SV = 2<br>Last modified: April 5, 2011-v2 | TQGVLPGMVWQDRDVYLQGPIWAKIPHTDGHFHPSPLMGGFG<br>LKHPPPQILIKNTPVPANPSTTFSAAKFASFITQYSTGQVSVEIE<br>WELQKENSKRWNPEIQYTSNYNKSVNVDFTVDTNGVYSEPRPI<br>GTRYLTRNL<br>(positions 487 and 488 are highlighted in the above sequence) |
| 2 | bottom strand | 5'-TTGGCGCGCCGCVNNVNNVNNVNNVNNVNNVNN<br>GGCGGCCGCTTTTTTCCTTGA-3'<br>wherein V = A or C or G and<br>N = A or C or G or T.<br>This selection of nucleic bases has been undertaken to have a lesser opportunity that stop sequences are generated. |
| 3 | primer | 5'CTCAAGGAAAAAAGC3' |
| 4 | primer | 5'-ATGTCCGTCCGTGTGTGG-3' |
| 5 | primer | 5'-GTATCTACCAACCTCCAGAGAG-3' |
| 6 | primer | 5'-GTGTTGACATCTGCGGTAGC-3' |
| 7 | single strand DNA oligo | 5'-CGCGGCCGCANNNNNNNNNNNNNNNNNNNNNGCCG-3'<br>wherein N = A or C or G or T |
| 8 | single strand DNA oligo | 5'-CGCGCGGCNNNNNNNNNNNNNNNNNNNNNTGCGGC-3'<br>wherein N = A or C or G or T |
| 9 | primer | 5'-CTTTGGGAAGCAAGGCTCAG-3' |
| 10 |  | GLSPPTR |
| 11 |  | SSPGLPR |
| 12 |  | NSTSVNR |
| 13 |  | VSSSLQR |
| 14 |  | PNQAPPR |
| 15 |  | NNPTPSR |
| 16 |  | GAHRSDS |
| 17 |  | RANQTSS |
| 18 |  | HSARTDS |
| 19 |  | SQNDSRS |
| 20 |  | NSRPAAA |
| 21 |  | RGSLQNA |
| 22 |  | GNRQ |
| 23 | 7m8 | LALGETTRP |

EXAMPLES

The following examples illustrate the invention. These examples should not be construed as to limit the scope of this invention. The examples are included for purposes of illustration and the present invention is limited only by the claims.

Example 1

Novel AAV Capsids

We performed an AAV peptide display selection to identify AAV with improved targeting to retinal cells. We used an AAV library of mutants displaying 7-mer random peptides (sometimes also 6-mer and 8-mer) at amino acid position 587 of the AAV2 capsid protein VP1 (Perabo et al. (2003)" In vitro selection of viral vectors with modified tropism: the adeno-associated virus display, Molecular therapy: the journal of the American Society of Gene Therapy 8, 151-157). The inserted peptides are flanked by 2-3 additional "flexible" amino acids (e.g. alanine) on either end (N-terminal and C-terminal). Amino acid position 587 is located at the tip of a peak at the capsid's threefold symmetry axis (Xie et al. (2002) "The atomic structure of adeno-associated virus (AAV-2), a vector for human gene therapy" Proceedings of the National Academy of Sciences of the United States of America 99, 10405-10410) and within the heparin sulfate proteoglycan (HSPG) binding site (Opie et al. (2003) "Identification of amino acid residues in the capsid proteins of adeno-associated virus type 2 that contribute to heparin sulfate proteoglycan binding, Journal of virology 77, 6995-7006 and Kern et al. (2003) "Identification of a heparin-binding motif on adeno-associated virus type 2 capsids" Journal of virology 77, 11072-11081).

Insertion of the 7-mers in this exposed position facilitates receptor binding of inserted peptides and disrupts the primary receptor-binding motif for HSPG (Perabo et al. (2006) "Heparan sulfate proteoglycan binding properties of adeno-associated virus retargeting mutants and consequences for their in vivo tropism" Journal of virology, 80, 7265-7269), which is essential in approaches aiming to redirect the viral tropism. In addition, the AAV library had been depleted for mutants binding to HSPG through the peptide sequence that had been inserted (Perabo et al. (2006) "Heparan sulfate proteoglycan binding properties of adeno-associated virus retargeting mutants and consequences for their in vivo tropism" Journal of virology, 80, 7265-7269) to minimize the presence of AAV baring secondary high affinity binding sites for HSPG (Sallach et al. (2014) "Tropism-modified AAV vectors overcome barriers to successful cutaneous therapy" Molecular therapy: the journal of the American Society of Gene Therapy 22, 929-939). 8×10E10 genomic particles of this AAV library (Library #1) were injected into the tail vein of 4 week old C57-BL6J mice. 24 hours later the retinal tissue was harvested and viral DNA was isolated from retinal nuclear extracts. The genome of AAV with the ability to enter the nucleus of retinal cells within 24 hours after intravenous administration was amplified with PCR and used to generate a second AAV library containing 7-mer insertions selected from the first round. 8×10E10 genomic particles of the second AAV library (Library #2) was then injected into the tail vein of 4 week old C57-BL6J mice. 24 hours later the retinal tissue (without RPE or extra-retinal tissue) was harvested and viral DNA was isolated from retinal nuclear extracts. After PCR-based amplification, the DNA sequence encoding the 7-mer AAV was determined and a third AAV library with these 7-mer insertions was generated. Next, 8×10E10 genomic particles of the third AAV library (Library #3) was injected into the tail vein of 4 week old C57-BL6J mice or of RG-eGFP line R685933 (Fei and Hughes (2001) "Transgenic expression of the jellyfish green fluorescent protein in the cone photoreceptors of the mouse" Visual neuroscience 18, 615-623) expressing eGFP in cone photoreceptors. 24 hours later, rod photoreceptors were MAC-sorted using anti-CD73-coated magnetic beads (Eberle et al. (2011) "integration of transplanted CD73-positive photoreceptor precursors into adult mouse retina" Investigative ophthalmology & visual science 52, 6462-6471) and cone photoreceptors were FAC-sorted based on eGFP fluorescence (Fei and Hughes (2001) "Transgenic expression of the jellyfish green fluorescent protein in the cone photoreceptors of the mouse" Visual neuroscience 18, 615-623). Subsequently, viral DNA was isolated from the sorted rod and cone photoreceptors and sequenced using next-generation sequencing (NGS). The following novel AAV with the listed peptide insertions in position 587 of AAV2 VP1 conferred the ability to target cells of the retina and transfer their genome into the nucleus of retinal cells within 24 hours after intravenous delivery could be identified (only variants with 2 or more NGS reads are listed, the variants with more than 20 NGS reads are marked in bold letters) see FIG. 1.

In addition, the following novel AAV with the listed peptide insertions in position 587 of AAV2 VP1 conferred the ability to target rod photoreceptors within 24 hours after intravenous delivery could be identified (only peptides with 2 or more NGS reads are listed, the variants with more than 20 NGS reads are marked in bold letters) (see FIG. 2).

Finally, the following novel AAVs with the listed peptide insertions in position 587 of AAV2 VP1 conferred the ability to target cone photoreceptors within 24 hours after intravenous delivery could be identified (only peptides with 2 or more NGS reads are listed, the AAVs with more than 20 NGS reads are marked in bold letters) (see FIG. 3).

Some of the identified variants contained putative integrin binding motifs like RGD, RGS or NGR. These AAVs carrying the indicated insertion sequences are summarized in FIG. 4.

Several AAVs were detected in more than one experiment. These overlapping AAV with the respective numbers of NGS reads are summarized in FIG. 5. Notably, for sequence 'RGSLQNA' it is indicated that the number of NGS reads from the whole retina would be 0. However, this is an error. The reason for this is that NGS reads are detected for rods and cones. These data can only be obtained when the insertion sequence was selected in selection rounds 1 and 2 before—the feature of both selection rounds being that DNA is detected in the retina. Thus, this insertion sequence must have been detected in the retina before as well.

Example 2

Biological Testing of nNovel AAV Capsids

Synthetic DNA oligos coding for selected peptide variants flanked by 2-3 alanines on either end were inserted into the AseI/MluI restriction sites of the AAV trans plasmid pRC99 (Nickiin et al. (2001) "Efficient and selective AAV2-mediated gene transfer directed to human vascular endothelial cells, Molecular therapy: the journal of the American Society of Gene Therapy 4, 174-181 and Girod et al. (1999) "Genetic capsid modifications allow efficient re-targeting of adeno-associated virus type 2", Nature medicine 5, 1052-

1056 expressing AAV2 Rep and Cap genes resulting in the generation of AAV2 VP1-3 open reading frame with the intended peptide insertions at a position corresponding to amino acid 587 of VP1. These modified pRC99 plasmids were used to produce AAV particles containing novel AAV capsid variants for biological testing. AAV production was performed by standard techniques described in (Michalakis et al. (2010) "Restoration of cone vision in the CNGA3−/− mouse model of congenital complete lack of cone photoreceptor function, Molecular therapy: the journal of the American Society of Gene Therapy, 18, 2057-2063). A self-complementary (sc) AAV eis plasmid containing a CMV-eGFP expression cassette (AAV-sc-CMV-eGFP) was used for packaging. Such AAV particles (6×10E8-6×10E9 total vector genomes) were then delivered into the vitreous (intravitreal injection of 1 pi AAV suspension) of adult wild type C56-BL6/J mice and the mice were subsequently examined using in vivo fluorescence fundus microscopy (confocal scanning laser ophthalmoscopy). Subsequently, the eyes were removed and the eye cups processed for histological analysis, eGFP fluorescence imaging and immunohistochemistry. FIGS. 6-9 illustrate the results.

Wildtype AAV2 serotyped vectors show only limited transduction efficiencies upon subretinal or intravitreal delivery (Lebherz et al. (2008) "Novel AAV serotypes for improved ocular gene transfer" The journal of gene medicine 10, 375-382, Auricchio et al. (2001) "Exchange of surface proteins impacts on viral vector cellular specificity and transduction characteristics: the retina as a model" Hum. Mol. Genet., 10, 3075-3081, Hellstrom et al. (2009) "Cellular tropism and transduction properties of seven adeno-associated viral vector serotypes in adult retina after intravitreal injection, Gene therapy 16, 521-532). In particular, AAV2 transduces primarily retinal pigment epithelial (rpe) cells from the subretinal compartment (Auricchio et al. (2001) "Exchange of surface proteins impacts on viral vector cellular specificity and transduction characteristics: the retina as a model" Hum. Mol. Genet. 10, 3075-3081 and Trapani et al. (2014) "Vector platforms for gene therapy of inherited retinopathies" Prog. Retin Eye Res.). From the intravitreal compartment AAV2 mainly transduces Müller glial cells and retinal ganglion cells (Auricchio et al. (2001) "Exchange of surface proteins impacts on viral vector cellular specificity and transduction characteristics: the retina as a model" Hum. Mol. Genet. 10, 3075-3081 and Trapani et al. (2014) "Vector platforms for gene therapy of inherited retinopathies" Prog. Retin Eye Res.).

For examples on intravitreal transduction see FIG. 2a in Hellstrom et al. (2009) "Cellular tropism and transduction properties of seven adeno-associated viral vector serotypes in adult retina after intravitreal injection, Gene therapy 16, 521-532 or FIG. 4a in Auricchio et al. (2001) "Exchange of surface proteins impacts on viral vector cellular specificity and transduction characteristics: the retina as a model" Hum. Mol. Genet. 10, 3075-3081. For example on subretinal transduction pattern see FIG. 4 in (Lebherz et al. (2008) "Novel AAV serotypes for improved ocular gene transfer" The journal of gene medicine 10, 375-382).

The specific modifications described here markedly changed the tropism and transduction behavior of our novel AAV capsid variants, which are now capable of transducing very efficiently multiple retinal cell types from the subretinal and the intravitreal compartments (see FIGS. 6-10). More importantly the novel AAV transduce very efficiently rod and cone photoreceptors from either the subretinal and/or the intravitreal compartment. In conclusion, the biological testing of selected novel AAV capsid variants suggests a markedly changed transduction behavior induced by our novel peptide insertions, which will be very useful for any kind of experiments aiming for efficient and high level transduction of specific retinal cell types in basic research or for the development of gene transfer-based treatments for ocular diseases (e.g. ocular gene therapy). In combination with cell type-specific promoters (e.g. cone or rod-specific promoter) the novel AAV capsid variants will allow for overcoming natural barriers for transduction and for targeting of specific cell types after systemic application or after intravitreal or subconjuctival delivery.

The transduction efficiency of our novel AAV capsid variants was further characterized in the in immortalized cone photoreceptor cell line 661w (Tan et al. (2004) "Expression of cone-photoreceptor-specific antigens in a cell line derived from retinal tumors in transgenic mice." Investigative Ophthalmology & Visual Science 45 764-768). For this, 661w grown at about 60% confluency were infected at a multiplicity of infection (MOI) of 100,000 viral genomes per cell with either the novel AAV capsids, wild-type AAV2 or the engineered AAV2 variant 7m8 (Dalkara et al. (2013) "In vivo-directed evolution of a new adeno-associated virus for therapeutic outer retinal gene delivery from the vitreous." Science Translational Medicine, 5(189) 189ra76), namely LALGETTRP (SEQ ID NO. 23) expressing eGFP under control of the CMV promoter. After 48 hours the eGFP fluorescence was determined using epifluorescence microscopy (EVOS FL cell imaging system, Thermo Fisher Scientific). Subsequently, the cells were fixed for 15 minutes with 4% paraformaldehyde in phosphate buffered saline (PBS), washed with and resuspended in PBS for flow cytometry-based analysis of eGFP signal (FACSCantoII system, BD Bioscience). The novel AAV capsid variants "NNPTPSR" and "GLSPPTR" showed superior transduction efficiency of 661w wells as compared to AAV2 or 7m8. FIGS. 11 illustrates the results.

All experiments so far were with modified AAV2 capsids. However, other AAV capsids also tolerate peptide insertions in the corresponding capsid positions (Michelfelder et al. (2011) "Peptide ligands incorporated into the threefold spike capsid domain to re-direct gene transduction of AAV8 and AAV9 in vivo" PloS one, 6, e23101), Therefore our novel peptide insertions can be transferred to the other known AAV capsid, e.g. into AAV8, AAV9, AAV7 or AAV5 which are known to have higher efficiency and broader transduction profiles in the retina compared to AAV2. Moreover, our novel AAV capsid peptide insertions can be combined with the capsid tyrosine, threonine and serine mutations (Petrs-Silva et al. (2009) "High-efficiency transduction of the mouse retina by tyrosine-mutant AAV serotype vectors" Molecular therapy: the journal of the American Society of Gene Therapy 17 463-471 and Zhong et al. (2008) "Next generation of adeno-associated virus 2 vectors: point mutations in tyrosines lead to high-efficiency transduction at lower doses" Proceedings of the National Academy of Sciences of the United States of America 105, 7827-7832) to reduce proteasome-mediated degradation and enhance transduction efficacy.

Example 3

Retinal Cross-Sections

To show that the AAV vectors as described herein truly transduce photoreceptors the AAV2 "GLSPPTR" capsid has been intravitreally applied to living mice. In particular, a single intravitreal injection of 1µl (containing approximately 2×10E9 vector genomes) of viral suspension of ss-mSWS-eGFP packaged with the AAV2 "GLSPPTR" capsid (see also Example 2) was intravitreally applied to 10 week old C57-BL6J mice. AAV-ss-mSWS-eGFP drives the expression of eGFP under control of the mouse SWS promoter. Then GFP expression of has been analyzed 6 weeks after. In this regard, confocal scanning microscopy images have been taken from the photoreceptor area of the eye. As can be seen in FIG. 12 eGFP can be detected in retinal cross sections from cone photoreceptors. Here, strong anti-eGFP immunosignal (grey) in cone photoreceptors was observed. Quantification of double-labeling with the cone marker cone arrestin revealed that 78,7 ±3,1% (n=4) of cone arrestin-positive cones were positive for eGFP. This experiment thus shows that the AAV specifically targets photoreceptors.

Example 4

Human Explants

To analyze if the AAV vectors as described in the Examples 1 and 2 will also transduce human photoreceptor cells, human explants have been analyzed. Post mortem human retinal tissue was cultured photoreceptor side down according to previously published methods (Fradot M et al. May 2011 Gene therapy in ophthalmology: validation on cultured retinal cells and explants from postmortem human eyes. Human gene therapy. 22(5):587-93). The human retinal tissue explant was transduced on day 0 by applying 1×10E11 total vg of sc-CMV-eGFP packaged with one of the novel AAV2 "GLSPPTR" or "NNPTPSR" capsid to the vitreal side of the retina and cultured for nine days in vitro (DIV). On DIV 9, culture medium was removed and tissue was fixed with 4% paraformaldehyde in phosphate buffered saline and subsequently processed for cryosectioning and native eGFP fluorescence imaging using confocal microscopy.

In FIG. 13 representative confocal scanning microscopy images showing AAV-mediated eGFP expression in human retinal explants are depicted (capsid peptide insertion sequences are given on top of each image column). Notably, strong native eGFP fluorescence (grey) in multiple retinal cell types and layers was observed. In particular, many photoreceptor inner segments (is) and cell bodies within the outer nuclear layer (onl) were eGFP positive. IS, inner segments. ONL, outer nuclear layer. INL, inner nuclear layer. ONL, inner nuclear layer. GCL, ganglion cell layer.

Example 5

ERG Measurements (Transgene Expression in Cones)

To analyze if the AAV vectors as obtained in example 1 and 2 are also efficient in providing a transgene to the photoreceptor cell, ERG measurements were performed. The electroretinogram (ERG) is a diagnostic test known to the skilled person that measures the electrical activity generated by neural and non-neuronal cells in the retina in response to a light stimulus. The electrical response is a result of a retinal potential generated by light-induced changes in the flux of transretinal ions, primarily sodium and potassium.

For this experiment Cnga3-deficient (CNGA3$^{-/-}$) mice have been utilized which have congenitally nonfunctional cone photoreceptor due to a genetic deletion in the cone photoreceptor cyclic nucleotide-gated (CNG) channel subunit CNGA3. AAV vectors of Example 2 were adapted to drive the expression of the mouse CNGA3 complementary DNA under control of a blue (short wavelength-sensitive, SWS) opsin promoter (ss-mSWS-mCnga3-WPRE) targeting cones. This technique is also described in (Michalakis et al. (2010) Restoration of Cone Vision in the CNGA3$^{-/-}$ Mouse Model of Congenital Complete Lack of Cone Photoreceptor Function Mol. Ther.: 2057-2063). The AAV2 was packaged with the "GLSPPTR" capsid as disclosed in Example 2. Approximately 1×10E10 total vg AAV particles were delivered intravitreally in 4 week old Cnga3-deficient mice.

Specifically, ERG measurement was performed 2 months after a single intravitreal injection of 1 µl (containing approximately 1×10E10 total vg of ss-mSWS-mCnga3-WPRE). Representative photopic flicker ERG measurements are shown in FIG. 14. Traces from the treated eye (black) and untreated control eye (dashed grey) at a stimulus of 3.1 log cd sec/m$^2$ and indicated frequency are shown therein.

Cnga3-deficient mice receiving the AAV vector comprising the transgene show an increase in amplitude. An increase in amplitude is indicative for cone system function improvement under photopic conditions, while untreated Cnga3-deficient mice do not respond to light stimulation (Michalakis et al. (2010) Restoration of Cone Vision in the CNGA3$^{-/-}$ Mouse Model of Congenital Complete Lack of Cone Photoreceptor Function Mol. Ther.: 2057-2063).

After the ERG measurement, treated and untreated control eyes were collected and processed for anti-CNGA3 immunohistological analysis of CNGA3 protein expression as described in (Michalakis et al. (2010) Restoration of Cone Vision in the CNGA3$^{-/-}$ Mouse Model of Congenital Complete Lack of Cone Photoreceptor Function Mol. Ther.: 2057-2063).

Representative data are shown in FIG. 15. In particular, confocal scanning microscopy images showing cone photoreceptor expression of CNGA3 protein on retinal cross sections from a 3 month old Cnga3-deficient mouse 2 months after a single intravitreal injection of 1 µl (containing approximately 1×10E10 total vg of ss-mSWS-mCnga3-WPRE (Michalakis et al. 2010 cited elsewhere herein) packaged with the novel AAV2 "GLSPPTR" capsid are depicted. Strong anti-CNGA3 immunosignal is found in peanut agglutinin (PNA) positive cone photoreceptors. os, outer segments. onl, outer nuclear layer. inl, inner nuclear layer. gcl, ganglion cell layer.

Example 6

ERG Measurements (Transgene Expression in Rods)

Similarly to example 5, FIG. 16 shows representative scotopic single flash ERG measurements from 3 month old Cnga3-deficient mice 2 months after a single intravitreal injection of 1 µl (containing approximately 1×10E10 total vg of ss-mRho-mCngb1-sv40 (Koch et al. (2012) Gene therapy restores vision and delays degeneration in the CNGB1−/− mouse model of retinitis pigmentosa. Hum. Mol. Genet.: 4486-4496) packaged with the novel AAV2 "NNPTPSR" capsid. Traces from the treated eye (black) and untreated control eye (dashed grey) at indicated light stimulus luminance are shown.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

REFERENCES

Altschul Nucl. Acids Res. 25 (1977), 3389-3402.
Altschul, J. Mol. Evol. 36 (1993), 290-300.
Altschul, J. Mol. Biol. 215 (1990), 403-410.
Auricchio et al. (2001) " Exchange of surface proteins impacts on viral vector cellular specificity and transduction characteristics: the retina as a model" Hum. Mol. Genet., 10, 3075-3081.
Ausubel et al., Current Protocols in Molecular Biology, John Wiley & Sons, New York, 1989
Becirovic et al. (2016) In Vivo Analysis of Disease-Associated Point Mutations Unveils Profound Differences in mRNA Splicing of Peripherin-2 in Rod and Cone Photoreceptors." PLOS Genetics 12(1):e1005811
Becirovic et al. (2016) "AAV Vectors for FRET-Based Analysis of Protein-Protein Interactions in Photoreceptor Outer Segments." Front Neurosci. 10:356
Boye et al. (2013) "A comprehensive review of retinal gene therapy" Molecular therapy, 21 509-519.
Brutlag Comp. App. Biosci. 6 (1990), 237-245
Cai et al, Exp Eye Res. 2010 Aug;91(2): 186-94.
Chao et ai., (2000) Molecular Therapy 2:619
Dalkara et al. (2013) "In vivo-directed evolution of a new adeno-associated virus for therapeutic outer retinal gene delivery from the vitreous." Science Translational Medicine, 5(189) 189ra76
D'Costa et al. (2016) "Practical utilization of recombinant AAV vector reference standards: focus on vector genomes titration by free ITR qPCR." Mol. Ther. Methods Clin. Dev. 5:16019
Eberle et al. (2011) "integration of transplanted CD73-positive photoreceptor precursors into adult mouse retina, Investigative ophthalmology & visual science,52, 6462-6471.
Eberle et al. (2014) "Subretinal transplantation of MACS purified photoreceptor precursor cells into the adult mouse retina." J. Vis. Exp. 84:e50932
Ellis et al. (2013) "Zinc-finger nuclease-mediated gene correction using single AAV vector transduction and enhancement by Food and Drug Administration-approved drugs" Gene Ther. 20(1):35-42.
Fei and Hughes (2001) "Transgenic expression of the jellyfish green fluorescent protein in the cone photoreceptors of the mouse" Visual neuroscience, 18, 615-623.
Fisher et al, 1993 J. Virol., 70:520-532.
Fei et al. (2003) "Development of the cone photoreceptor mosaic in the mouse retina revealed by fluorescent cones in transgenic mice." Mol. Vision 9:31-42
Feodorova et al. (2015) "Quick and reliable method for retina dissociation and separation of rod photoreceptor perikarya from adult mice." MethodsX 2:39-46
Fradot M et al. May 2011 Gene therapy in ophthalmology: validation on cultured retinal cells and explants from postmortem human eyes. Human gene therapy. 22(5): 587-93
Girod et al. (1999) "Genetic capsid modifications allow efficient re-targeting of adeno-associated virus type 2. Nat. Med. 5: 1052-1056
Hacker et al. (2005) "Adeno-associated virus serotypes 1 to 5 mediated tumor cell directed gene transfer and improvement of transduction efficiency." J. Gene Med. 7(11): 1429-38
Hellstrom et al. (2009) "Cellular tropism and transduction properties of seven adeno-associated viral vector serotypes in adultretina after intravitreal injection, Gene therapy, 16, 521-532.
Henikoff Proc. Natl. Acad. Sci., USA, 89, (1989), 10915
Kern et al. (2003) "Identification of a heparin-binding motif on adeno-associated virus type 2 capsids" Journal of virology, 77, 11072-11081
Kahle N A et al., Hum. Gene Ther. Clin. Dev., September 2018, 29(3):121-131
Koch et al. (2012) Gene therapy restores vision and delays degeneration in the CNGB1−/− mouse model of retinitis pigmentosa. Hum. Mol. Genet.: 4486-4496
Kotterman and Schaffer (2014) " Engineering adeno-associated viruses for clinical gene therapy" Nat. Rev. Genet., 15, 445-451

Lambard et al, PLoS One, Oct. 2010, 5(10):e13025.
Lebherz et al. (2008) "Novel AAV serotypes for improved ocular gene transfer" The journal of gene medicine, 10, 375-382.
Le Guiner et al. (2011) "Biodistribution and shedding of AAV vectors" Methods in molecular biology 807, 339-359.
MacLaren et al. (2014) "Retinal gene therapy in patients with choroideremia: initial findings from a phase 1/2 clinical trial" Lancet, 383, 1129-1137.
Maguire et al. (2008) "Safety and efficacy of gene transfer for Leber's congenital amaurosis, N. Engl. J. Med., 358 2240-2248.
Mekasa et al. (2009) "Genetic differences among C57BL/6 Substrains" Exp. Anim. 58(2), 141-149.
Michalakis et al. (2010) Restoration of Cone Vision in the CNGA3$^{-/-}$ Mouse Model of Congenital Complete Lack of Cone Photoreceptor Function Mol. Ther.: 2057-2063
Michelfelder et al. (2011) "Peptide ligands incorporated into the threefold spike capsid domain to re-direct gene transduction of AAV8 and AAV9 in vivo" PloS one, 6, e23101.
Millington-Ward et al, Molecular Therapy, April 2011, 19(4): 642-649.
Mussolino et al, Gene Ther., July 2011, 18(7):637-45).
Muzyczka, (1992) Curr. Topics Microbiol. Immunol. 158:97
Morrissey et al, BMC Dev., Biol., January 2011, 11:3.
Mühlfriedel et al. (2013) "Optimized technique for subretinal injections in mice" Methods in molecular biology, 935, 343-349.
Nathwani et al. (2014) "Long-term safety and efficacy of factor IX gene therapy in hemophilia B" N. Engl. J. Med., 371 (2014) 1994-2004.
Nicord et al, J. Gene Med., December 2007, 9(12): 1015-23.
Nickiin et al. (2001) "Efficient and selective AAV2-mediated gene transfer directed to human vascular endothelial cells" Molecular therapy: the journal of the American Society of Gene Therapy 4, 174-181
Ochakovski et al. (2017) "Retinal Gene Therapy: Surgical Vector Delivery in the Translation to Clinical Trials." Front Neurosci. 11:174
Opie et al. (2003) "Identification of amino acid residues in the capsid proteins of adeno-associated virus type 2 that contribute to heparin sulfate proteoglycan binding, Journal of virology, 77, 6995-7006.
O'Reilly M, et al. Am. J. Hum. Genet. 2007 July; 81(1): 127-35.
Perabo et al. (2003)" In vitro selection of viral vectors with modified tropism: the adeno-associated virus display, Molecular therapy: the journal of the American Society of Gene Therapy, 8, 151-157.
Perabo et al. (2006) "Heparan sulfate proteoglycan binding properties of adeno-associated virus retargeting mutants and consequences for their in vivo tropism" Journal of virology, 80, 7265-7269.
Sallach et al. (2014) "Tropism-modified AAV vectors overcome barriers to successful cutaneous therapy" Molecular therapy: the journal of the American Society of Gene Therapy, 22, 929-939.
Sambrook et al, Molecular Cloning: A Laboratory Manual, Cold Spring Harbor Press, Cold Spring Harbor, NY
J. Samulski, Chapel Hill, NC; Xiao, Li and Samulski (1998) "Production of high-titer recombinant adeno-associated virus vectors in the absence of helper adenovirus." J. Virol. 72: 2224-2232
Schön et al. (2015) "Retinal gene delivery by adeno-associated virus (AAV) vectors:Strategies and applications" European journal of pharmaceutics and biopharmaceutics,
Simonelli et al. (2010) "Gene therapy for Leber's congenital amaurosis is safe and effective through 1.5 years after vector administration" Molecular therapy: the journal of the American Society of Gene Therapy, 18 (2010) 643-650.
Sonntag et al. (2011) "The Assembly-Activating Protein Promotes Capsid Assembly of Different Adeno-Associated Virus Serotypes" J. Virol. 85(23): 12686-12697
Sun et al, Int. J. Cancer. 2010 Feb 1; 126(3):764-74
Tan et al. (2004) "Expression of cone-photoreceptor-specific antigens in a cell line derived from retinal tumors in transgenic mice." Investigative Ophthalmology & Visual Science 45 764-768
Thompson Nucl. Acids Res. 2 (1994), 4673-4680
Trapani et al. (2014) "Vector platforms for gene therapy of inherited retinopathies" Prog. Retin Eye Res.,
Wang and I. Verma, 1999 Proc. Natl. Acad. Sci., USA, 96:3906-3910
Xiao, Li and Samulski (1998) "Production of high-titer recombinant adeno-associated virus vectors in the absence of helper adenovirus." J. Virol. 72: 2224-2232.
Xie et al. (2002) "The atomic structure of adeno-associated virus (AAV-2), a vector for human gene therapy" Proceedings of the National Academy of Sciences of the United States of America, 99 10405-10410.
Zhong (2008) "Tyrosine-phosphorylation of AAV2 vectors and its consequences on viral intracellular trafficking and transgene expression" Virology, 381, 194-202.
Petrs-Silva et al. (2009) "High-efficiency transduction of the mouse retina by tyrosine-mutant AAV serotype vectors" Molecular therapy: the journal of the American Society of Gene Therapy, 17, 463-471.
Zeitz et al, Am. J. Hum. Genet. 2013 Jan 10; 92(1):67-75
Zhong et al. (2008) "Next generation of adeno-associated virus 2 vectors: point mutations in tyrosines lead to high-efficiency transduction at lower doses" Proceedings of the National Academy of Sciences of the United States of America, 105, 7827-7832
Zolotukhin et al. (1999) "Recombinant adeno-associated virus purification using novel methods improves infectious titer and yield. Gene Ther. 6: 973-985
U.S. Pat. No. 5,478,745
PCT/EP2008/004366
U.S. Pat. No. 9,610,354 B2
WO 1996/000587 A1
WO 2010/093784.
U.S. Pat. No. 5,478,745
WO 00/28004

The invention claimed is:

1. An adeno-associated virus (AAV), the AAV comprising a capsid protein comprising
an insertion of at least 6-8 amino acids between the positions corresponding to position 587 and 588 of SEQ ID NO: 1, wherein the insertion sequence has from the N-terminus to the C-terminus the formula I:

$X_{1A}\text{-}X_{1B}\text{-}X_2\text{-}X_3\text{-}X_4\text{-}X_5\text{-}X_6\text{-}X_7$ (formula I), wherein $X_5$ is selected from P (Pro), L (Leu) and V (Val);
wherein $X_7$ is R (Arg);
wherein $X_{1A}$ and/or $X_{1B}$ is/are selected from G (Gly), S (Ser), N (Asn), V and P;
wherein $X_2$ is selected from L, S and N;
wherein $X_3$ is selected from S, P, T (Thr), Q (Gln);
wherein $X_4$ is selected from P, G, S, A (Ala) and T;
wherein $X_6$ is selected from T, P, N, Q and S; and
wherein $X_{1A}$ and/or $X_{1B}$ are independently optionally absent or present, or or
wherein $X_5$ is selected from S and T;
wherein $X_7$ is S;
wherein $X_{1A}$ and/or $X_{1B}$ is/are selected from G, R, H (His) and S;
wherein $X_2$ is selected from A, S and Q;
wherein $X_3$ is selected from H, N and A;
wherein $X_4$ is selected from R, Q and D (Asp);
wherein $X_6$ is selected from R, S and D; and
wherein $X_{1A}$ and/or $X_{1B}$ are independently optionally absent or present, or
wherein $X_5$ is selected from A and Q;
wherein $X_7$ is A;
wherein $X_{1A}$ and/or $X_{1B}$ is/are selected from N and R;
wherein $X_2$ is selected from S and G;
wherein $X_3$ is selected from R and S;
wherein $X_4$ is selected from P and L;
wherein $X_6$ is selected from A and N; and
wherein $X_{1A}$ and/or $X_{1B}$ are independently optionally absent or present
further wherein the AAV has the following properties:
(a) viral AAV DNA is present in mouse retinal nuclear extracts after 24 hours, when the AAV is administered intravenously into the tail vein of a C57-BL6J mouse, and
(b)(i) viral AAV DNA is present in MAC-sorted rods as detected by anti-CD73-coated magnetic beads 24 hours after AAV administration when the AAV is administered intravenously into the tail vein of a C57-BL6J mouse for rod sorting, and/or (ii) viral AAV DNA is present in FACS-sorted cones 24 hours after AAV administration when the AAV is administered intravenously into the tail vein of RG-eGFP mice (line R685933) for cone sorting, wherein the cones express eGFP and are FACS sorted based on their eGFP expression.

2. The AAV of claim 1, wherein wherein $X_{1A}$ is absent and $X_{1B}$ is present or wherein $X_{1B}$ is absent and $X_{1A}$ is present.

3. The AAV of claim 1, wherein the insertion sequence has from the N-terminus to the C-terminus the formula II:

$L_3\text{-}L_2\text{-}L_1\text{-}X_{1A}\text{-}X_{1B}\text{-}X_2\text{-}X_3\text{-}X_4\text{-}X_5\text{-}X_6\text{-}X_7\text{-}L_4\text{-}L_5\text{-}L_6$ (formula II), wherein L is a flexible amino acid; and
wherein $L_1$, $L_2$, $L_3$, $L_4$, $L_5$ and $L_6$ are independently selected from Ala, Leu, Gly, Ser and Thr; and
wherein $L_1$, $L_2$, $L_3$, $L_4$, $L_5$ and $L_6$ are independently optionally absent or present.

4. The AAV of claim 3, wherein one of $X_{1A}$ or $X_{1B}$ is present and the other one of $X_{1A}$ or $X_{1B}$ is absent, and wherein all of $L_1$, $L_2$, $L_3$, $L_4$ and $L_5$ are present, and wherein $L_6$ is absent.

5. The AAV of claim 1, wherein $X_{1A}$ and/or $X_{1B}$ and/or $X_2$ and/or $X_3$ is not an acidic amino acid.

6. The AAV of claim 1, wherein one of $X_{1A}$ or $X_{1B}$ is present and the other one of $X_{1A}$ or $X_{1B}$ is absent and wherein $X_2$ is not a basic or acidic amino acid.

7. The AAV of claim 1, wherein $X_{1A}$ and/or $X_{1B}$ and/or $X_2$ and/or $X_3$ and/or $X_4$ and/or $X_6$ is not a hydrophobic-aromatic amino acid.

8. A pharmaceutical composition comprising
a therapeutically effective amount of the AAV of claim 1; and
at least one pharmaceutically acceptable carrier and/or at least one excipient.

9. A kit comprising an AAV of claim 1, and further comprising:
i) one or more buffers;
ii) one or more oligonucleotides;
iii) one or more active ingredients; and
iv) one or more syringes suitable for intravitreal injection.

10. A kit comprising an AAV of claim 1, and further comprising:
i) one or more buffers;
ii) one or more oligonucleotides;
iii) one or more active ingredients; and
iv) a container suitable for providing eye drops.

11. The AAV of claim 3, wherein $X_5$ is selected from P (Pro), L (Leu) and V (Val), and $X_7$ is R (Arg);
wherein $X_{1A}$ and/or $X_{1B}$ is/are selected from G, S, N, V and P;
wherein $X_2$ is selected from L, S and N;
wherein $X_3$ is selected from S, P, T, Q;
wherein $X_4$ is selected from P, G, S, A and T;
wherein $X_6$ is selected from T, P, N, Q and S and wherein $L_1$, $L_2$, $L_3$, $L_4$, $L_5$ and $L_6$ are present; and
wherein $X_{1A}$ and/or $X_{1B}$ are independently optionally absent or present.

12. The AAV of claim 1, wherein the AAV is AAV2.

13. The AAV of claim 11, wherein the AAV is AAV2.

14. The AAV of claim 1, wherein the AAV comprises the insertion sequence selected from the group consisting of GLSPPTR (SEQ ID NO: 10), SSPGLPR (SEQ ID NO: 11), NSTSVNR (SEQ ID NO: 12), VSSSLQR (SEQ ID NO: 13), PNQAPPR (SEQ ID NO: 14), NNPTPSR (SEQ ID NO: 15), GAHRSDS (SEQ ID NO: 16), RANQTSS (SEQ ID NO: 17), HSARTDS (SEQ ID NO: 18), SQNDSRS (SEQ ID NO: 19), NSRPAAA (SEQ ID NO: 20) and RGSLQNA (SEQ ID NO: 21).

15. The AAV of claim 14, wherein the AAV comprises the insertion sequence selected from the group consisting of GLSPPTR (SEQ ID NO: 10), SSPGLPR (SEQ ID NO: 11), NSTSVNR (SEQ ID NO: 12), VSSSLQR (SEQ ID NO: 13), PNQAPPR (SEQ ID NO: 14) and NNPTPSR (SEQ ID NO: 15).

16. The AAV of claim 15, wherein the AAV comprises the insertion sequence GLSPPTR (SEQ ID NO: 10) or NNPTPSR (SEQ ID NO: 15).

17. The AAV of claim 11, wherein the AAV comprises the insertion sequence GLSPPTR (SEQ ID NO: 10) or NNPTPSR (SEQ ID NO: 15).

* * * * *